United States Patent [19]
Sessler et al.

[11] Patent Number: 5,457,183
[45] Date of Patent: * Oct. 10, 1995

[54] HYDROXYLATED TEXAPHYRINS

[75] Inventors: Jonathan L. Sessler, Austin, Tex.; Tarak D. Mody; Gregory W. Hemmi, both of Sunnyvale, Calif.; Vladimir Král, Na Kozařoa, Czechoslovakia

[73] Assignee: Board of Regents, The University of Texas System, Austin, Tex.

[ * ] Notice: The portion of the term of this patent subsequent to Oct. 12, 2010, has been disclaimed.

[21] Appl. No.: 135,118

[22] Filed: Oct. 12, 1993

Related U.S. Application Data

[63] Continuation-in-part of Ser. No. 75,123, Jun. 9, 1993, abandoned, which is a continuation-in-part of Ser. No. 822,964, Jan. 21, 1992, Pat. No. 5,252,720, which is a continuation-in-part of Ser. No. 771,393, Sep. 30, 1991, abandoned, which is a continuation-in-part of Ser. No. 539,975, Jun. 18, 1990, Pat. No. 5,162,509, which is a division of Ser. No. 320,293, Mar. 6, 1989, Pat. No. 4,935,498.

[51] Int. Cl.⁶ .................................................. C07D 487/22
[52] U.S. Cl. ....................... 534/11; 530/345; 530/391.3; 530/391.5; 530/405; 534/13; 534/15; 534/16; 536/17.1; 536/17.3; 536/17.4; 540/145; 540/465; 540/472
[58] Field of Search .................. 534/11, 13, 15, 534/16; 540/145, 465, 472; 536/17.1, 17.4, 17.3; 530/345, 391.3, 391.5, 405

[56] References Cited

U.S. PATENT DOCUMENTS

| | | | |
|---|---|---|---|
| 4,878,891 | 11/1989 | Judy et al. | 604/5 |
| 4,883,790 | 11/1989 | Levy et al. | 540/145 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,162,509 | 11/1992 | Sessler et al. | 534/15 |
| 5,252,270 | 10/1993 | Sessler et al. | 534/11 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1994 | Sessler et al. | 204/157.5 |

FOREIGN PATENT DOCUMENTS

| | | |
|---|---|---|
| 0111418A2 | 6/1984 | European Pat. Off. . |
| 0196515A1 | 10/1986 | European Pat. Off. . |
| 0233701A2 | 8/1987 | European Pat. Off. . |
| WO93/14093 | 7/1973 | WIPO . |
| WO90/10633 | 9/1990 | WIPO . |

OTHER PUBLICATIONS

Sessler et al., "Gadolinium (III) Texaphyrin: A Novel MRI Contrast Agent," *Journal of the American Chemical Society*, 115 (22):10, 368–10, 369, 1993.
Iverson et al., "Interactions Between Expanded Porphyrins and Nucleic Acids," *Pure Applied Chemistry*, 66(4): 845–850, 1994.
Matthews et al., "Inactivation of Viruses with Photoactive Compounds," *Blood Cells*, 18(1): 75–89, 1992.
Ehrenberg et al., "Spectroscopy, Photokinetics and Cellular Effect of Far–Red and Near Infrared Absorbing Photosensitizers," *Proc. SPIE–Int. Soc. Opt. Eng 1992*, 1645 (*Proc. Opt. Methods Tumor Treat. Dect.: Mech. Tech. Photodyn. Ther. . .*, 259–263, 1992.
Thaller et al., "Potential Use of Radiolabelled Porphyrins for Tumor Scanning," *Porphyrin Photosensitization*, Kessel and Dougherty, Eds., Plenum Press, New York and London, Publisher, pp. 265–278, 1981.
Magda et al., "Site–Specific Hydrolysis of RNA by Europium (III) Texaphyrin Conjugated to a Synthetic Oligodeoxyribonucleotide," *Journal of the American Chemical Society*, 116(16): 7439–7440, 1994.
Koenig et al., "PDT of Tumor–Bearing Mice Using Liposome Delivered Texaphyrins," International Conference, Milan, Italy, Biosis citation only, Jun. 24–27, 1992.
Nam–Chiang Wang et al., "Pyrrole chemistry. XVII. Alkylation of the pyrrolyl ambident anion," *Can. J. Chem.*, 55:4112–4116, 1977.
Jonahtan L. Sessler et al., "Texaphyrins: Synthesis and Applications," *Acc. Chem. Res.*, 27(2) :43–50, 1994.
Stuart W. Young et al., "Preclinical Evaluation of Gadolinium (III) Texaphyrin Complex," *Investigative Radiology*, 29(3): 330–338, 1994.
T. D. Mody et al., "Lutetium (III) Texaphyrin: A Novel Photodynamic Therapy Agent," Abstract, *22nd Annual American Society for Photobiology*, Scottsdale, Ariz., Jun. 25–29, 1994.
Abid et al., "Lanthanide Complexes of Some Macrocyclic Schiff Bases Derived from Pyridine–2,6–dicarboxaldehyde and α,ω–Primary Diamines", *Inorg. Chim. Acta*, vol. 95, (1984) 119–125.

(List continued on next page.)

*Primary Examiner*—Richard L. Raymond
*Attorney, Agent, or Firm*—Arnold, White & Durkee

[57] ABSTRACT

A method of using texaphyrins as radiosensitizers. Advantageous properties of texaphyrins for use as a radiosensitizer include i) a low redox potential which allows radiation induced solvated electrons to flow to texaphyrin rather than neutralizing hydroxyl radicals, allowing the hydroxyl radicals to cause cellular damage, ii) a relatively stable texaphyrin radical which, nevertheless, reacts readily to covalently modify neighboring molecules causing further cellular damage, and iii) intrinsic biolocalization and indifference to the presence of $O_2$ which allow texaphyrin to be particularly effective for treating the hypoxic areas of solid tumors. Sensitizer enhancement ratios of 1.62 and 2.2 were achieved at 20 μM and 80 μM gadolinium-texaphyrin, respectively, with a mouse leukemia cell line. Methods of treatment for an individual having a tumor include the use of a texaphyrin as a radiosensitizer and as an agent for photodynamic tumor therapy, or the use of a texaphyrin for internal and for external ionizing radiation. New water soluble hydroxy-substituted texaphyrins are described.

59 Claims, 51 Drawing Sheets

OTHER PUBLICATIONS

Acholla et al., "Binucleating Tetrapyrrole Macrocycles", *J. Am. Chem. Soc.*, vol. 107 (1985) 6902–6908.

Acholla et al., "Binucleating Accordian Tetrapyrrole Macrocycle", *Tetrahedron Lett.*, vol. 25 (1984) 3269–3270.

Agrawal et al., "Cellular Uptake and Anti–HIV Activity of Oligonucleotides and Their Analogs," *Gene Regulation: Biology of Antisense RNA and DNA*, 273–283 1992.

Agrawal and Tang, "Efficient Synthesis of Oligoribonucleotide and Its Phosphorothioate Analogue Using H–Phosphonate Approach," *Tetrahedron Letters*, 31(52): 7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Ansell, "X–Ray Crystal Structure of the Pentagonal Bipyramidal Nickel (11) Complex [$Ni^{11}(L) (H_2O)_2$] $(BF_4)_2$ and the Selective Stabilisation of the Nickel (1) Oxidation State by a Quinquedentate Macrocyclic Ligand", *J. Chem. Soc., Chem. Commun.* (1982) 546–547.

Basile et al., "Metal–Activated Hydrolytic Cleavage of DNA," *J. Am. Chem. Soc., 109:7550–7551, 1987.*

Bauer et al., "Sapphyrins: Novel Aromatic Pentapyrrolic Macrocycles", *J. Am. Chem. Soc.*, vol. 105, (1983) 6429–6436.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds,"*Proc. Natl. Acad. Sci. USA*, 88:4080–4083, 1991.

Broadhurst et al., "Preparation of Some Sulphur–containing Polypyrrolic Macrocycles. Sulphur Extrusion from a *meso*–Thiaphlorin", *J. Chem. Soc., Chem. Commun.* (1970) 807–809.

Broadhurst et al., "18– and 22–π–Electron Macrocycles Containing Furan, Pyrrole, and Thiophene Rings", *J. Chem. Soc., Chem. Commun.* (1969) 1480–1482.

Broadhurst et al., "New Macrocyclic Aromatic Systems Related to Porphins", *J. Chem. Soc., Chem. Commun.* (1969) 23–24.

Broadhurst et al., "The Synthesis of 22 π–Electron Macrocycles. Sapphyrins and Related Compounds", *J. Chem. Soc. Perkin Trans.* 1 (1972) 2111–2116.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13) :4951–4958, 1992.

Chin et al., "Co(III) Complex Promoted Hydrolysis of Phosphate Diesters: Comparison in Reactivity of Rigid *cis*–Diaquotetraazacobalt (III) Complexes," *J. Am. Chem. Soc.*, 111:186–190, 1989.

Chin and Banaszczyk, "Rate–Determining Complexation in Catalytic Hydrolysis of Unactivated Esters in Neutral Water," *J. Am. Chem. Soc.*, 111:2724–2726, 1989.

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38) :5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Cuellar et al., "Synthesis and Characterization of Metallo and Metal–Free Octaalkylphthalocyanines and Uranyl Decaalkysuperphthalocyanines", *Inorg. Chem.*, vol. 20 (1981) 3766–3770.

Day et al., "Large Metal Ion–Centered Template Reactions. A Uranyl Complex of Cyclopentakis (2–iminoisoindoline)", *J. Am. Chem. Soc.*, vol. 97 (1975) 4519–4527.

De Cola et al., "Hexaaza Macrocyclic Complexes of the Lanthanides", *Inorg. Chem.*, vol. 25 (1986) 1729–1732.

Dougherty, "Photosensitizers: Therapy and Detection of Malignant Tumors", *Photochem. Photobiol.*, vol. 45 (1987) 879–889.

Furuta et al., "Phosphate Anion Binding: Enhanced Transport of Nucleotide Monphosphates Using a Sapphyrin Carrier," *J. Am. Chem. Soc.*, 113:6677–6678, 1991.Gosmann et al., "Synthesis of a Fourfold Enlarged Porphyrin with an Extremely Large, Diamagnetic Ring–Current Effect", *Angew. Chem., Int. Ed Engl.*, vol. 25 (1986) 1100–1101.

Gossauer, "Syntheses of Some Unusual Polypyrrole Macrocycles", *Bull.*

Soc. Chim. Belg., vol. 92 (1983) 793–795.

Hanvey et al., "Antisense and Antigene Properties of Peptide Nucleic Acids,

" *Science*, 258–1481–1485, 1992.

Harriman et al., "Metallotexaphyrins: A New Family of Photosensitisers for

Efficient Generation of Singlet Oxygen", *J. Chem. Soc., Chem. Commun.*, (1989) 314–316.

Hendry and Sargeson, "Metal Ion Promoted Phosphate Ester Hydrolysis. Intramolecular Attack of Coordinated Hydroxide Ion," *J. Am. Chem. Soc., 111:2521–2527, 1989.*

Kim and Chin, "Dimethyl Phosphate Hydrolysis at Neutral pH,"*J. Am.*

Chem. Soc., 114:9792–9795, 1992.

Knubel et al., "Biomimetic Synthesis of an Octavinylogous Porphyrin with an

Aromatic [34] Annulene System", *Angew. Chem., Int. Ed. Engl.,* vol. 27 (1988) 1170–1172.

Komiyama et al., "Unprecedentedly Fast Hydrolysis of the RNA Dinucleoside

Monophosphates ApA and UpU by Rare Earth Metal Ions," *J. Chem. Soc.*

Chem. Commun., 640–641, 1992.

Lauffer, "Paramagnetic Metal Complexes as Water Proton Relaxation Agents for NMR Imaging: Theory and Design", *Chem. Rev.* vol. 87 (1987) 901–927.

LeGoff et al., "Synthesis of a [1,5,1,5] Platyrin, a 26 π–Electron

Tetrapyrrolic Annulene", *J. Org. Chem.* vol. 52 (1987) 710–711.

Marks et al., "Large Metal Ion–Centered Template Reactions. Chemical and Spectral Studies of the Superphtalocyanine Dioxocyclopentakis (1–iminoisoindolinato) uranium (VI) and Its Derivatives", *J. Am. Chem. Soc., vol. 100 (1978)* 1695–1705.

Menger et al., "Phosphate Ester Hydrolysis Catalyzed by Metallomicelles," *J. Am. Chem. Soc.,* 109:2800–2803, 1987.

Modak et al., "Toward Chemical Ribonucleases. 2. Synthesis and Characterization of Nucleoside–Bipyridine Conjugates. Hydrolytic Cleavage of RNA by Their Copper (II) Complexes," *J. Am. Chem. Soc.,* 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.,* 114:1903–1905, 1992.

Phillips and Wasserman, "Promise of Radiosensitizers and Radioprotectors in the Treatment of Human Cancer," *Cancer Treatment Reports,* 68(1) :291–301, 1984.

Ranganathan et al., "Design of a Chemical Nuclease Model with (Lys)$_2$Cu as the Core Motif," *Journal of the Chemical Society,* 4:337–339, 1993.

Rexhausen et al., "The Synthesis of a New 22 π–Electron Macrocycle: Pentaphyrin", *J. Chem. Soc., Chem. Commun.* (1983) 275.

Sessler, Jonathan L., "Texas–Sized Molecule," *Discovery,* 13(1): 44–49, 1993.

Sessler et al., "Photodynamic Inactivation of Enveloped Viruses Using Sapphyrin, α 22 π–Electron Expanded Porphyrin: Possible Approaches to Prophylactic Blood Purification Protocols," *SPIE Photodynamic Therapy: Mechanisms II.* 1203:233–245, 1990.

Sessler et al., "The Coordination Chemistry of Planar Pentadentate Porphyrin–Like Ligands", *Comm. Inorg. Chem.,* vol. 7 (1988) 333–350.

Sessler et al., "An Expanded Porphyrin: The Synthesis and Structure of a New Aromatic Pentadentate Ligand", *J. Am. Chem. Soc.,* vol. 110 (1988) 5586–5588.

Sessler et al., "A Water–Stable Gadolinium (III) Complex Derived from a new Pentadentate Expanded Porphyrin Ligand", *Inorg. Chem.,* vol. 28 (1989) 3390–3393.

Sessler et al., "Binding of Pyridine and Benzimidazole to a Cadmium Expanded Porphyrin: Solution and X–ray Structural Studies", *Inorg. Chem.,* vol. 28 (1989) 1333–1341.

Sessler et al., "Expanded Popyrins: The Synthesis and Metal Binding Properties of Novel Tripyrrane–Containing Macrocycles", *J. Coord. Chem.,* vol. 18 (1988) 99–104.

Sessler et al., "A Water–Stable Gadolinium (III) Complex Derived from a New Pentadentate", *Chem. Absts.,* vol. 111:125716e (2 Oct. 1989) p. 720.

Sessler et al., "The Synthesis and Structure of a Novel 22 π–Electron Aromatic Pentadentate Macrocyclic Ligand: An Expanded Porphyrin", Toronto ACS Meeting, Jun. 1988.

Sessler et al., "'Texaphyrin': A Novel 22 π–Electron Aromatic Pentadentate Macrocyclic Ligand", ACS meeting, Los Angeles, Sep. 1988.

Sessler et al., "Triphyrroledimethine–derived (Texaphyrin–type) Macrocycles: Potential Photosensitizers Which Absorb in the Farred Spectral Region", SPIE, vol. 1426, Optical Methods for Tumor Treatment and Early Diagnosis: Mechanism and Technique (1991) 318–329.

Sessler et al., "Preparation of Lanthanide (III) Texaphyrin Complexes and Their Applications to Magnetic Resonance Imaging and Photodynamic Therapy," Abstracts of Papers, Part 1, 204th ACS National Meeting, Aug. 23–28, 1992, Washington, D.C.

Sessler et al., "Synthesis and Applications of Schiff–Base Derived Expanded Porphyrins," *Abstracts of Papers,* Part 1, 204th ACS National Meeting, Aug. 23–28, 1992, Washington, D.C.

Sessler et al., "Sapphyrins: New Life for and Old Expanded Porphyrin," Synlett, 127–134, 1991.

Sessler et al., "Sapphyrins and Heterosapphyrins," *Tetrahedron,* 48(44) :9661–9672, 1992.

Sessler et al., "Synthesis and Structural Characterization of Lanthanide(III) Texaphyrins," *Inorganic Chemistry,* 32(14): 3175–3187, 1993.

Sessler et al., "Synthesis and Crystal Structure of a Novel Tripyrane–Containing Porphyrinogen–like Macrocycle," *J. Org. Chem.,* 52:4394–4397, 1987.

Sessler and Burrell, "Expanded Porphyrins," *Topics in Current Chemistry,* 161:180–273, 1991.

Shelton and Morrow, "Catalytic Transesterification and Hydrolysis of RNA by Zinc(II) Complexes," *Inorganic Chemistry,* 30:4295–4299, 1991.

Stern et al., "Hydrolysis of RNA by Transition–Metal Complexes," J. Am. Chem. Soc., 112:5357–5359, 1990.

Stinson, "Unusual Porphyrin Analog Promises Many Applications," *Chemical and Engineering News,* Aug. 8, 1988, pp. 26–27.

Sumaoka et al., "Remarkably Fast Hydrolysis of 3',5'–= Cyclic Adenosine Monophosphate by Cerium(III) Hydroxide Cluster," J. Chem. Soc. Chem. Comm., 2 pages, 1992.

"Tentative Rules for Carbohydrate Nomenclature Part 1 (1969)," Handbook of Biochemistry and Molecular Biology, 3rd ed., Fasman, Ed., CRC Press, Cleveland, Ohio.

To and Neiman, "The Potential For Effective Antisense Inhibition of Retroviral

Replication Mediated by Retroviral Vectors," *Gene Regulation: Biology of*
Antisense RNA and DNA, 261–271, 1992.

Tweedle et al, "Principles of Contrast–Enhanced MRI", in Magnetic Resonance
Imaging, 2nd ed. Partain, et al, Eds., W. B. Saunders: Philadelphia, vol. I (1988)
793–809.

Vogel et al., "Porphycene–a Novel Porphin Isomer", *Angew. Chem., Int.*
Ed. Engl., vol. 25 (1986) 257–259.

Vogel et al., "2,7,12,17–Tetrapropylporphycene–Counterpart of Octaethylporphyrin
in the Porphycene Series", *Angew. Chem., Int. Ed. Engl.,*
vol. 26 (1987) 928–931.

Wagener and Beyrich, "Radiosensitizer–Biochemie und Tumortherapeutische
Erfahrungen," *Pharmazie*, 47:815–824, 1992.

"2–Äthylamino–2–methyl–propanol–(1)," *Beilstein's*
Handbuch, vol. 4 (1950) p. 785.

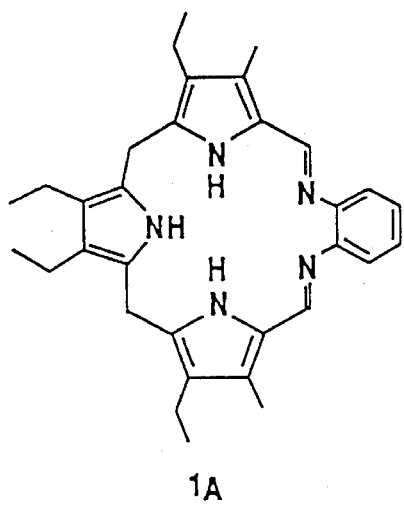
1A
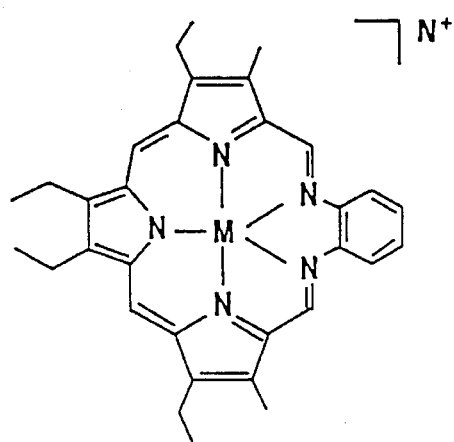
1B  M = H, N = 0
1C  M = Cd, N = 1
FIG. 1A
FIG. 1B

5A  R = CH₃

5B   M = H,   R = CH₃ , N = 0
5C   M = Gd,  R = CH₃   N = 2
5D   M = Eu,  R = CH₃ , N = 2
5E   M = Sm,  R = CH₃ , N = 2

HYDROXYLATED TEXAPHYRINS

Research leading to the present invention was supported in part by the National Science Foundation (PYI 1986 and CHE 9122161) and the National Institute of Health (AI 28845). The U.S. government therefore has certain rights in the invention.

This application is a continuation-in-part application of then U.S. Ser. No. 08/075,123, filed Jun. 9, 1993, now abandoned. U.S. Ser. No. 08/075,123 is a continuation-in-part application of then copending U.S. Ser. No. 07/822,964 filed Jan. 21, 1992, since issued as U.S. Pat. No. 5,252,720, Oct. 12, 1993. U.S. Ser. No. 07/822,964 was a continuation-in-part application of 07/771,393, now abandoned, which was a continuation-in-part of Ser. No. 07/539,975, since issued as U.S. Pat. No. 5,162,509 on Nov. 10, 1992 and a U.S. Ser. No. 07/539,975 was a divisional application of U.S. Ser. No. 07/320,293, since issued as U.S. Pat. No. 4,935,498, Jun. 19, 1990. The entire contents of the above-named patents and patent applications are incorporated by reference herein.

FIELD OF THE INVENTION

The present invention relates to the field of radiosensitizers and the use of texaphyrin metal complexes for radiosensitization.

BACKGROUND OF THE INVENTION

A radiosensitizer is an agent used to enhance the effect of radiation therapy. Radiation therapy relies of two types of ionizing radiation: (1) subatomic particle radiation, which consists of alpha particles, beta particles (electrons), neutrons, protons, mesons, and heavy ions, and (2) electromagnetic radiation, which exists as a family of waves of varying frequency, including high-frequency x-rays. Electromagnetic radiation in the form of x-rays is most commonly used in megavoltage radiation therapy to treat common malignant tumors. Gamma rays, a form of electromagnetic radiation similar to x-rays but emitted by radioactive isotopes of radium, cobalt, and other elements, are also commonly used.

Subatomic particle radiation and electromagnetic radiation transfer energy to tissues as discrete packets of energy, called photons, that damage both malignant and normal tissues by producing ionization within cells. The target for these ions most commonly is the intranuclear DNA.

The damaging effects of radiation therapy are mediated by the radiation products of water:

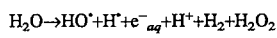

$$H_2O \rightarrow HO^{\cdot}+H^{\cdot}+e^{-}_{aq}+H^{+}+H_2+H_2O_2$$

The hydroxyl radical, $HO^{\cdot}$, is an oxidizing radical and is primarily responsible for radiation damage. The radical is extremely reactive and short lived. It causes damage primarily in the vicinity in which it is generated and if it comes in contact with a solvated electron ($e^{-}_{aq}$), it will be neutralized.

The $H^{\cdot}$ radical is a reducing radical produced in low yield and reacts to a small extent but in a non-useful way. It, therefore, is not significant in the mechanism of radiation damage.

Solvated electrons, $e^{-}_{aq}$, are strong reducing radicals and highly energetic particles. They are very small by comparison to the hydroxyl radical and travel great distances quickly. They will neutralize hydroxyl radicals readily. Therefore, one of the mechanisms of a radiosensitizer is to "soak up" solvated electrons and prevent them from neutralizing hydroxyl radicals, thereby, allowing hydroxyl radicals to do their damage.

Most of the existing anticancer drugs act at the DNA level, either by direct chemical interaction, as do alkylating agents, or by interference with DNA biosynthesis, as in the case of antimetabolites (Daoud, S. S. et al., 1991). The major limitation with these drugs is their lack of selectivity, since the structure and biosynthesis of DNA in normal cells is only marginally different from that in tumor cells (Tritton, T. R. et al., 1985). As a result, most of the existing antineoplastic reagents have undesirable toxic effects on rapidly dividing normal cells. To some degree, the specificity for hypoxic cells can be improved by proper selection of sidechains. Several classes of reagents have been programmed to attack cellular DNA, including reagents which intercalate between base pairs in the duplex and those which bind to the phosphate layer by electrostatic association.

The development of reagents that act against cellular loci other than DNA may lead to drugs that provide effective antitumor treatment and which are less toxic than currently available radiation sensitizers. One of these cellular loci is the cell membrane (Kale, R. K. et al., 1990). Some degree of drug specificity at this site seems possible because numerous subtle differences in composition, structure, organization, dynamics, and function exist between the surfaces of normal and hypoxic cells which may be exploited to design selective reagents. Thus, drugs which severely perturb membrane function or cause lipid peroxidation represent an important class of reagents. These systems are based on the formation of peroxyl radicals under in situ radiolysis in the presence of low concentrations of oxygen.

The biological responses to radiation-induced cell injury are modulated by various endogenous and exogenous radioprotectors (Painter, R. B., *Radiation Biology in Cancer Research*, pp. 59–68, 1980). Sulfhydryl compounds, including cysteine, cysteamine, and dithiothreitol, have been shown to protect living cells against the lethal effects of ionizing radiation. It has also been observed that depletion of cellular sulfhydryl compounds can result in radiosensitization (Biaglow, J. E. et al., 1983). Two main mechanisms may be inferred for the action of sulfhydryl substrates. One involves scavenging of water radiolysis products, notably hydroxyl radicals. Evidence has also accumulated to show that sulfhydryl compounds can repair radiation-induced damage to DNA by hydrogen atom donation to transient oxidized species (Cadet, J. et al., 1988). Thus, an important feature of drug design revolves around attempting to block the repair mechanism.

Cells may circumvent the lethal effects of toxins by altering the levels of proteins involved in their metabolic activation. Reduction in the levels of enzymes required for conversion of some reagents into their toxic metabolites has been shown to be an effective mode of drug resistance, particularly when the parent compound is relatively non-toxic (Townsend, A. J. et al., 1989). Enzymes may also play a key role in resistance by enabling cells to convert toxins into less active or more easily removed chemical species. Although some of these detoxification pathways have been well characterized for many environmental and industrial toxins, their role in cellular resistance to antineoplastic drugs has only recently been appreciated. Among the strikingly diverse set of enzymes found in mammalian cells, glutathione S-transferases seem to be especially effective for removing anticancer drugs from the system (Townsend, A. J. et al., 1989). Depletion of this enzyme could have a significant effect on the performance of certain drugs.

It is now recognized that cytotoxicity may result from minor changes in cellular levels of calcium or protons and from inhibition of gene expression. Such processes, if combined with selective uptake of reagent into infected cells, offer great potential for radiotherapy because they require minimal generation of the active agent. This is in contrast to lipid peroxidation which has to be widespread before effective necrosis is observed.

Hypoxic cells in solid tumors are relatively resistant to cell killing by radiation as well as by conventional chemotherapeutic drugs (Grau, C. et al., 1992). Although various types of electron-affinic reagents are known to promote radiosensitization of cells with diminished oxygen supply, relatively few show activity at nontoxic doses with in vivo models. Clinical trials with one of the better known reagents, misoimidazole, have revealed some therapeutic gain but the compound cannot be used at optimal dose due to neurotoxicity (Pan, S. -S. et al., 1990). Approaches aimed at improving the therapeutic performance of nitroimidazoles have included lowering the lipophilicity so as to restrict nervous tissue penetration and accelerate renal clearance and modifying the electron affinity. The objective has been to promote in situ formation of a stable π-radical anion that can react with cellular oxygen to form superoxide ions.

Hypoxia in solid tumors is known to result in a decreased effectiveness of ionizing radiation and hypoxic cells distant from blood vessels may also be resistant to drug-based therapy because of insufficient drug delivery, reduced drug activation under hypoxic and/or acidic conditions, or low activity against non-cycling hypoxic cells. On the other hand, certain drugs may be selectively toxic to hypoxic cells and might to used to improve treatment in radiotherapy. Information about the specific effects of reagents on well oxygenated and hypoxic cells is necessary for the development of rational chemotherapeutic regimens designed to attack each of the physiological tumor subpopulations. Thus, extensive in vitro testing of new reagents must be made under both aerobic and hypoxic conditions and promising reagents must be tested against established standards. The most common standards are cyclophosphamide, 5-fluorouracil, and misoimidazole. It has been reported (Grau, C. et al., 1988) that whereas 5-fluorouracil is more effective against well oxygenated cells, misoimidazole and cyclophosphamide are toxic towards both oxic and hypoxic cells under radiolysis.

The present invention provides new compounds for radiosensitization. Texaphyrins enhance radiation damage and the enhancement is unaffected by the present of oxygen. Texaphyrins and water soluble texaphyrins have been described in U.S. Pat. Nos. 4,935,498 and 5,162,509 and US applications Ser. Nos. 07/822,964, now U.S. Pat. No. 5,252,720 and 08/075,123, now abandoned, all of which are incorporated by reference herein.

LIST OF ABBREVIATIONS

EDC: 1-Ethyl-3-(3-dimethylaminopropyl) carbodiimide

Gy Gray: a unit of absorbed radiation dose equal to 100 rads

Txp (txph) (tx): Texaphyrin

SUMMARY OF THE INVENTION

The present invention provides a method of radiation therapy for a host harboring a tumor. The method includes the steps of administering to the host a water soluble hydroxy-substituted texaphyrin retaining lipophilicity and administering ionizing radiation to the host in proximity to the tumor. The texaphyrin exhibits greater biolocalization in the tumor relative to non-tumor tissue and has radiosensitization properties. A tumor may be a benign or malignant tumor or may be atheroma. A texaphyrin is an aromatic pentadentate expanded porphyrin analog and a texaphyrin having radiosensitization properties enhances cytotoxicity from ionizing radiation as compared to control experiments without the texaphyrin. Ionizing radiation includes but is not limited to x-rays, and internal and external gamma emitting radioisotopes.

A method of treating a host harboring a tumor comprising the steps of i) administering to the host a water soluble hydroxy-substituted texaphyrin retaining lipophilicity, ii) determining localization sites in the host by monitoring texaphyrin concentrations, and iii) administering ionizing radiation to the host in proximity to the tumor, is a further aspect of the present invention. Monitoring texaphyrin concentrations means measuring fluorescence of an administered free base texaphyrin or by reference to the metal of an administered texaphyrin metal complex. If the metal is paramagnetic, then magnetic resonance imaging is used for measurement, if the metal is a gamma emitting radioactive metal, then γ emission is used for measurement.

In each of these methods, the water soluble hydroxy-substituted texaphyrin may be complexed with a metal, although the metal is not central to the radiosensitization properties of the texaphyrins. The metal is important to the stability of the texaphyrin complex.

A further embodiment of the present invention is a method of treating a host harboring a tumor comprising the steps of i) administering to the host as a first agent a water soluble hydroxy-substituted texaphyrin retaining lipophilicity, ii) determining localization sites in the host by monitoring texaphyrin concentrations, iii) administering to the host as a second agent a water soluble hydroxy-substituted texaphyrin-diamagnetic metal complex retaining lipophilicity, and iv) administering ionizing radiation and photoirradiation in proximity to the tumor. The second agent has essentially identical biolocalization property and may exhibit the ability to generate singlet oxygen upon exposure to light. The photodynamic effect may be derived from anaerobic electron transfer processes. A preferred diamagnetic metal texaphyrin complex is the Lu(III), La(III) or In(III) complex of B2T2.

In these methods, determining localization sites may occur by observing fluorescence from the texaphyrin, in particular, a free base ring N-derivatized texaphyrin. When the first agent is complexed with a metal, the metal may be a gamma-emitting metal and determining localization sites would occur by gamma body imaging, or the metal may be a paramagnetic metal and determining localization sites would occur by magnetic resonance imaging. The ionizing radiation may be from an external source or the metal may be a radioactive metal. In that case, the ionizing radiation is from the radioactive metal in combination with radiation from an external source. Exhibiting greater biolocalization in the tumor relative to non-tumor tissue means having an inherently greater affinity for tumor tissue relative to non-tumor tissue. Essentially identical biolocalization property means the second agent is a texaphyrin derivative having about the same selective targeting characteristics in tissue as demonstrated by the first agent. The first agent and the second agent may be the same texaphyrin.

The texaphyrin may have the structure:

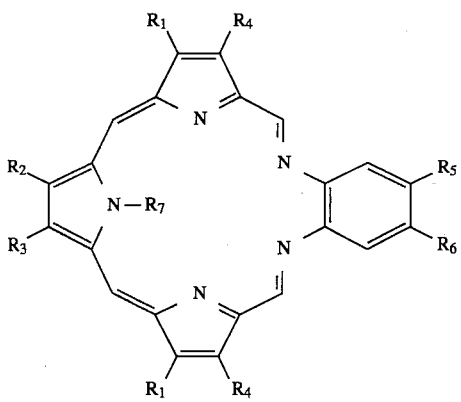

$R_1$, $R_2$, $R_3$, $R_4$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, biomolecule or a couple to a biomolecule. At least one of $R_1$, $R_2$, $R_3$, $R_4$, $R_5$ and $R_6$ is oxyhydroxyalkyl, saccharide, oxyalkyl, carboxyalkyl, carboxyamidealkyl, hydroxyalkyl, biomolecule or a couple to a biomolecule having at least one hydroxy substituent. $R_7$ is alkyl. In a preferred embodiment, $R_7$ is methyl.

The texaphyrin may have the structure:

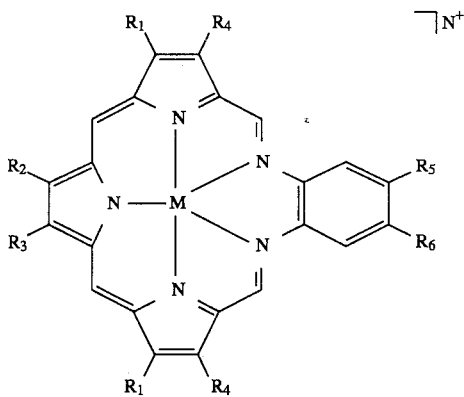

M may be H, a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2^{+2}$ or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$. $R_2$ and $R_3$ are $CH_2CH_3$, $R_4$ is $CH_3$, $R_1$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, biomolecule or a couple to a biomolecule where at least one of $R_1$, $R_5$, and $R_6$ is oxyhydroxyalkyl, saccharide, oxyalkyl, carboxyalkyl, carboxyamidealkyl, hydroxyalkyl, biomolecule or a couple to a biomolecule having at least one hydroxy substituent. N is 0, 1 or 2.

The oxyhydroxyalkyl may be $C_{(n-x)}H_{((2n+1)-2x)}O_xO_y$ or $OC_{(n-x)}H_{(2n+1)-2x)}O_xO_y$ where n is a positive integer from 1 to 10, x is zero or a positive integer less than or equal to n, and y is zero or a positive integer less than or equal to ((2n+1)-2x). The oxyhydroxyalkyl or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than ((2n+1)-q), q is zero or a positive integer less than or equal to 2n+1, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, or $N(R)OCC_{(m-w)}H_{((2m+1)-2w)}O_wO_y$. M is a positive integer from 1 to 10, w is zero or a positive integer less than or equal to m, z is zero or a positive integer less than or equal to ((2m+1)-2w). R is H, alkyl, hydroxyalkyl, or $C_mH_{((2m+1)-r)}O_zR^b_r$, where m is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide.

The carboxyamidealkyl is $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)$ $OCC_{(m-w)}H_{((2m+1)-2w)}O_wO_z$. M is a positive integer from 1 to 10, w is zero or a positive integer less than or equal to m, z is zero or a positive integer less than or equal to ((2m+1)-2w), and R is H, alkyl, hydroxyalkyl, or $C_mH_{((2m+1)-r)}O_zR^b_r$. M is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide.

The carboxyalkyl is $C_nH_{((2n+1)-q)}O_yR^c_q$ or $OC_nH_{((2n+1)-q)}O_yR^c_q$ where n is a positive integer from 1 to 10, y is zero or a positive integer less than ((2n+1)-q), q is zero or a positive integer less than or equal to 2n+1, and $R^c$ is $(CH_2)_nCO_2R^d$, $(CH_2)_nCONHR^d$ or $(CH_2)_nCON(R^d)_2$. N is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)$ $OCC_{(m-w)}H_{((2m+1)-2w)}O_wO_z$, where m is a less than or equal to m, z is zero or a positive integer less than or equal to ((2m+1)-2w), R is H, alkyl, hydroxyalkyl, or $C_mH_{((2m+1)-r)}O_zR^b_r$. M is a positive integer from 1 to 10, z is zero or a positive integer less than ((2m+1)-r), r is zero or a positive integer less than or equal to 2m+1, and $R^b$ is independently H, alkyl, hydroxyalkyl, or saccharide. The biomolecule may be an oligonucleotide, an antibody, a peptide having affinity for a biological receptor, or a sapphyrin molecule. A preferred texaphyrin is B2T2 and a preferred paramagnetic metal is Gd(III), Mn(II), Mn(III), Fe(III) or a trivalent lanthanide other than Ln(III), Lu(III) and Pm(III).

A preferred embodiment of the present invention is a method of radiation therapy for a host harboring a tumor comprising the steps of i) administering to the host a pharmaceutically effective amount of the Gd complex of B2T2,4,5-diethyl-10,23 -dimethyl-9,24-bis(3-hydroxypropyl)-16,17- (3-hydroxypropyloxy)-13,20,25,26,27-pentaazapentacyclo [20.2.1.1$^{3,6}$.1$^{8,11}$.0$^{14,19}$] heptacosa-1,3,5,7, 9,11(27),12,14(19),15,17,20,22(25),23-tridecaene; and ii) administering ionizing radiation to the host in proximity to the tumor.

Texaphyrin compounds, the structures of which were just described, are an aspect of the present invention as new compositions of matter. Specific embodiments of the texaphyrins are where $R_1$ is $CH_2CH_2CONCH(CH_2OH)_2$ and $R_5$ and $R_6$ are $OCH_3$; $OCH_2CH_2CH_2OH$; $OCH_2CH_2OH$; $O(CH_2CH_2O)_nCH_2CH_2OR'$, where n is an integer less than or equal to 10 and R' is H or $CH_3$; independently H or $CH_3$; or $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$. $R_1$ may be $CH_2CH_2CON(CH_2CH_2OH)_2$, $CH_2CH_2CONHCH_2CH(OH)CH(OH)CH(OH)CH(OH)CH_2OH$, $CH_2CH_2CH_2OH$, $CH_2CH_2CONHC_6H_{11}O_5$, $CH_2CH_2COOC_6H_{11}O_5$, and $R_5$ and $R_6$ are as just described.

Texaphyrins having different R groups on the B portion of the molecule, an R group on a ring nitrogen, or 4 or more hydroxyl groups on the tripyrrole portion of the molecule could all be useful for radiosensitization as well as imaging and localization. The hydroxylated texaphyrin B2T2 is a preferred texaphyrin for these methods, however, the potential of these further derivatives is further localization specificity that may be introduced by various substituents on the molecule. Any texaphyrin that binds to tumors whether hydroxylated or not may be used for radiosensitization.

A further embodiment of the present invention is a method for synthesizing an aromatic pentadentate expanded porphyrin analog having an alkyl group on a central tripyrrane ring nitrogen. The method comprises the steps of i) mixing, in an organic solvent, a nonaromatic pentadentate expanded porphyrin analog having an alkyl group on a central tripyrrane ring nitrogen, a Bronsted base and an oxidant; and ii) stirring at ambient temperature or heating the mixture at reflux for at least two hours. The nonaromatic pentadentate expanded porphyrin analog having an alkyl group on a central tripyrrane ring nitrogen is produced by condensation of a diformyltripyrrole having structure A; and an orthophenylenediamine having structure B:

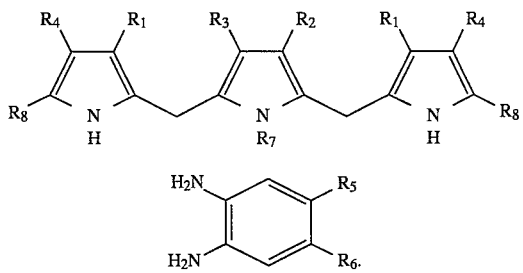

$R_1$, $R_2$, $R_3$, $R_4$, $R_5$ and $R_6$ are independently H, OH, alkyl, oxyalkyl, hydroxyalkyl, oxyhydroxyalkyl, saccharide, carboxyalkyl, carboxyamidealkyl, biomolecule or a couple to a biomolecule; $R_7$ is alkyl; $R_8$ is aldehyde, carboxylic acid or derivative thereof, and the molecular weight of any one of $R_1$, $R_2$, $R_3$, $R_4$, or $R_5$ is less than or equal to about 1000 daltons. In a preferred embodiment, $R_7$ is methyl, the Bronsted base is triethylamine, and the oxidant may be air saturating the organic solvent, oxygen, platinum oxide or 2,3-dichloro-5,6-dicyano-1,4-benzoquinone. The stirring or heating at reflux step comprises stirring or heating at reflux the mixture for at least 24 hours.

The organic solvent may comprise methanol and chloroform, methanol and benzene, or methanol and dimethylformamide.

BRIEF DESCRIPTION OF THE DRAWINGS

FIG. 1 shows a schematic representation of the reduced ($1_A$) and oxidized ($1_B$) forms of the free-base "texaphyrin" and a representative five coordinate cadmium complex ($1_C$) derived from this "expanded porphyrin".

$24_A$ is 4,5-dimethoxy-1,2-phenylenediamine, $24_B$ is 4,5-dimethyl-1, 2-phenylenediamine, $24_C$ is 1,2-diamino-4,5-bis((3'-hydroxyethyl)oxy)benzene, $24_D$ is 1,2-diamino-4,5-bis((3'-hydroxypropyl)oxy)benzene, $24_E$ is the 4,5-bis(polyethylene glycol monomethyl ether) substituted derivative of 1,2-o-phenylenediamine, and $24_F$ is the 4,5-bis(polyethylene glycol) substituted derivative of 1,2-o-phenylenediamine.

In $24_E$ and $24_F$, n is an integer less than or equal to 10.

Figure 25A:
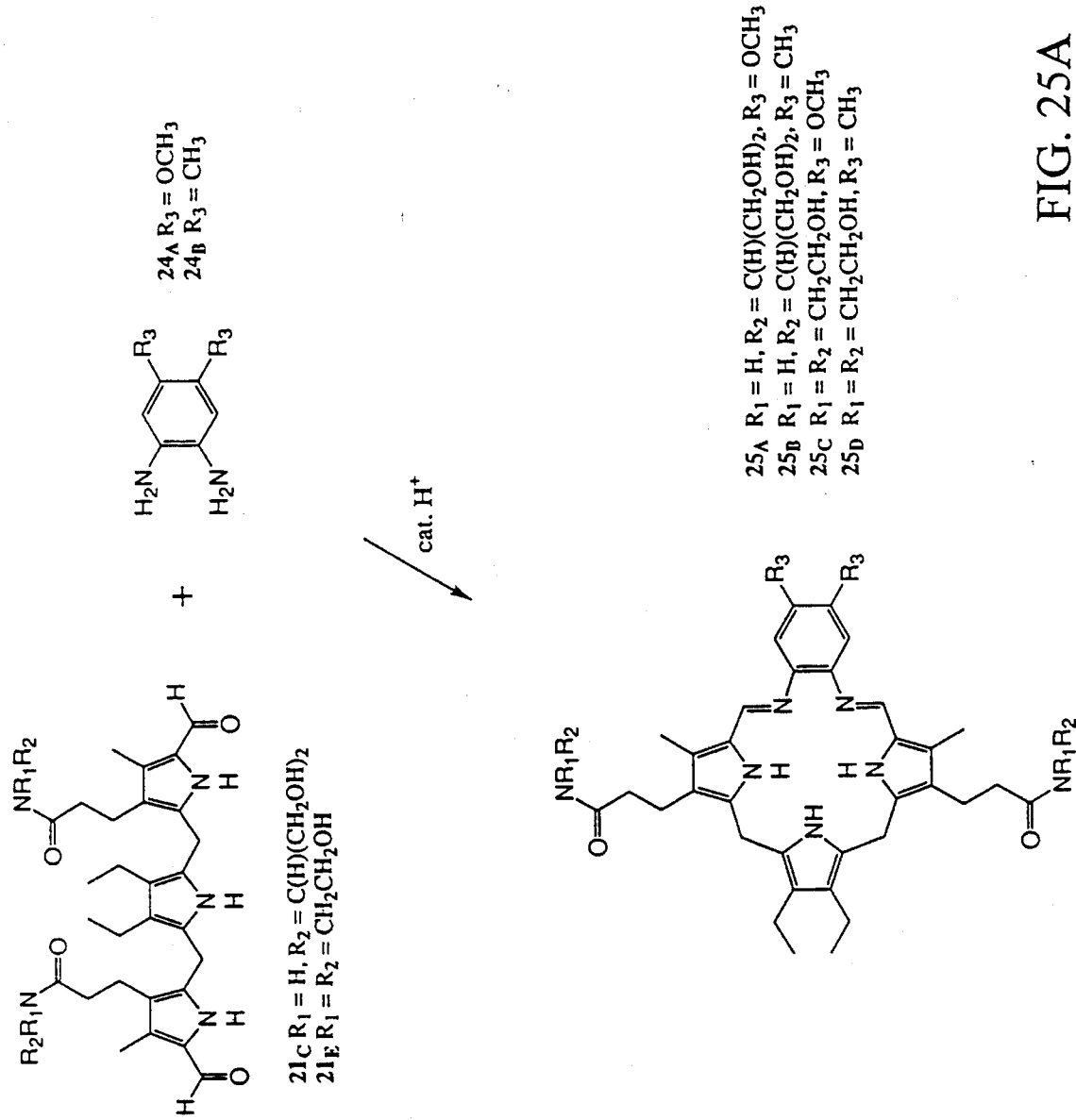
Figure 25B:
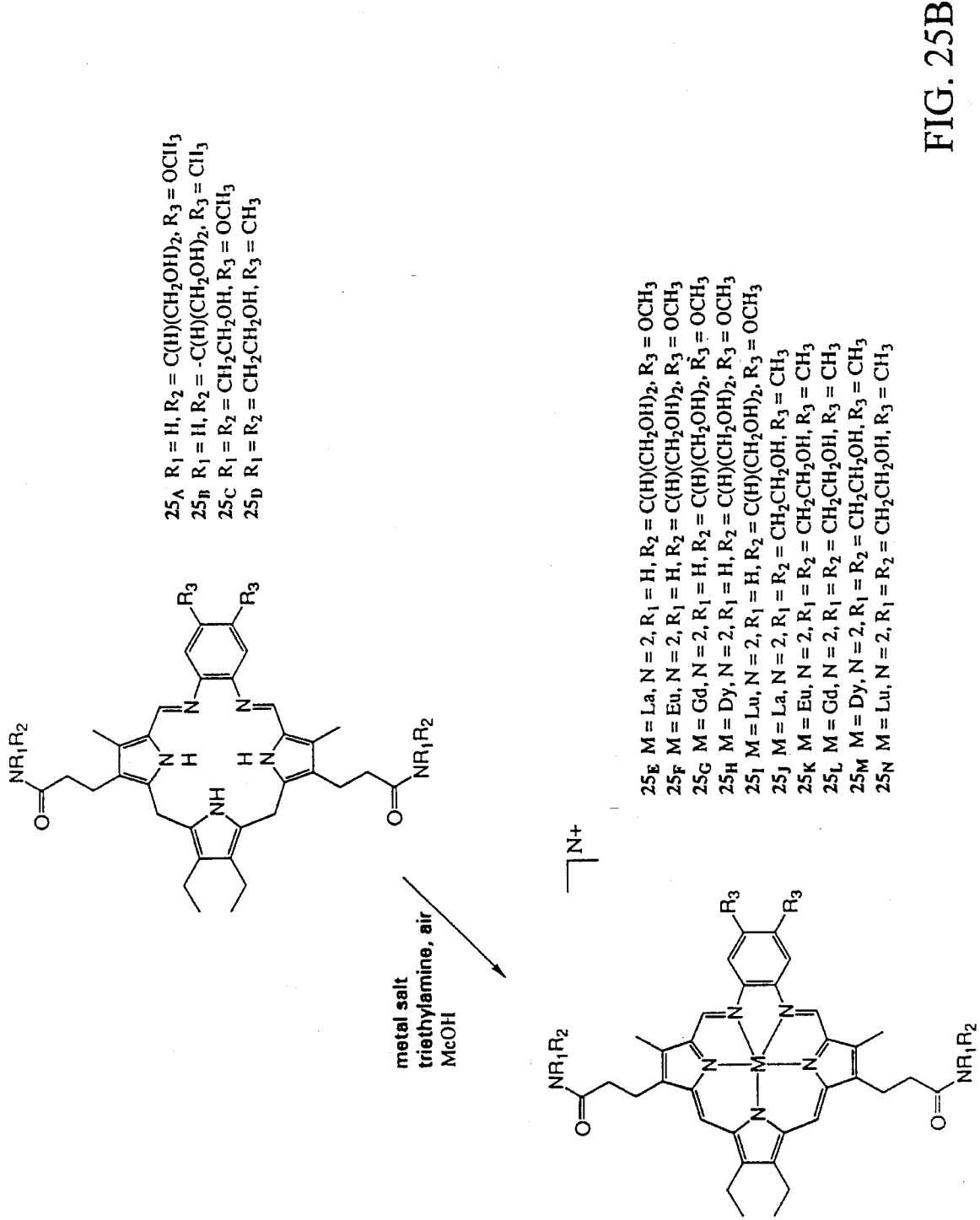

FIGS. 25A and 25B summarize the synthesis of T4 macrocycles.

Figure 26A:
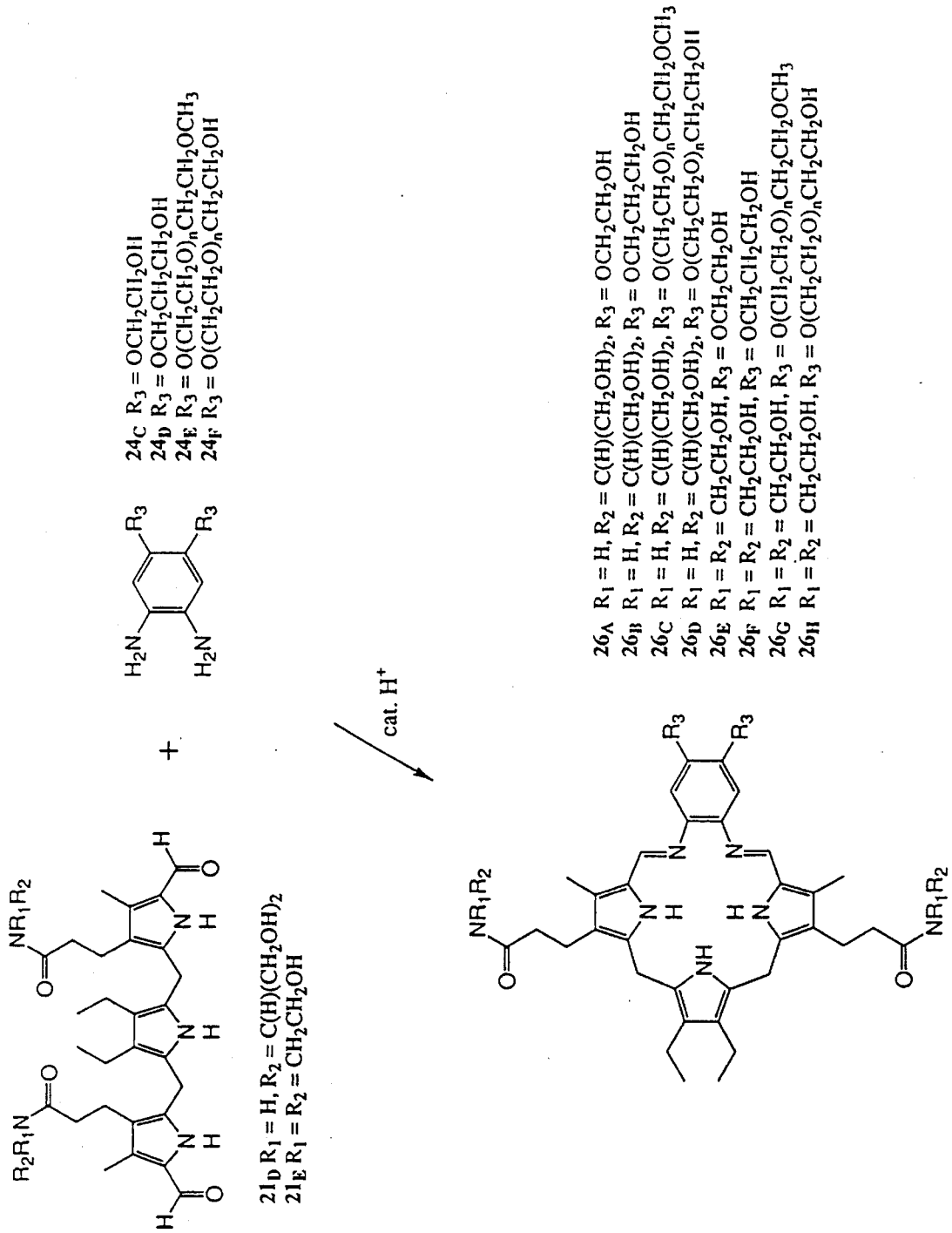
Figure 26B:
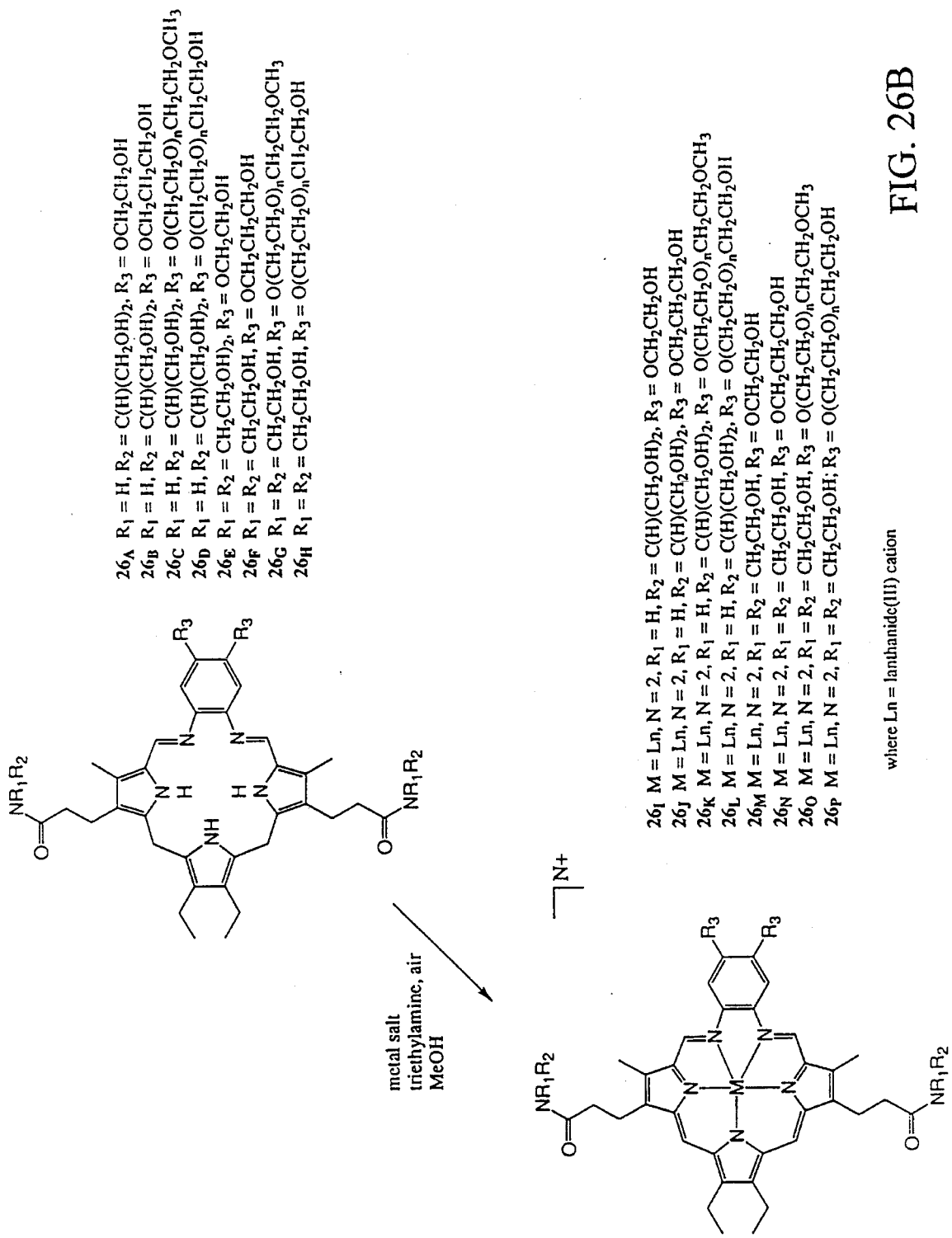

FIGS. 26A and 26B summarize the synthesis of T2, T4 and T6 macrocycles.

Figure 27A:
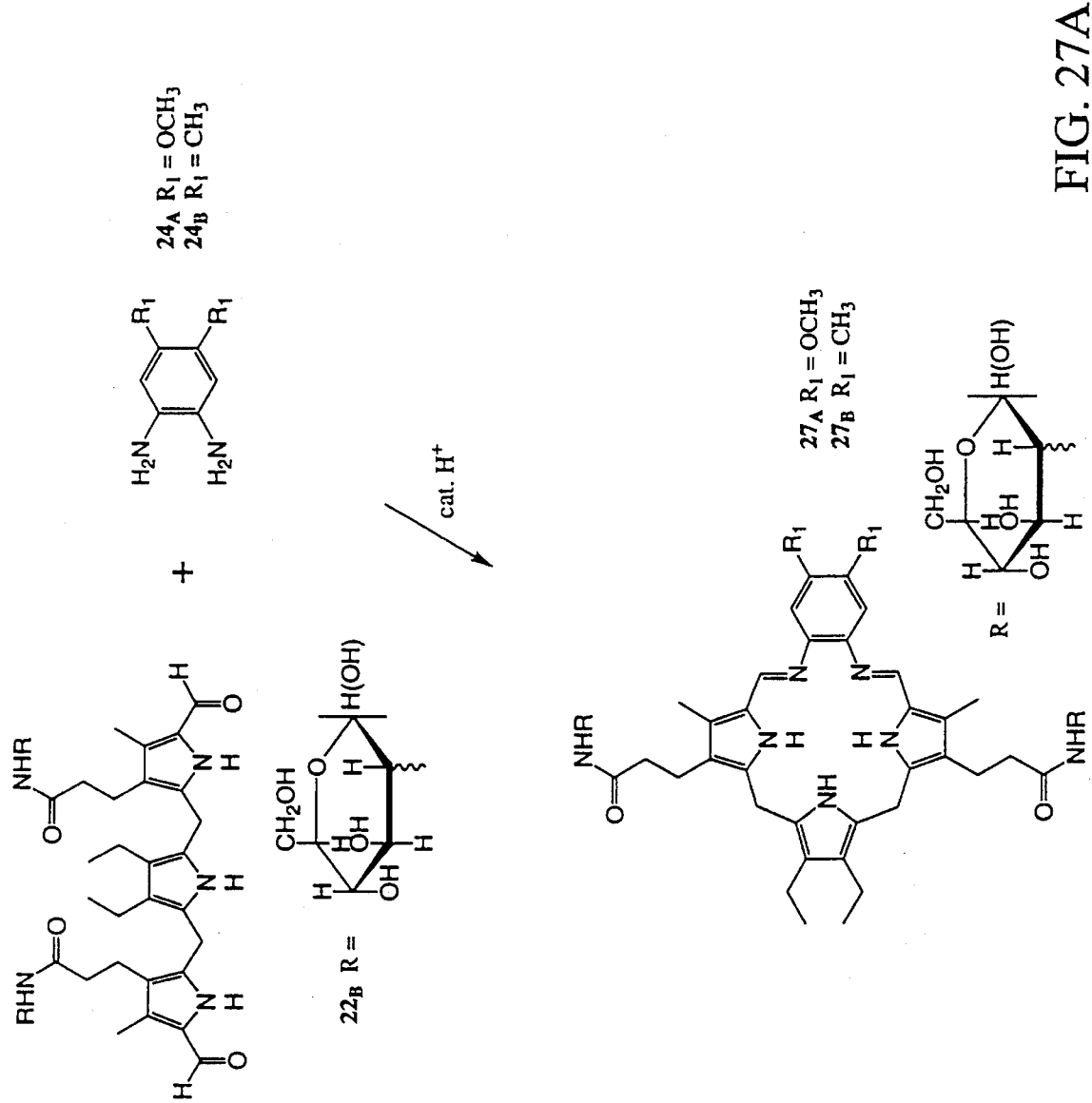
Figure 27B:
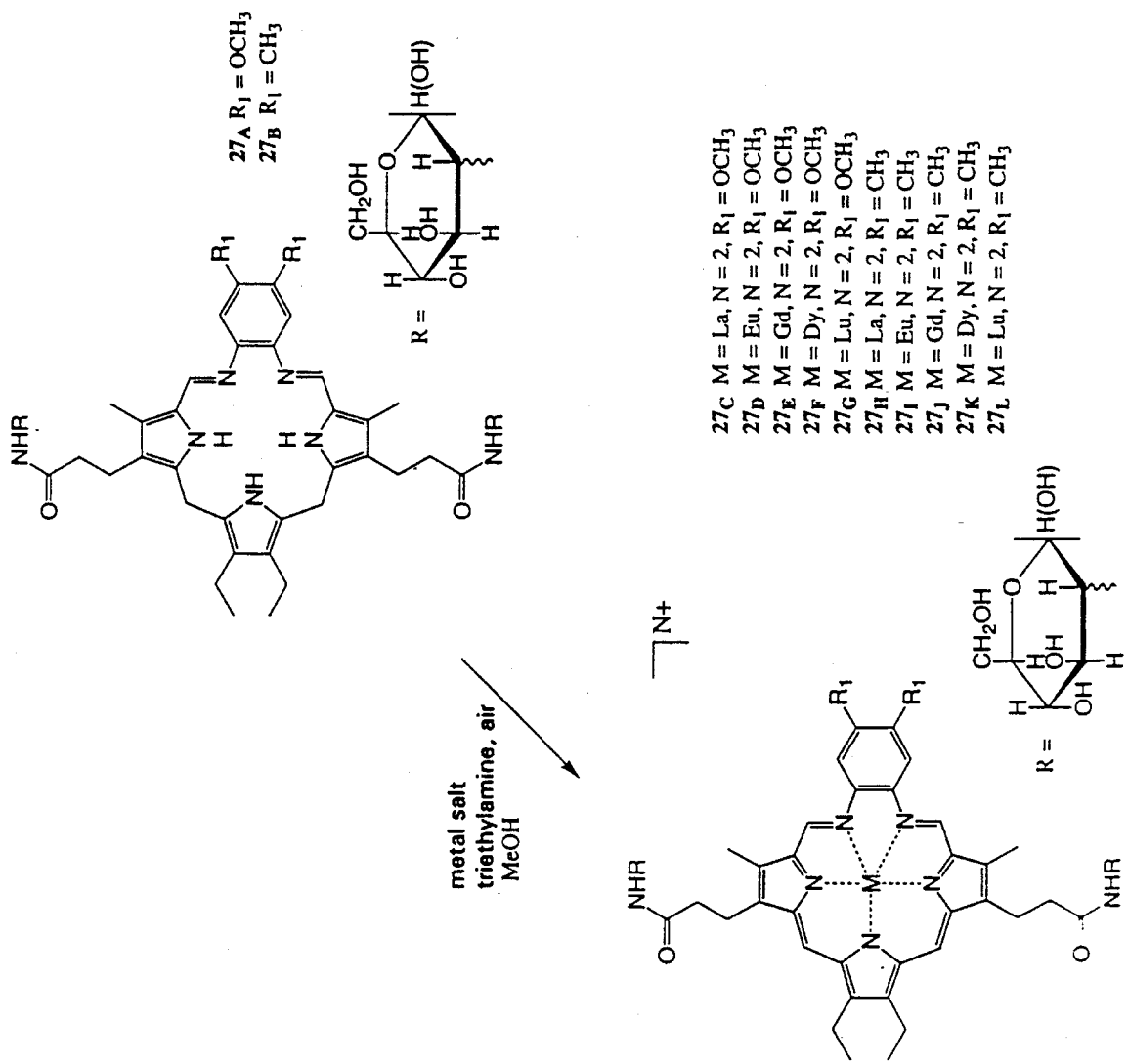

FIGS. 27A and 27B summarize the synthesis of T8–T10 macrocycles.

Figure 28A:
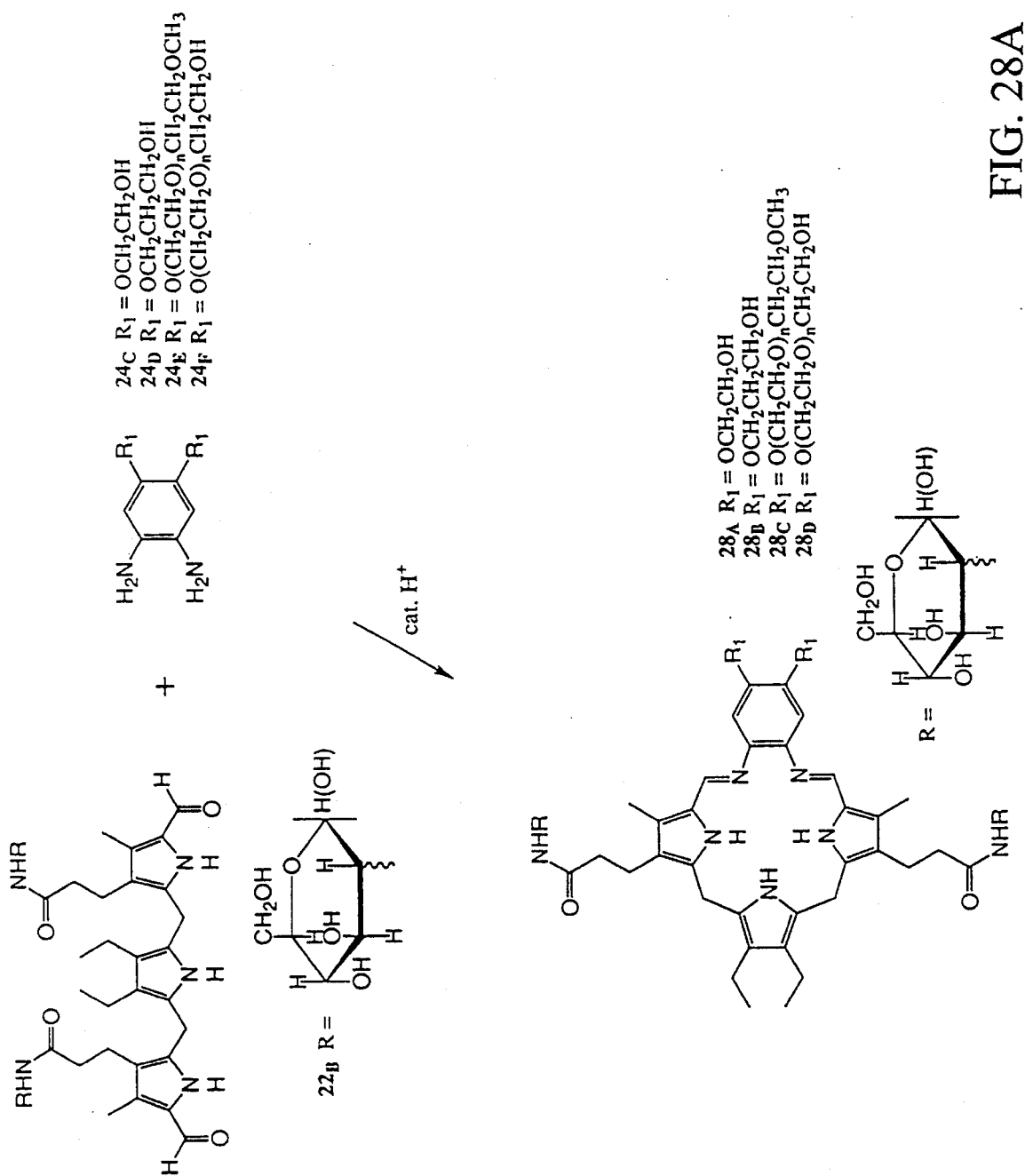
Figure 28B:
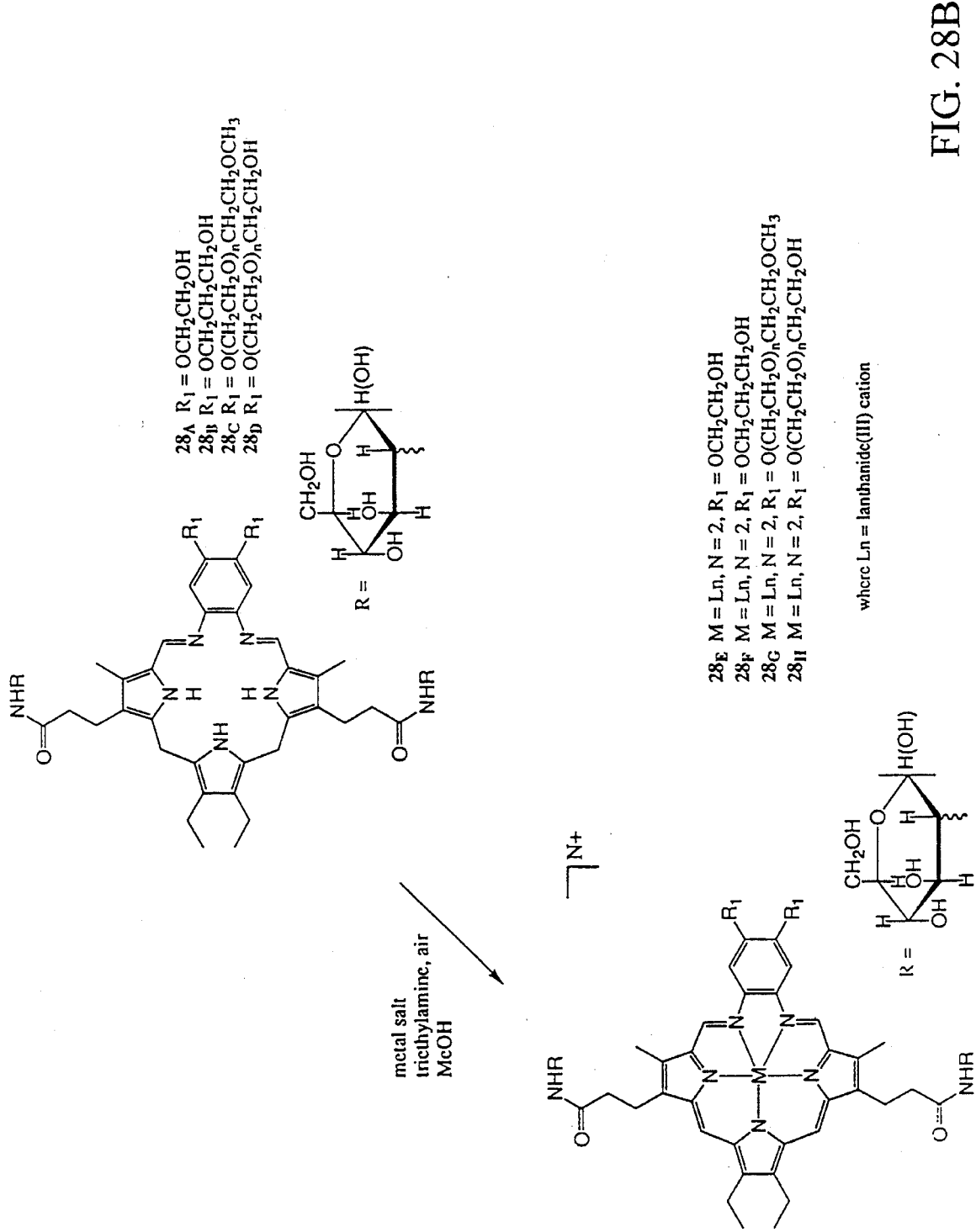

FIGS. 28A and 28B summarize the synthesis of T8–T12 macrocycles.

Figure 29A:
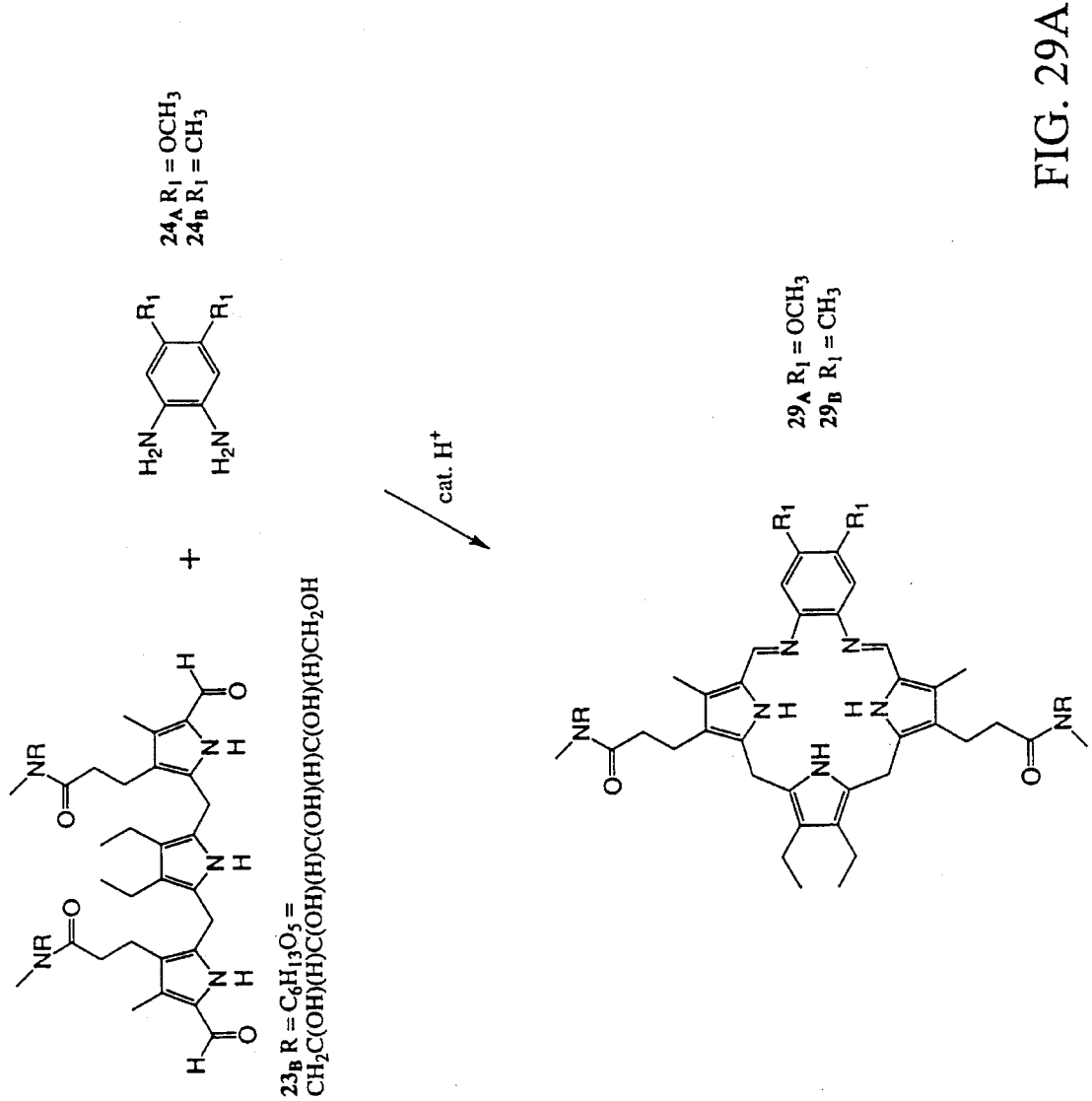
Figure 29B:
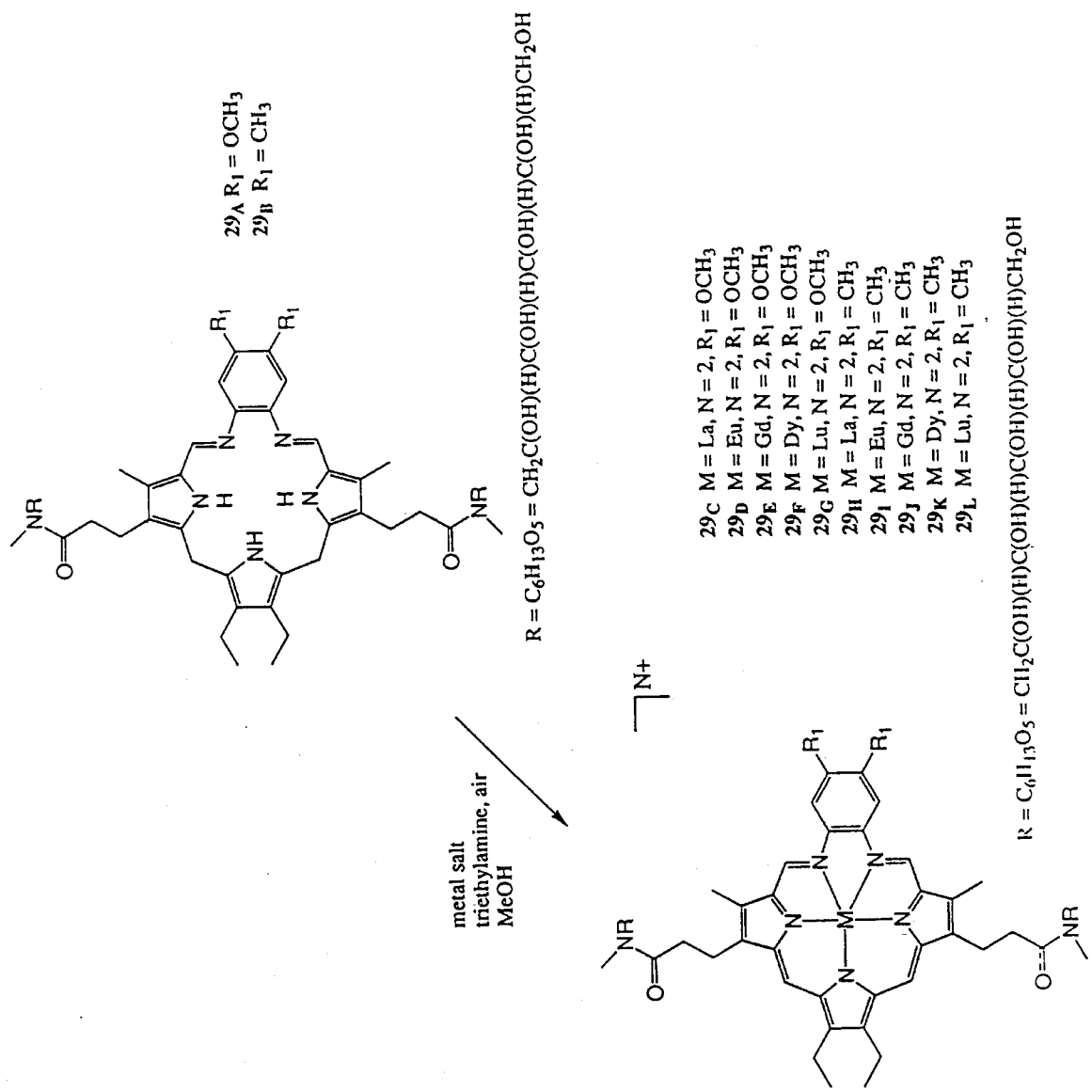

FIGS. 29A and 29B summarize the synthesis of T8–T10 macrocycles.

Figure 30A:
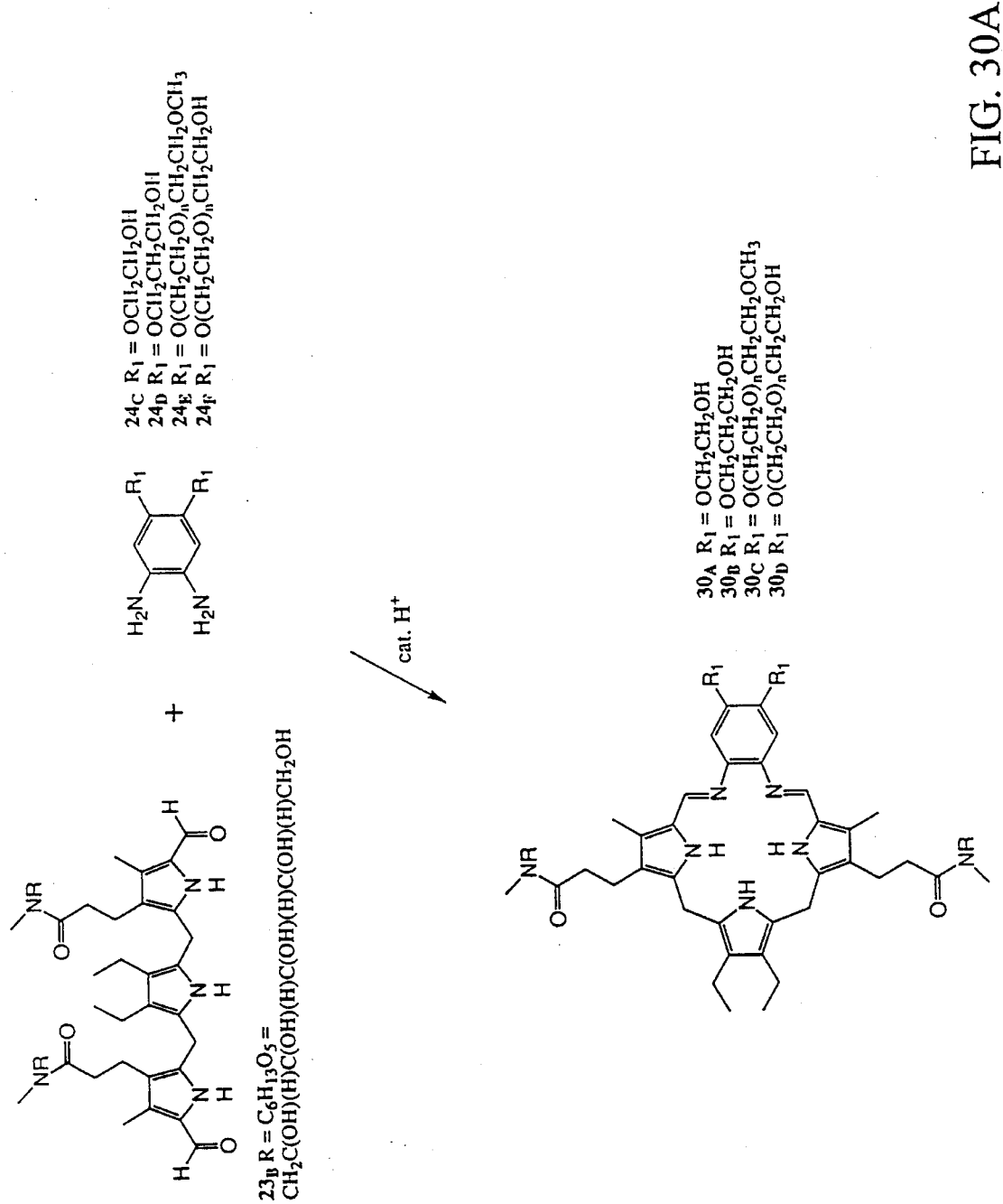
Figure 30B:
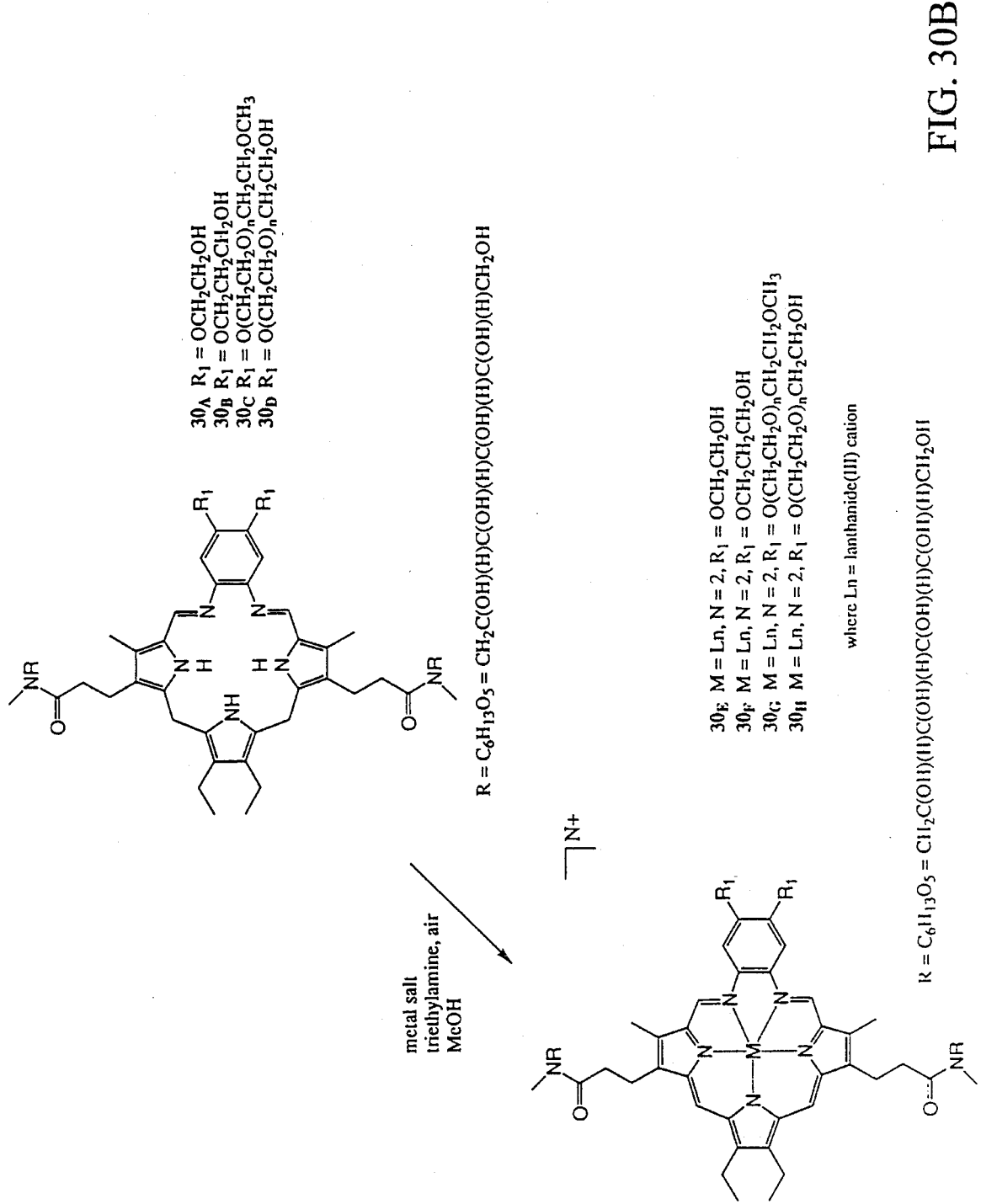

FIGS. 30A and 30B summarize the synthesis of T8–T12 macrocycles.

Figure 31:
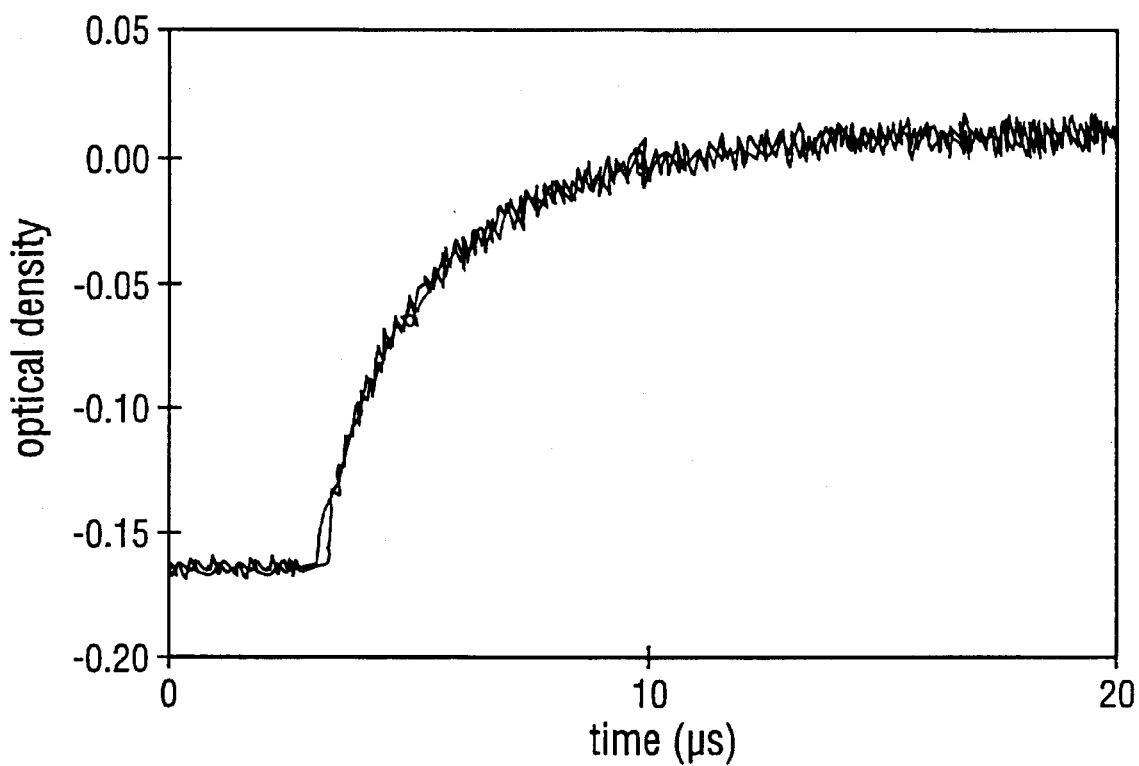

FIG. 31 shows pulse radiolysis in aqueous isopropanol. The optical density is plotted versus time in μseconds for the formation of the gadolinium texaphyrin anion, GdTX⁻·. Only reducing radicals are present in isopropyl alcohol since the proton removed from isopropyl alcohol combines with the oxidizing radical HO· to form water.

Figure 32A:
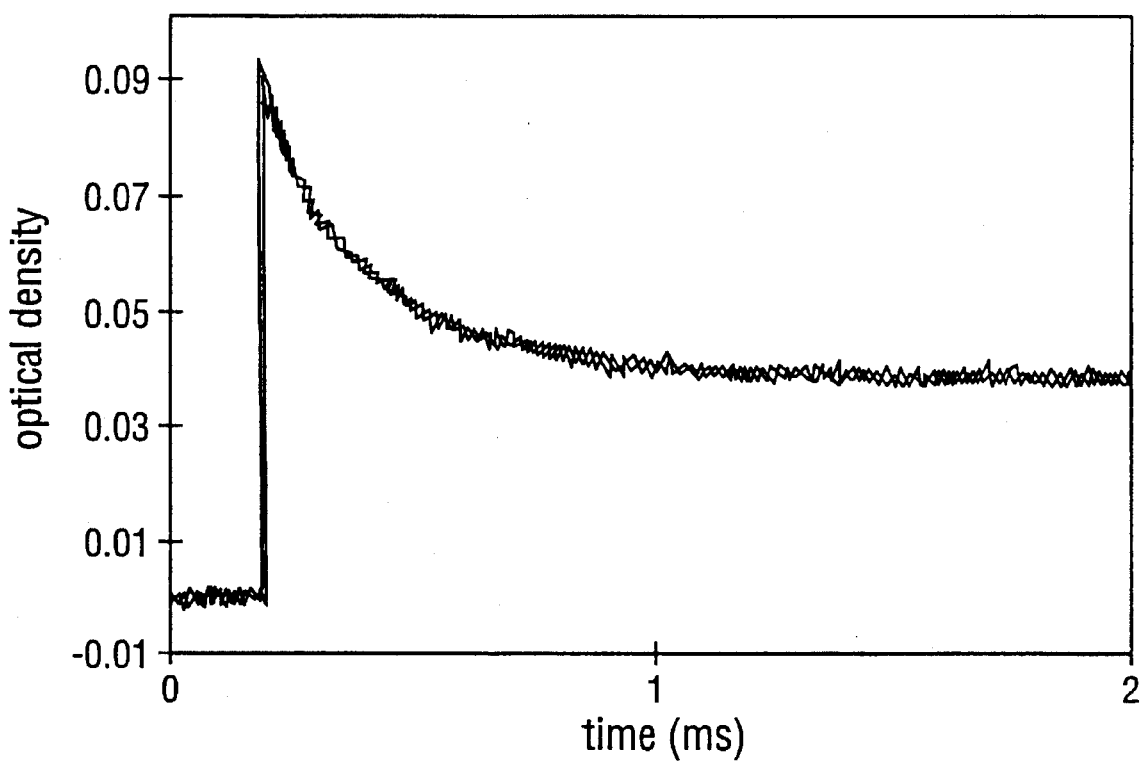
Figure 32B:
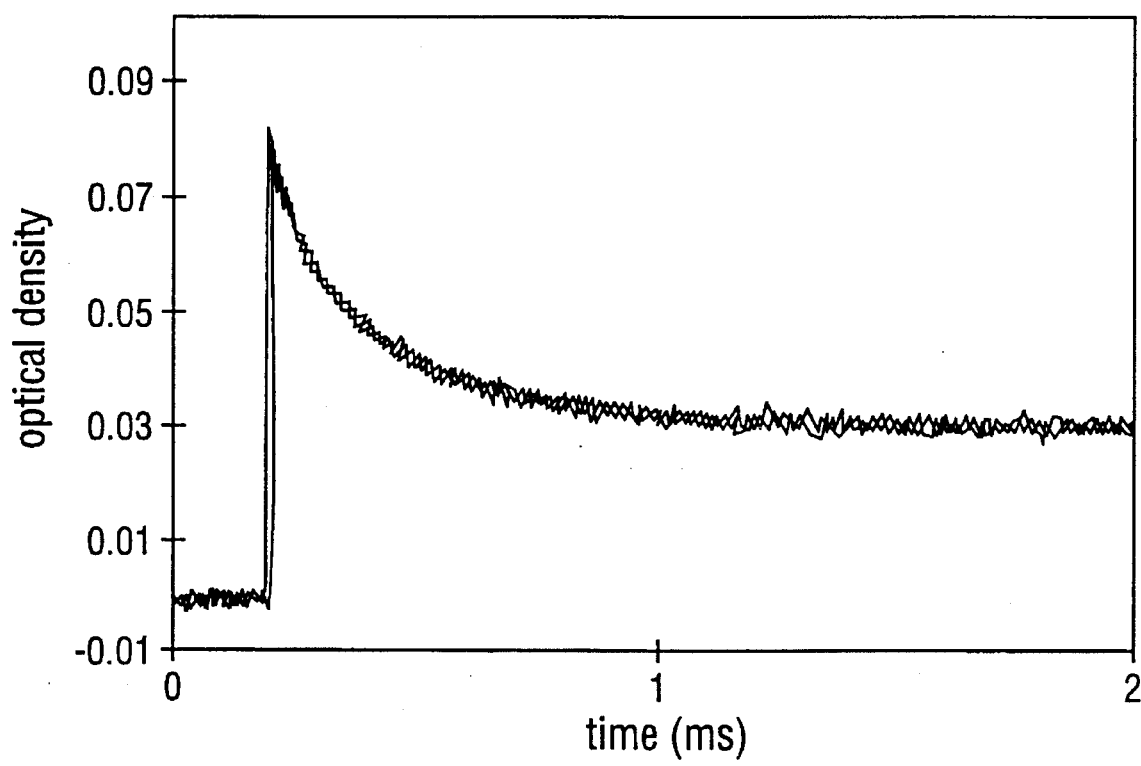

FIGS. 32A and 32B show the decay of the anion formed in FIG. 31 versus time in mseconds. The plot in 32A demonstrates that the anion has a long half life which is not affected by the presence of oxygen as shown in 32B. These data indicate that the TXP anion has a lower reduction potential than oxygen and therefore does not pass its electrons to oxygen.

Figure 33:
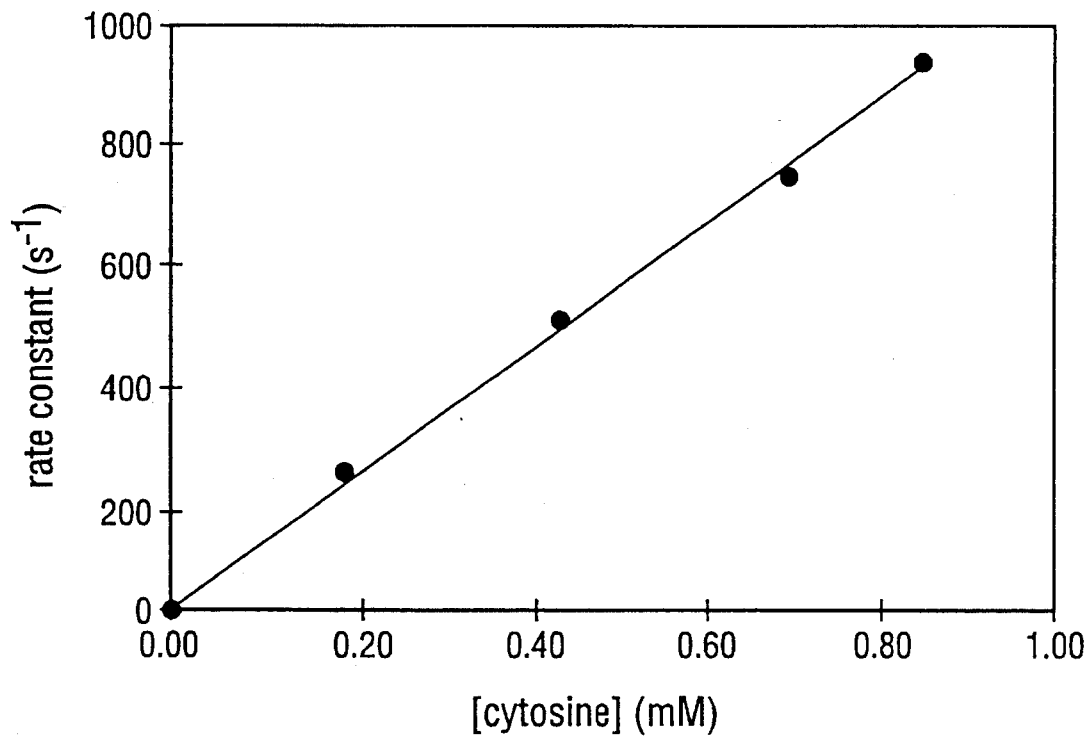

FIG. 33 shows the rate constants for the covalent modification of cytosine by the texaphyrin radical, GdTx(H·). These data indicate that the texaphyrin radical, while relatively stable, is nevertheless reactive and will cause damage to neighboring molecules.

Figure 34:
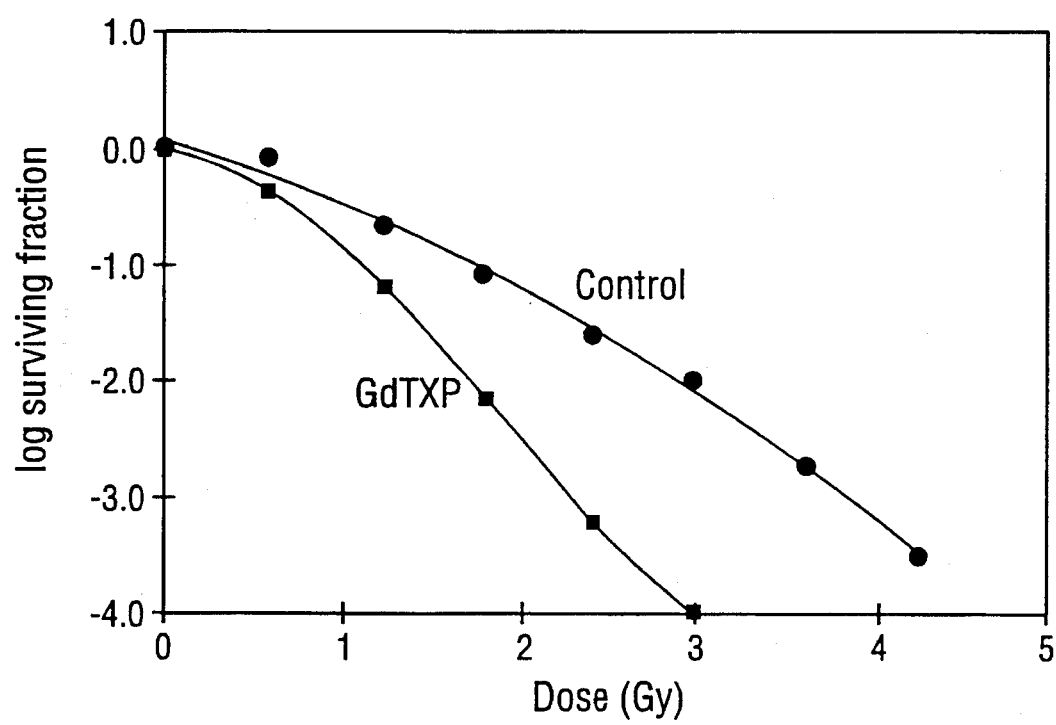

FIG. 34 shows the killing of mouse L1210 cells versus dose of radiation (in Grays) in the presence and absence of 20 μM GdTXP. The sensitizer enhancement ratio is 1.62.

Figure 35:
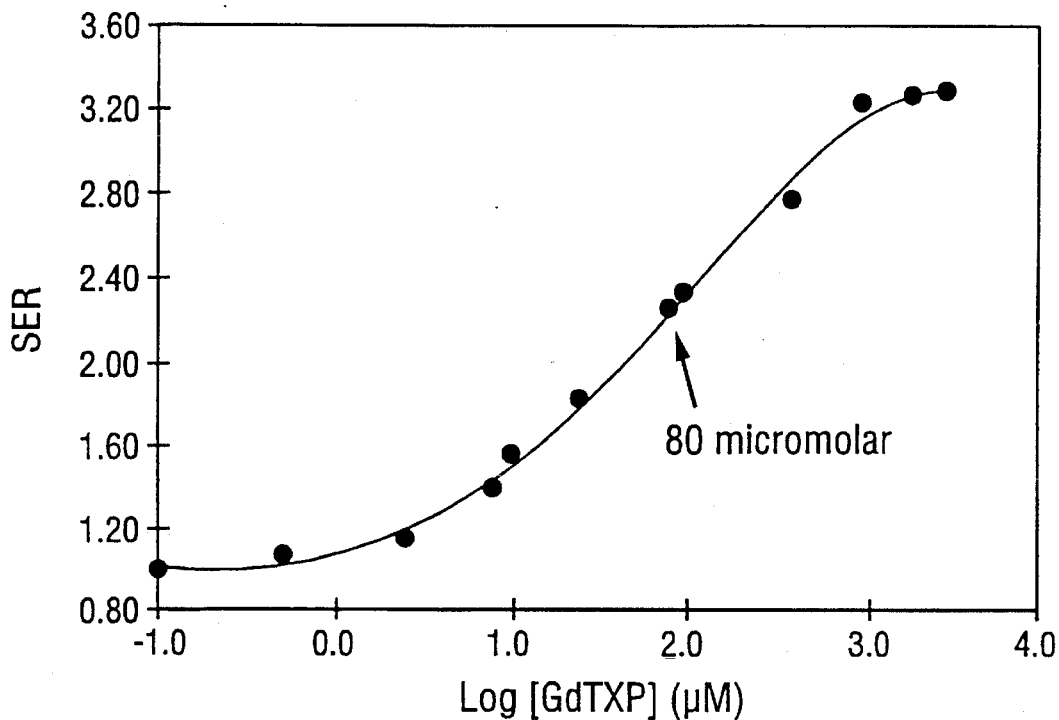

FIG. 35 shows the effect of GdTXP on L1210 cell kill. Sensitizer enhancement ratios are plotted versus concentration of GdTXP. An SER greater than 1.5 is clinically significant. These data indicate that the effectiveness of GdTXP as a sensitizer increases with the concentration achieved.

Figure 36:
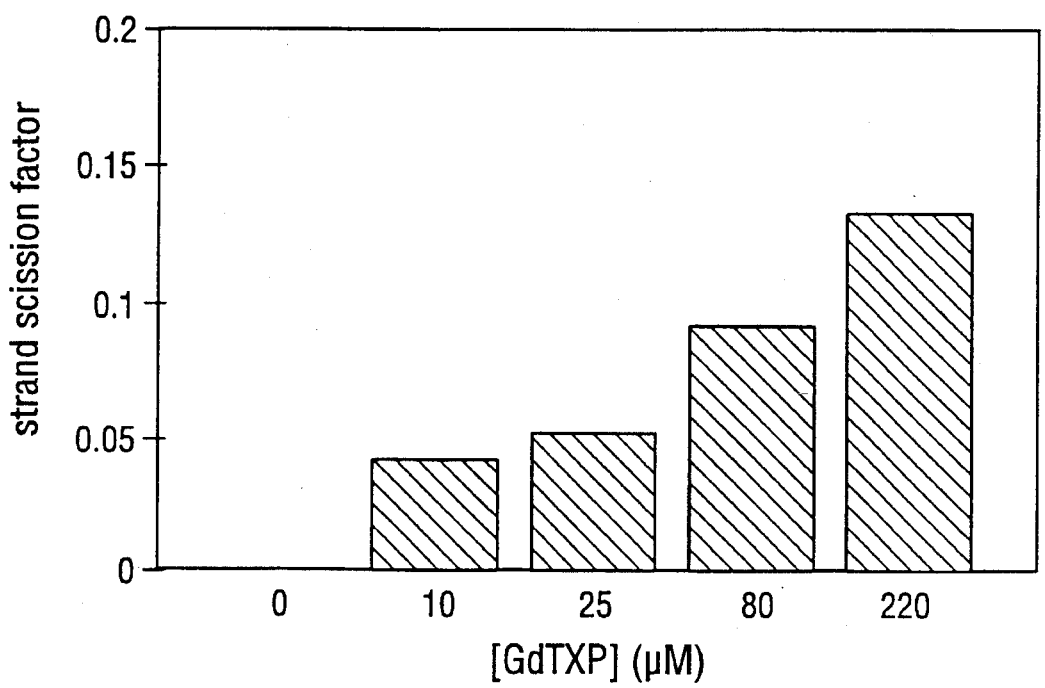

FIG. 36 shows the effect of GdTXP on nucleic acid strand scission under radiolysis at 25 grays. L1210 cells were exposed to GdTXP at the indicated concentrations, lysed and the nucleic acid material passed through a size selection filter.

FIGS. 37A, 37B and 37C show axial MRI scans of rabbit thigh muscle bearing a transplanted V2 carcinoma before (37A), 30 minutes (37B) and 3 hours (37C) after the administration of 5 μmol GdTXP (acetate)₂ per kg body weight. The pulsing sequences used were conventional spin echo sequences TR/TE=300/15, 16 Khz., 3 mm slice thickness and 256×192 matrix, 2 NEX, saturation inferiorly and superiorly with no phase rap.

DETAILED DESCRIPTION OF THE PREFERRED EMBODIMENTS

The present invention involves the use of texaphyrins, in particular, hydroxy-substituted texaphyrins for localization, radiosensitization, radiation therapy and photodynamic tumor therapy. More particularly, the invention demonstrates enhanced cytotoxicity from radiation and enhanced nucleic acid strand scission in the presence of a gadolinium texaphyrin complex. Examples 1–9 describe the synthesis of texaphyrins. Examples 10–14 describe the use of texaphyrins for imaging, radiosensitization, radiation therapy and photodynamic tumor therapy.

The introduction of hydroxy substituents on the B (benzene ring) portion of the texaphyrin molecule is accomplished by their attachment to phenylenediamine in the 4 and 5 positions of the molecule. The introduction of hydroxy substituents on the T (tripyrrole) portion of the molecule is accomplished by appropriate functionalization of the alkyl substituents in the 3 and/or 4 positions of the pyrrole rings at a synthetic step prior to condensation with the substituted phenylenediamine. Standard deprotection methodology such as ester hydrolysis may be used to unmask the free hydroxyl substituents. These derivatives exhibit significant solubility in aqueous media, up to 1 mM or better, yet they retain affinity for lipid rich regions which allows them to be useful in biological environments.

Divalent and trivalent metal complexes of texaphyrins are by convention shown with a formal charge of N⁺, where N=1 or 2, respectively. It is understood by those skilled in the art that the complexes described in the present invention may have one or more additional ligands providing charge neutralization and/or coordinative saturation to the metal ion. Such ligands include chloride, nitrate, acetate, and hydroxide, among others.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

Synthesis of Compounds $1_A$–$1_C$

Figure 2A:
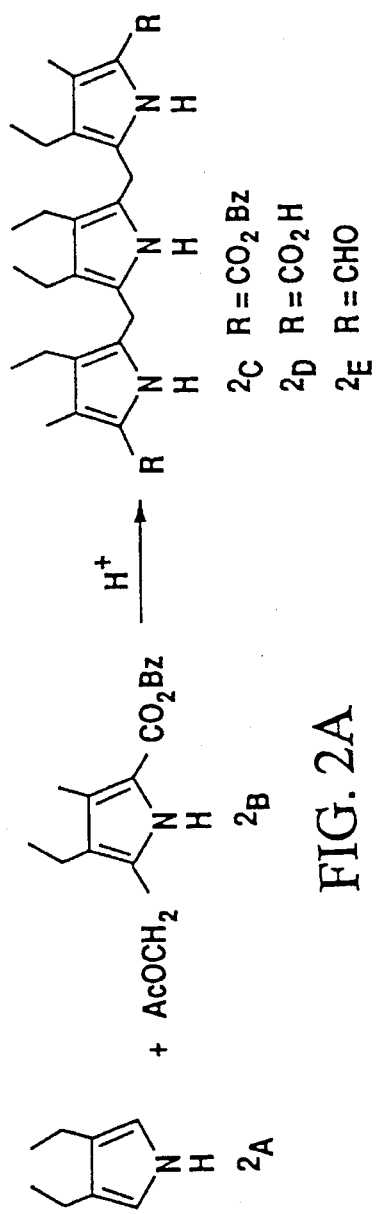
FIG. 2 schematically summarizes the synthesis of texaphyrin ($2_G$ also designated $1_B$ in FIG. 1).
Figure 2B:
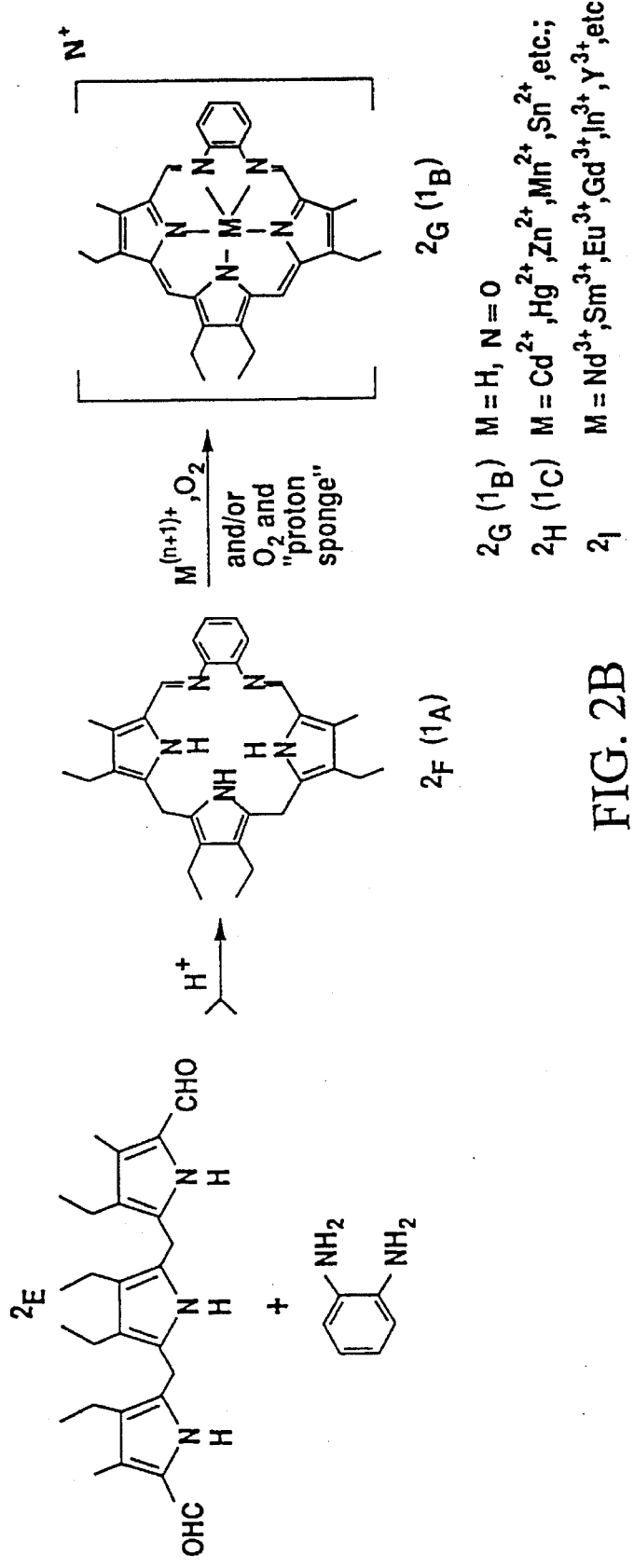
Figure 3B:
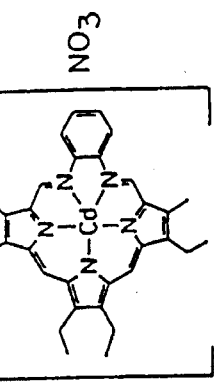
FIG. 3 shows $^1H$ NMR spectrum of $1_C \cdot NO_3$ in $CDCl_3$. The signals at 1.5 and 7.26 ppm represent residual water and solvent peaks respectively.
Figure 3A:
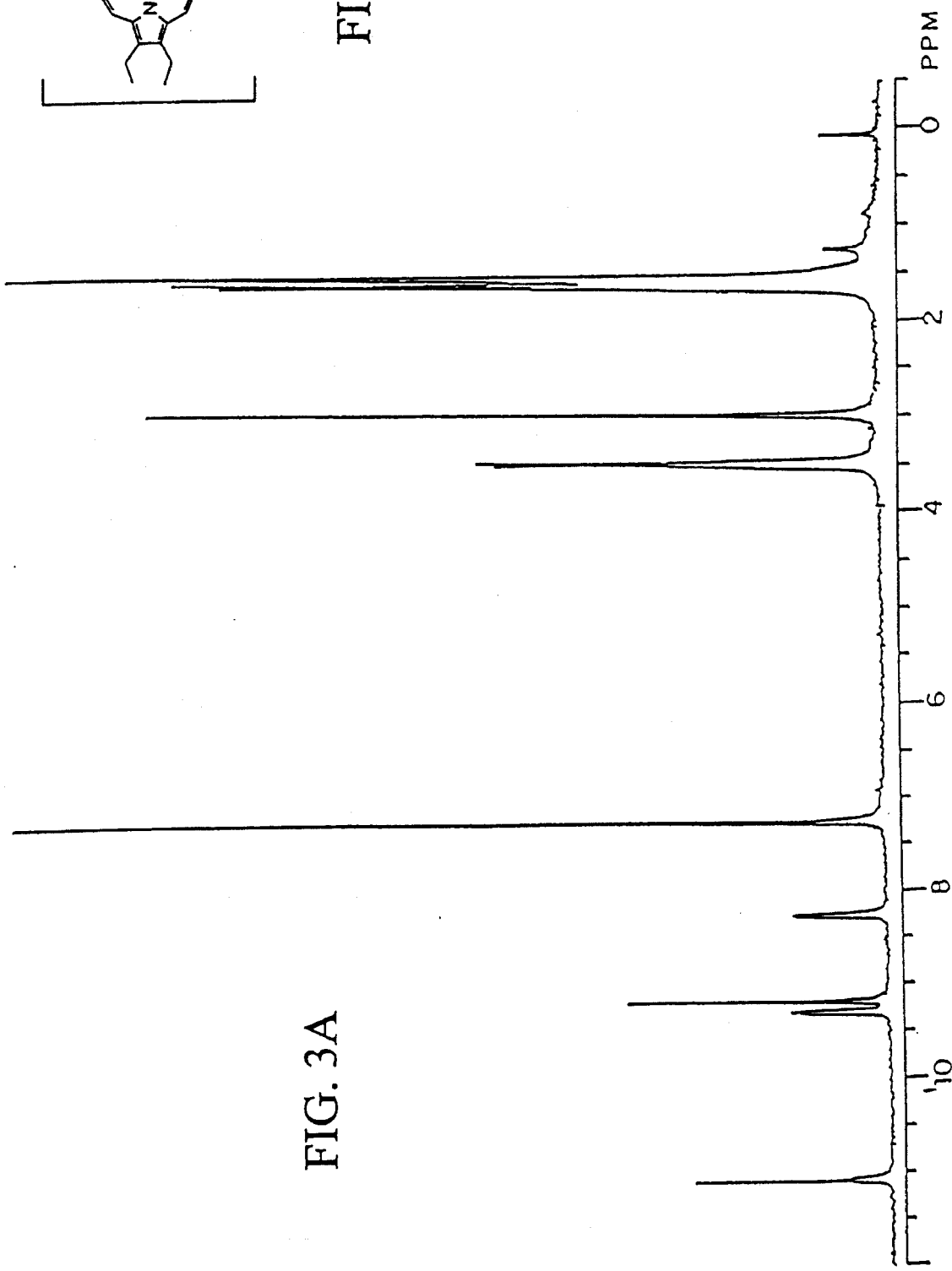
Figure 4B:
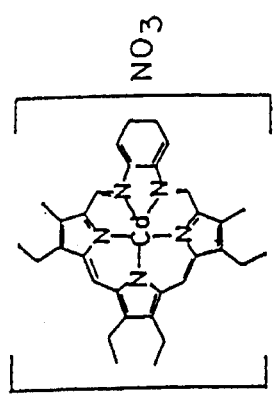
FIG. 4 shows a UV-visible spectrum of $1_C \cdot NO_3$ $1.50 \times 10^{-5}M$ in $CoCl_3$.
Figure 4A:
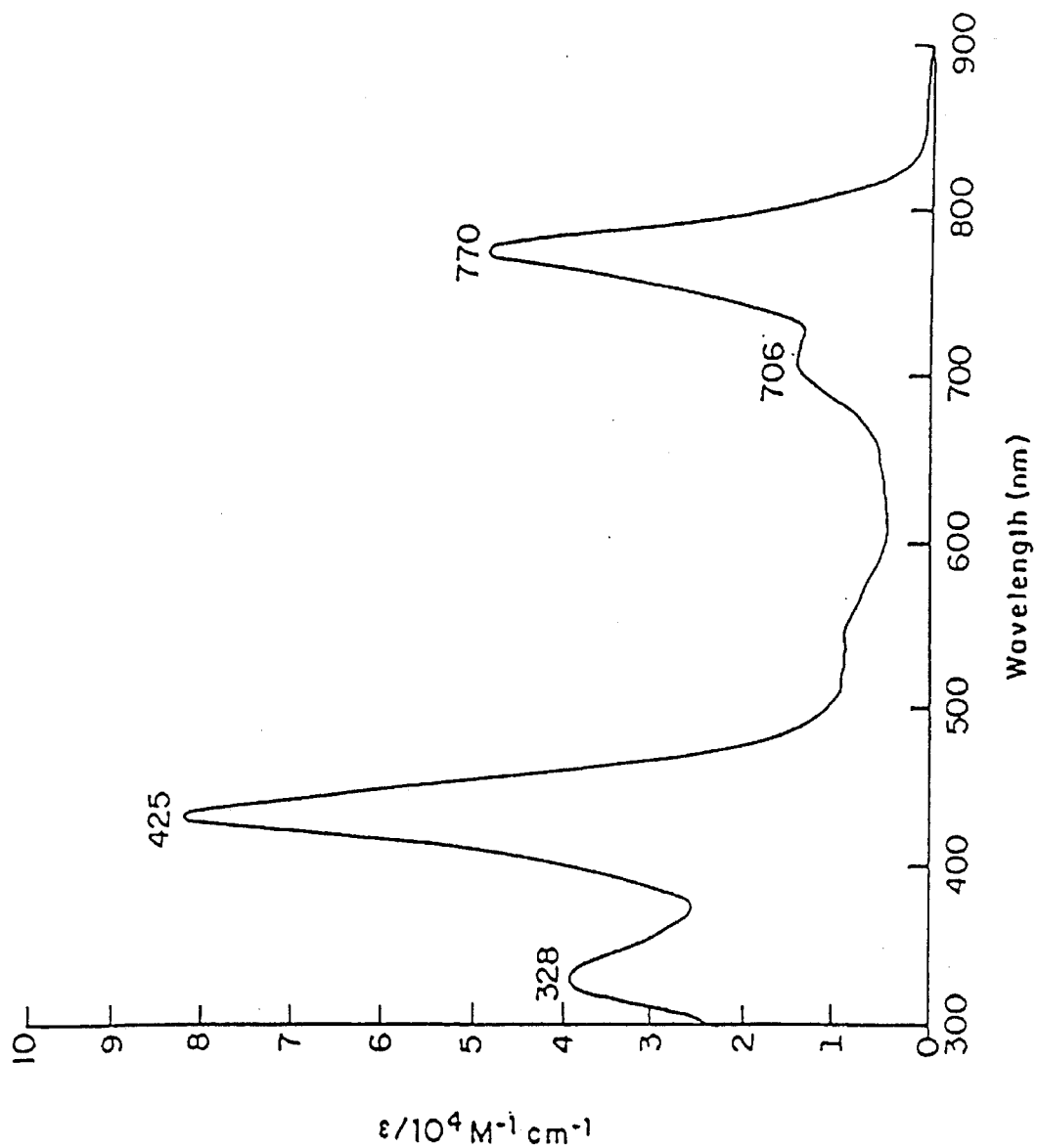
Figure 5A:
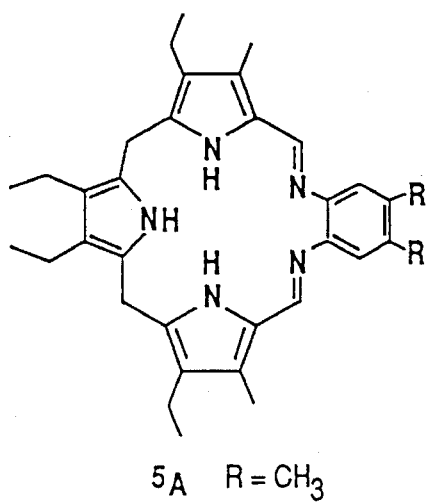
FIG. 5 shows metal complexes and derivatives ($5_A$–$5_E$) of texaphyrin macrocycles.
Figure 5B:
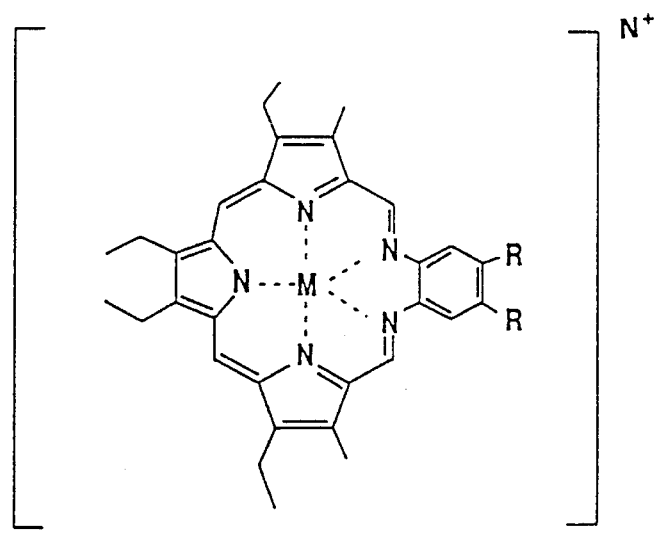

This example describes the synthesis of compounds depicted in FIGS. 1 and 2; the nonaromatic methylene-bridged macrocycle 1A, the expanded porphyrin named "texaphyrin" $1_B$ and the nitrate salt of the cadmium (II) complex $1_C$.

All solvents and reagents were of reagent grade quality, purchased commercially, and used without further purification. Sigma lipophilic Sephadex (LH-20-100) and Merck type 60 (230–400 mesh) silica gel were used for column chromatography. Melting points were recorded on a Mel-temp Laboratory Devices capillary apparatus and are uncorrected.

2,5-Bis[[5-(benzyloxycarbonyl)-3- ethyl-4-methylpyrrol-2-yl]methyl]-3,4-diethylpyrrole ($2_C$, FIG. 2) . 3,4-Diethylpyrrole ($2_A$, FIG. 2) (0.6 g, 4.9 mmol) , benzyl 5-(acetoxymethyl)-3 -methyl-4-ethyl-pyrrole-2-carboxylate ($2_B$, FIG. 2) (2.5 g, 7.9 mmol), and p-toluenesulfonic acid (0.15 g) were dissolved in 60 mL of absolute ethanol and heated at 60° C. for 8 h under nitrogen. The resulting suspension was reduced in volume to 30 mL and placed in the freezer for several hours. The product was then collected by filtration, washed with a small amount of cold ethanol, and recrystallized from dichloromethane-ethanol to afford a white powder (2.07 g, 82%): mp 211° C. NMR spectra and high resolution mass spectral data were obtained as described.

2,5-Bis[[(3-ethyl-5-formyl-4-methylpyrrol-2-yl)methyl]-3,4-diethylpyrrole ($2_E$, FIG. 2). The above diester ($2_C$) (4.5 g, 7.1 mmol) was dissolved in 500 mL of dry THF containing 1 drop of triethylamine and hydrogenated over 5% palladium-charcoal (250 mg) at 1 atm $H_2$ pressure until the reaction was deemed complete by TLC. The catalyst was separated and the solution was taken to dryness on the rotary evaporator. Recrystallization from dichloromethane-hexane yielded $2_D$ (3.2 g, quantitative) as a white powder which quickly develops a red hue upon standing in air: mp 111°–115° C. dec. The above diacid (3 g, 6.6 mmol) was dissolved in 5 mL of freshly distilled trifuoroacetic acid and heated at reflux for 5 min under nitrogen and allowed to cool to room temperature over the course of 10 min. The above heating and cooling sequence was repeated once more and the resulting dark oil was then cooled in an ice-salt bath. Freshly distilled triethylorthoformate (5 mL) was then added dropwise with efficient stirring. After 10 min the solution was poured into 300 mL of ice water and let stand 30 min. The dark red precipitate was collected by filtration and washed well with water. Ethanol (ca. 50 mL) was then used to wash the precipitate from the filter funnel into 350 mL of 10% aqueous ammonia. The resulting yellow suspension was stirred well for an hour and then extracted with dichloromethane (5×150 mL). The dichloromethane extracts were washed with water, dried over $MgSO_4$, and evaporated to dryness on the rotary evaporator to give 2, as an off-white mass. Two recrystallizations from chloroform-ethanol gave crystalline product (1.91 g, 68%) with mp 202°–203° C. NMR spectra and high resolution mass spectra data were obtained as described and are reported.

4,5,9,24 -Tetraethyl-10,23-dimethyl-13,20,25,26,27-pentaazapentacyclo[20.2.1.1$^{3,6}$.1$^{8,11}$.0$^{14,19}$]heptacosa-3,5,8,10, 12,14-(19),15,17,20,22,24-undecaene ($1_A$). A. Acid-Catalyzed Procedure. The diformyltripyrrane ($2_E$, FIG. 2) (105 mg, 0.25 mmol) and o-phenylenediamine (27 mg., 0.25 mmol) were dissolved, with heating, in a degassed mixture of 300 mL of dry benzene and 50 mL of absolute methanol. Concentrated HCl (0.05 mL) was then added and the resulting gold solution heated at reflux for 24 h under nitrogen. After cooling, solid K2CO3 (20 mg) was added and the solution filtered through $MgSO_4$. The solvent was then removed on the rotary evaporator and the resulting product dissolved in 50 mL of $CH_2Cl_2$ and refiltered (to remove unreacted $2_E$). Heptane (100 mL) was added to the filtrate and the volume reduced to 50 mL on the rotary evaporator whereupon the flask was capped and placed in the freezer overnight. The resulting white powder was then collected by filtration, washed with hexane, and dried in vacuo to yield $1_A$ (55 mg, 44%): mp 188°–190° C.

Metal Template Procedure. The diformyltripyrrane $2_E$ and o-phenylenediamine reactants were condensed together on a 0.25-mmol scale exactly as described above except that 1.0 equiv of either Pb(SCN)$_2$ (80 mg) or UO$_2$Cl$_2$ (85 mg) was added to the boiling solution at the outset of the reaction. Following workup as outlined above, 68 mg (69%) and 60 mg (61%) of $1_A$ were obtained respectively for the $Pb^{2+}$- and $UO^{2+}$-catalyzed reactions. The products produced in this manner proved identical with that prepared by procedure A.

NMR spectra and high resolution mass spectra data were obtained as described.

4,5,9,24-Tetraethyl-10,23-dimethyl-13,20,25,26,27-pentaazapentacyclo[20.2.1.1$^{3,6}$.1$^{8,11}$. 0$^{14,19}$] heptacosa-1,3,5,7, 9,11(27),12,14,16,18,20,22 (25),23-tridecaene, free-base "texaphyrin" $1_B$. Macrocycle $1_A$ (50 mg, 0.1 mmol) was stirred in methanol/chloroform (150 ml, v/v/2/1) in the presence of N, N, N', N'-tetramethyl-1,8 -diaminonaphthalene ("proton sponge") for one day at room temperature. The reaction mixture was then poured into ice water. The organic layer was separated and washed with aqueous ammonium chloride solution and then brine (a saturated solution of sodium chloride in water). Following concentration on a rotary evaporator, the crude material was purified by chromatography on SEPHADEX using first pure chloroform and then chloroform/methanol (v/v/10/1) as eluents. After several faster red bands were discarded, a dark green band was collected, concentrated in vacuo, and recrystallized from chloroform/n-hexane to give the sp$^2$ form of the ligand as a dark green powder in yields ranging from 3–12% with the better yields only being obtained on rare occasions. Spectral data are reported in patent application SN 07/771,393.

The preparation of complex $1_C$. NO$_3$ was as follows: the reduced sp$^3$ form of the macrocyclic compound ($1_A$) (40 mg, 0.08 mmol) was stirred with cadmium nitrate tetrahydrate (31 mg, 0.1 mmol) in chloroform/methanol (150 ml, v/v/= 1/2) for 1 day. The dark green reaction mixture was then concentrated and purified by chromatography on silica gel as described above. The resulting crude material was then recrystallized from chloroform/n-hexane to give analytically pure $1_C$. NO$_3$ in 27% yield. Under the reaction conditions both ligand oxidation and metal complexation take place spontaneously. Spectral data are reported in patent application SN 07/771,393.

EXAMPLE 2

Synthesis of compounds $5_A$–$5_E$.

All solvents and reagents were of reagent grade quality, purchased commercially, and used without further purification. Sigma lipophilic SEPHADEX (LH-20-100) and Merck type 60 (230–400 mesh) silica gel were used for column chromatography.

Compound $5_C$ is the metal adduct of ligand $5_A$ which was obtained in ca. 90% yield by condensing 1,2-diamino-4,5-dimethylbenzene with 2,5-Bis-(3-ethyl-5-formyl-4-methylpyrrol-2 -ylmethyl)-3,4-diethylpyrrole under acid catalyzed conditions identical to those used to prepare $1_A$. The sp$^a$ form of ligand $5_A$ (42 mg, 0.08 mmol) was stirred with gadolinium acetate tetrahydrate (122 mg, 0.3 mmol) and Proton Sponge™, N, N, N', N'-tetramethyl-1,8-diaminonaphthalene (54 mg, 0.25 mmol) in chloroform/methanol (150 ml, v/v 1/2) for one day at room temperature. The dark green reaction mixture was concentrated under reduced pressure and chromatographed through silica gel (25 cm.× 1.5 cm.) which was pretreated with chloroform/triethylamine (50 ml, v/v 25/1). Chloroform/triethylamine (25/1) and chloroform/methanol/triethylamine 25/2.5/1 v/v) was used as eluents. A dark red band was first collected followed by two green bands. The last green band, which showed a clear aromatic pattern by UV/VIS, was concentrated and recrystallized from chloroform/n-hexane to give 14 mg (22%) of the Gd complex $5_C$.

Treatment of compound $5_A$ with Gd(OAc)$_3$, Eu(OAc)$_3$, and Sm(OAc)$_3$ under reaction and work-up conditions similar to those used to obtain $1_C$, then gave the cationic complexes $5_C$, $5_D$, and $5_E$, as their dihydroxide adducts, in 22%, 33%, and 37% yields respectively. As judged by the IR and microanalytical data, under the reaction and work up conditions, hydroxide anions serve to displace the acetate ligands presumably present following the initial metal insertion procedure.

EXAMPLE 3

Synthesis of texaphyrin derivative B2.

$^1$H and $^{13}$C NMR spectra were obtained on a General Electric QE-300 (300 MHz.) spectrometer. Electronic spectra were recorded on a Beckman DU-7 spectrophotometer in $CHCl_3$. Infrared spectra were recorded, as KBr pellets, from 4000 to 600 $cm^{-1}$ on a Nicolet 510P FT-IR spectrophotometer. Chemical ionization mass spectrometric analyses (CI MS) were made using a Finnigan MAT 4023. Low resolution and high resolution fast atom bombardment mass spectrometry (FAB MS) were performed with a Finnigan-MAT TSQ-70 and VG ZAB-2E instruments, respectively. A nitrobenzyl alcohol (NBA) matrix was utilized with $CHCl_3$ as the co-solvent. Elemental analyses were performed by Atlantic Microlab, Inc. Melting points were measured on a Mel-temp apparatus and are uncorrected.

Materials. All solvents and reagents were of reagent grade quality, purchased commercially, and used as received. Merck Type 60 (230–400 mesh) silica gel was used for column chromatography. Thin-layer chromatography was performed on commercially prepared Whatman type silica gel 60A plates.

1,2-bis((2-carboxy) ethoxy)-4,5-dinitrobenzene. $6_B$, FIG. 6; To a well stirred solution of o-bis((3-hydroxypropyl)oxy) benzene (5.0 g, 22 mmol) in 30 mL glacial acetic acid cooled to 15° C., 20 mL of concentrated nitric acid (70%) was added dropwise over a period of 15 minutes. The temperature was held below 40° C. by cooling and proper regulation of the rate of acid addition. After the addition, the yellow solution was stirred at room temperature for 15 minutes. Here, the solution was cooled again to 15° C. and 50 mL of fuming nitric acid (90%) was added dropwise over a period of 30 minutes. The orange solution was brought to room temperature and stirred for approximately 48 hours. After 48 hours, the reaction solution was checked by TLC, which displayed only one low Rf spot, the diacid. Therefore, the orange solution was poured onto 600 mL of ice in a 1 liter beaker. The precipitated dinitro product was filtered, washed with water (1000 mL) until free from acid and dried in vacuo for 24 hours. The crude product was recrystallized from acetone/n-hexanes to yield the diacid as fluffy yellow needles (4.20 grams, 55.2%). For the diacid: $^1$H NMR ($d_6$-acetone) δ: 2.87 (t, 4H, $OCH_2CH_2CO_2H$), 4.49 (t, 4H, $OCH_2CH_2CO_2H$), 7.71 (s, 2H, Ar-H), 9–10 (br s, 2H, $CO_2H$). $^{13}$C NMR (d6-acetone) δ: 33.76, 66.57, 109.85, 137.14, 152.06, 171.51. EI MS, m/z (rel. intensity): 346 (100))

1,2-bis((3-hydroxypropyl)oxy)-4,5-dinitrobenzene. $6_C$, FIG. 6. In a dry 500 mL round bottom flask, equipped with a 125 mL pressure equalized dropping funnel, 1,2bis((2-carboxy) ethoxy)-4,5-dinitrobenzene (5.0 g, 14.5 mmol) was dissolved in 50 mL dry THF (distilled over ketyl) and stirred at 0°–10° C. under nitrogen. To the resulting clear solution, 120 mL of BHs. THF (1M) was added dropwise over a period of 30 minutes. After the borane addition, the reaction mixture was stirred an additional 5 minutes at 10° C. and then it was brought up to room temperature. The formation of the diol product was followed by TLC and the reaction was deemed complete after approximately 2 hours. The borane solution was quenched by careful addition of 65 mL of absolute methanol (Careful: frothing occurs!). After stirring the yellow solution for 30 minutes, it was concentrated to a bright yellow solid on a rotary evaporator. The crude solid was dissolved in 200 mL ethyl acetate and washed with 4M sodium acetate (2×100 mL), water (2×100 mL) and then brine (50 mL). The organic layer was dried over $MgSO_4$ and concentrated to dryness on a rotary evaporator. The crude product was recrystallized from acetone/n-hexanes to afford 4.12 grams (90%) of orange needles. For the diol: mp 129°–130° C.; $^1$H NMR ($CDCl_3$) δ: 2.10 (p, $4_{H,}$ $OCH_2C_2CH_2OH$), 3.81 (t, 4H, $OCH_2CH_2CH_2OH$), 4.28 (t, 4H, $OC_2CH_2CH_2OH$), 7.41 (s, 2H, Ar-H). $^{13}$C NMR ($d_6$-acetone) δ: 32.52, 58.50, 67.81, 107.88, 137.03, 152.47. EI MS, m/z (rel. intensity): 316 (100); HRMS (M$^+$) 316. 0914 (calcd. for $C_{12}H_{16}N_2O_8$: 316.0907).

Figure 6:
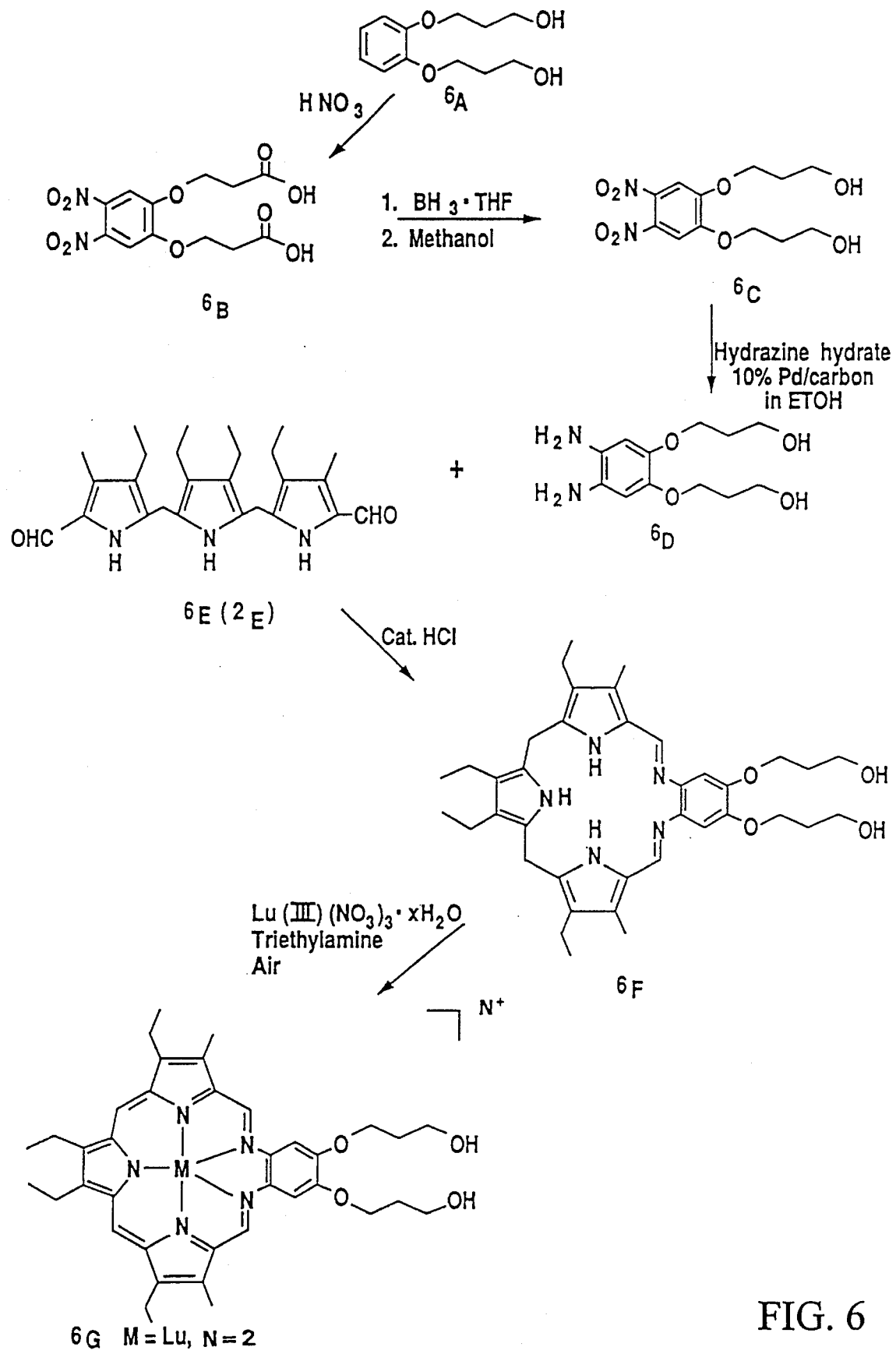
FIG. 6 schematically summarizes the synthesis of B2TXP, $6_F$ and $[LuB2TXP]^{2+}$, $6_G$.

1,2-Diamino-4,5-bis (3'-hydroxypropyl) oxybenzene, $6_D$, FIG. 6. The diamine was obtained by reduction of the corresponding 1,2-bis ((3-hydroxypropyl) oxy) -4,5-dinitrobenzene (3.0 g, 9.6 mmol) with hydrazine hydrate (4.7 mL, 96.2 mmol) and 10% palladium on carbon (200 mg) in 120 mL refluxing absolute ethanol. The resulting brown suspension bubbled for approximately 15–20 minutes and then turned colorless after 1 hour. At this point, the reduction was deemed complete as judged by TLC (a low $R_f$ spot). The reaction solution was hot filtered through celite into a dry flask, covered with aluminum foil, and then concentrated to a gray solid. The diamine was recrystallized from hot acetone/n-hexanes to yield 2.20 grams (91%) of an off-white fine powder. For the diamine: mp 115°–117° C.; $^1$H NMR ($d_6$-DMSO) δ:1.76 (p, 4H, $OCH_2CH_2CH_2OH$), 3.53 (q, 4H, $OCH_2CH_2CH_2OH$), 3.82 (t, 4H, $OCH_2CH_2CH_2OH$), 4.06 (s, 4H, NH), 4.44 (t, 2H, OH), 6.25 (s, 2H, ArH). $^{13}$C NMR ($d_6$-DMSO) δ: 42.68, 67.84, 77.08, 114.95, 139.01, 150.63. EI MS, m/z (rel. intensity): 256 (100); HRMS (M$^+$) 256. 1420 (calcd for $C_{12}H_{20}N_2O_4$: 256.1423).

4,5,9,24-Tetraethyl-16,17-his((3-hydroxypropyl)oxy)-10,23 -dimethyl- 13,20,25,26,27-pentaazapentacyclo [20.2.1.1$^{3,6}$. 1$^{8,11}$. 0$^{14,19}$] heptacosa-3,5,8,10,12,14(19), 15,17,20,22,24-undecaene. sp$^3$ B2 TXP, $6_F$, FIGS. 6. This macrocycle was prepared in >90% yield from 1,2-diamino-4,5-bis((3-hydroxypropyl)oxy) benzene and 2,5-bis ((3-ethyl-5-formyl-4-methylpyrrol-2-yl) methyl )-3,4-diethyl pyrrole by using the acid-catalyzed procedure reported earlier for the preparation of the reduced sp$^3$ texaphyrin, see Example 1. For B2 sp$^3$ texaphyrin: mp 190° C. dec; $^1$H NMR ($CDCl_3$) δ: 1.05 (t, 6H, $CH_2CH_3$), 1.12 (t, 6H, $CH_2CH_3$), 2.00 (t, 4H, $OCH_2CH_2CH_2OH$), 2.28 (s, 6H, pyrr-$CH_3$), 2.35 (q, 4H, $CH_2CH_3$), 2.48 (q, 4H $CH_2CH_3$), 3.00–3.50 (bs, 2H, OH), 3.78 (t, 4H, $OCH_2CH_2CH_2OH$), 3.93 (s, 4H, (pyrr) 2-$CH_2$), 4.19 (s, 4H, $OCH_2CH_2CH_2OH$), 7.16 (s, 2H, ArH), 8.34 (s, 2H, CHN), 11.16 (s, 1H, NH), 12.04 (s, 2H, NH); $^{13}$C NMR ($CDCl_3$) δ: 9.65, 15.45, 16.61, 17.23, 17.60, 22.18, 31.71, 60.75, 68.58, 100.86, 120.23, 120.37, 124.97, 125.06, 130.05, 133.86, 140.16, 140.86, 147.62; UV/vis $\lambda_{max}$ 369 nm; CI MS (M$^+$) 642; CI HRMS (M$^+$) 642. 4039 (calcd for $C_{34}H4N_5O_2$: 642.4019). Texaphyrin macrocycles having a free carboxyl or a free amino group for further derivatization on the benzene ring portion of the molecule can be synthesized by replacing $6_D$ of FIG. 6 with 3,4 diaminobenzoic acid or 3,4 diaminoaniline. Such macrocycles can be further functionalized to the derivatives shown in FIG. 23.

Lutetium (III) complex of 4,5,9,24-tetraethyl-16,17-bis(( 3-hydroxypropyl)oxy)-10,23-dimethyl-13,20,25,26,27-pentaazapentacyclo [20.2.1.1$^{3,6}$. 1$^{8,11}$. 0$^{14,19}$]heptacosa-1,3,5,7, 9,11 (27),12,14(19), 15,17,20,22(25),23-tridecaene [LuB2Txp]$^{2+}6_G$, FIG. 6. A mixture of the reduced texaphyrin ligand, 4,5,9,24 -16,17-bis((3 -hydroxypropyl ) oxy) - 10,23 -dimethyl-13,20,25,26,27-pentaazapentacyclo [20.2.1.1$^{3,6}$. 1$^{8,11}$.0$^{14,19}$]heptacosa 3,5,8,10,12,14(19),15,17, 20,22,24-undecaene (100 mg., 0.16 mmol), lutetium (III) nitrate hydrate (177 mg, 0.47 mmol) and triethylamine (10 drops) were combined in 150 mL of refluxing methanol for 12–24 hours. The dark green reaction mixture was concentrated on a rotary evaporator to dryness and dried in vacuo for 24 hours. The crude complex was dissolved in a 100 mL 1:1 (v/v) mixture of chloroform and methanol, filtered through celite and concentrated to 20 mL. A small amount of silica gel (approx. 3 grams) was added to the flask and then the dark green solution was carefully concentrated to dryness on a rotary evaporator. The silica was dried for 2 hours in vacuo, then it was loaded on a chloroform packed silica column and the complex was purified by first using neat chloroform and then increasing concentrations of methanol in chloroform (0%–20%) as eluents. The dark green band collected from the column was concentrated to dryness on a rotary evaporator and recrystallized from chloroform/methanol/diethyl ether to yield 50 mg (ca. 35%) of the lutetium (III) B2 texaphyrin. For the LU (III) complex: $^1$H NMR (CDCl$_3$/CD$_3$OH) δ: 1.82–1.91 (m, 12H, CH$_2$CH$_3$), 2.39 (m, 4H, OCH$_2$CH$_2$CH$_2$OH), 3.32 (m, 4H, OCH$_2$CH$_2$CH$_2$OH), 3.39 (s, 6H, pyrr-CH$_3$), 3.92–4.04 (m, 12H, OCH$_2$CH$_2$OH and CH$_2$CH$_2$), 9.52 (s, 2H, CH=C), 10.24 (s, 2H, ArH), 12.23 (s, 2H, CH=N); UV/vis: $\lambda_{max}$ 420.0, 477.5, 730.0; FAB MS M$^+$811.

Other lanthanide and rare earth-like metal complexes may be synthesized in a similar manner including the La$^{+3}$, Nd$^{+3}$, Sm$^{+3}$, Eu$^{+3}$, Gd$^{+3}$, Dy$^{+3}$ and Tm$^{+3}$ complexes.

EXAMPLE 4

Figure 7A:
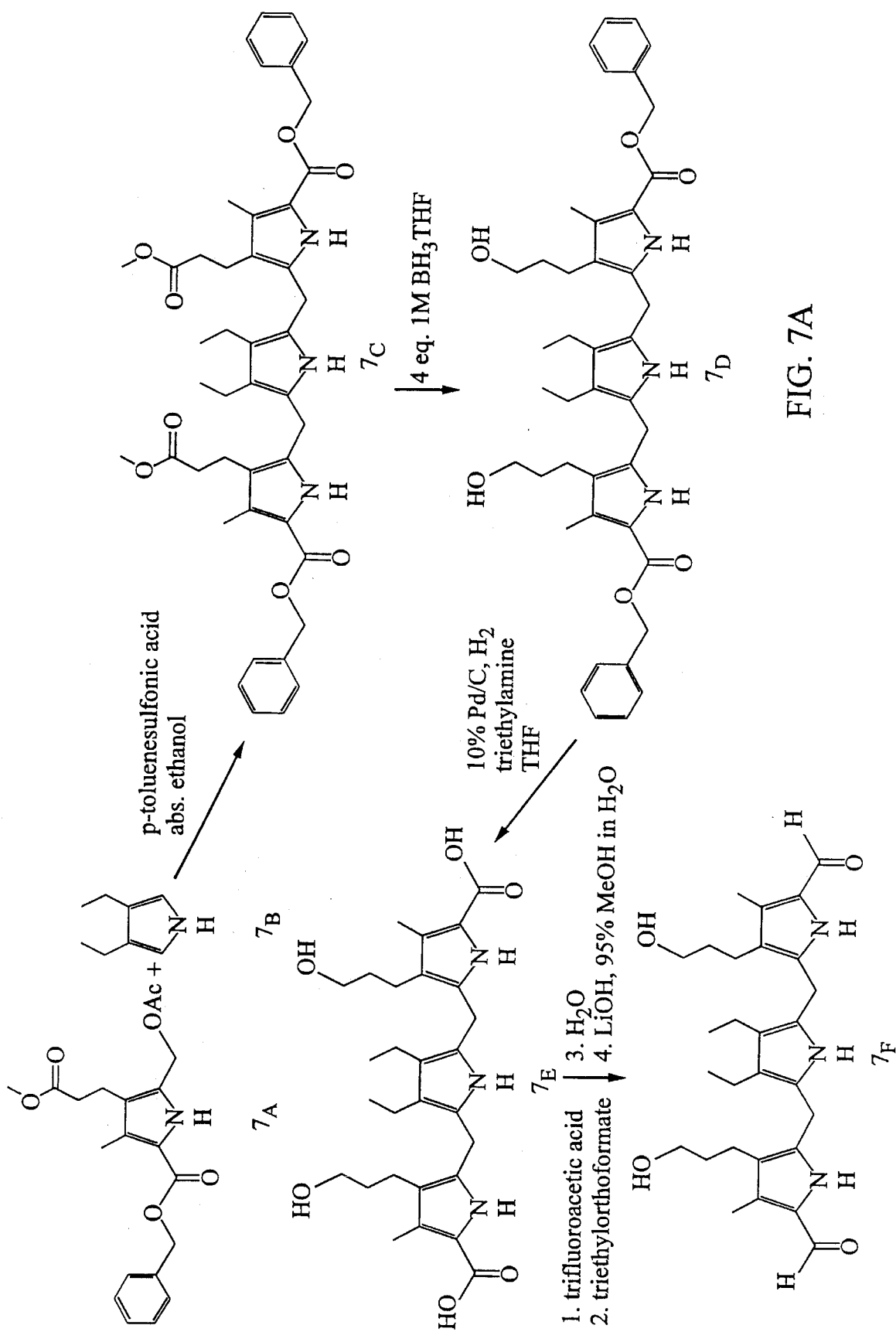
FIG. 7 schematically summarize the synthesis of B2T2TXP($7_H$) and lanthanide metal complexes of B2T2, $7_I$–$7_W$.
Figure 7B:
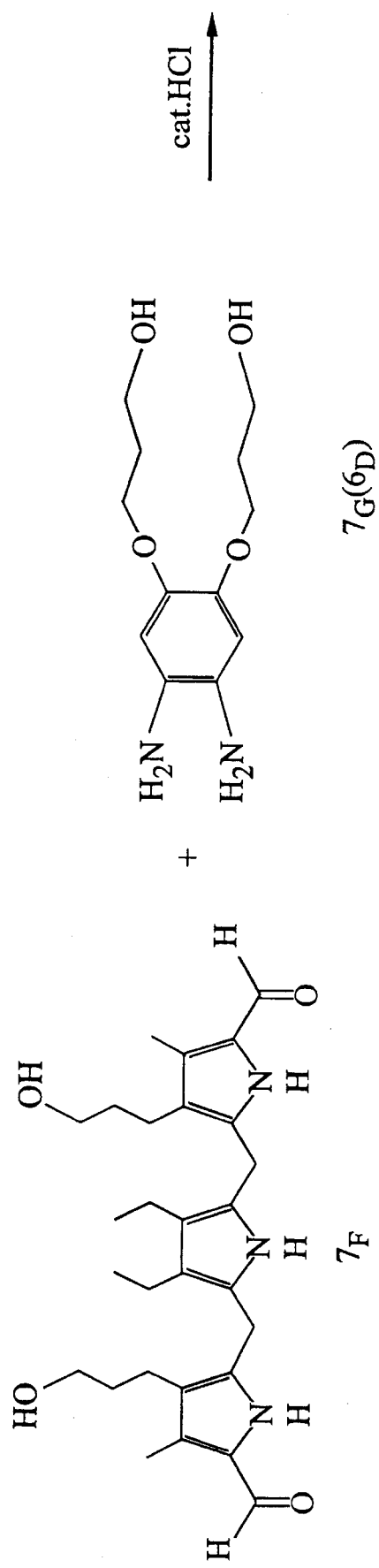
Figure 7C:
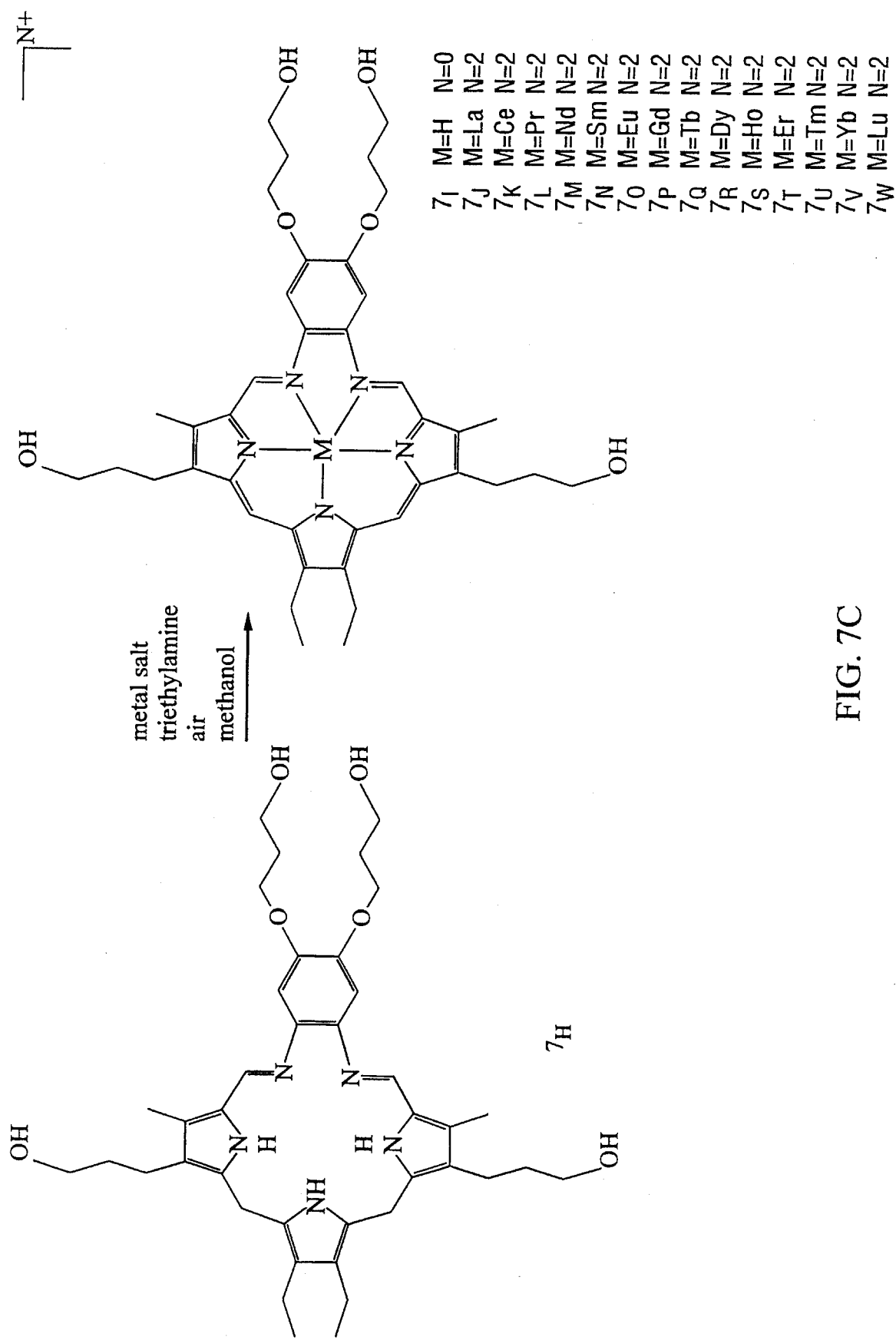

Synthesis of B2T2 TXP, see FIG. 7.

2,5-Bis[(5-benzyloxycarbonyl-4-methyl-3-methoxycarbonylethylpyrrol- 2-yl)methyl]-3,4-diethylpyrrole. 7$_C$, FIG. 7. In a 500 mL round bottom flask was placed 250 mL of ethanol from an unopened bottle and this was then purged with dry nitrogen for ten minutes. 3,4-Diethylpyrrole 7$_s$ (1.29 g, 0.01 mol) and 2-acetoxymethyl-5benzyloxycarbonyl-4-methyl-3methoxycarbonylethylpyrrole 7$_A$ (7.83 g, 0.02 mol) were added and the mixture heated until all of the pyrroles dissolved. p-Toluenesulfonic acid (65 mg) was added and the reaction temperature maintained at 60° C. The reaction slowly changed color from a clear yellow to a dark red with the product precipitating out of the solution as the reaction progressed. After ten hours the reaction was cooled to room temperature, the volume reduced to one half on a rotary evaporator, and then placed in the freezer for several hours. The product was collected by filtration, washed with a small amount of cold ethanol to afford 4.61 g of an off white fine powder (61%): $^1$H NMR (CDCl$_3$, 250 MHz): a 1.14 (6H, t, CH$_2$CH$_3$), 2.23 (6H, s, pyrrole-CH$_3$), 2.31 (4H, t, CH$_2$CH$_2$CO$_2$CH$_2$), 2.50 (4H, q, CH$_2$CH$_3$), 2.64 (4H, t, CH$_2$CH$_2$CO$_2$CH$_3$), 3.60 (10H, br s, CH$_3$CO$_2$ and (pyrrole)$_2$-CH$_2$), 4.44 (4H, br s, C$_6$H$_5$CH$_2$), 6.99–7.02 (4H, m, aromatic), 7.22–7.26 (6H, m, aromatic), 8.72 (1H, s, NH), 10.88 (2H, br s, NH); $^{13}$C NMR (CDCl$_3$, 250 MHz): δ 10.97, 16.78, 17.71, 19.40, 22.07, 35.09, 51.46, 65.32, 117.37, 119.34, 122.14, 126.58, 126.79, 127.36, 128.19, 133.55, 136.62, 162.35, 173.49; CI MS (M+H)$^+$750; HRMS 749.3676 (calc. for C$_{44}$H$_5$N$_3$O$_8$: 749.3676).

2,5-Bis[(5-benzyloxycarbonyl-3-(3-hydroxypropyl)-4-methylpyrrol-2yl)methyl]-3,4-diethylpyrrole. 7$_C$, FIG. 7. 2,5-Bis [(5-benzyloxycarbonyl-4-methyl-3methoxycarbonylethylpyrrol-2-yl)methyl]-3,4-diethylpyrrole 7$_C$ (5.00 g, 0.007 mol) was placed in a three necked 100 mL round bottom flask and vacuum dried for at least 30 minutes. The flask was equipped with a thermometer, an addition funnel, a nitrogen inlet tube, and a magnetic stir bar. After the tripyrrane was partially dissolved into 10 mL of dry THF, 29 mL of borane (1M BH$_3$ in THF) was added dropwise with stirring. The reaction became mildly exothermic and was cooled with a cool water bath. The tripyrrane slowly dissolved to form a homogeneous orange solution which turned to a bright fluorescent orange color as the reaction went to completion. After stirring the reaction for one hour at room temperature, the reaction was quenched by adding methanol dropwise until the vigorous effervescence ceased. The solvents were removed under reduced pressure and the resulting white solid redissolved into CH$_2$Cl$_2$. The tripyrrane was washed three times with 0.5M HCl (200 mL total), dried over anhydrous K$_2$CO$_3$, filtered, and the CH$_2$Cl$_2$ removed under reduced pressure until crystals of the tripyrrane just started to form. Hexanes (50 mL) was added and the tripyrrane allowed to crystallize in the freezer for several hours. The product was filtered and again recrystallized from CH$_2$Cl$_2$/ethanol. The product was collected by filtration and vacuum dried to yield 3.69 g of an orangish white solid (76%): mp 172°–173° C.; $^1$H NMR (CDCl$_3$, 300 MHz): a 1.11 (6H, t, CH$_2$CH$_3$), 1.57 (4H, p, CH$_2$CH$_2$CH$_2$OH), 2.23 (6H, s, pyrrole-CH$_3$), 2.39–2.49 (8H, m, CH$_2$CH$_3$ and CH$_2$CH$_2$CH$_2$OH), 3.50 (4H, t, CH$_2$CH$_2$CH$_2$OH), 3.66 (4H, s, (pyrrole)$_2$-CH$_2$), 4.83 (4H, s, C$_6$H$_5$-CH$_2$), 7.17–7.20 (4H, m, aromatic), 7.25–7.30 (6H, m, aromatic), 8.64 (1H, s, NH), 9.92 (2H, s, NH); $^{13}$C NMR (CDCl$_3$, 300 MHz): δ10.97, 16.72, 17.68, 20.00, 22.38, 33.22, 62.01, 65.43, 117.20, 119.75, 120.72, 122.24, 127.23, 127.62, 128.30, 132.95, 136.60, 162.13; FAB MS (M$^+$) 693.

2,5-Bis[[3-(3-hydroxypropyl)-5-carboxyl-4-methylpyrrol-2-yl) methyl]-3,4-diethylpyrrole 7$_E$, FIG. 7. 2,5-Bis[(3-(3 -hydroxypropyl)-5-benzyloxycarbonyl-4-methylpyrrol-2-yl)methyl]-3,4-diethylpyrrole 7$_D$ (15.0 g, 0.02 mol) was placed in a 1 L round bottom flask and dried in vacuo for ca. 30 min. The tripyrrane was dissolved in dry THF (600 mL) with triethylamine (10 drops) and 10% Pd on carbon (600 mg) and the reaction was stirred at room temperature under one atmosphere of H$_2$. After 15 h, the suspension was filtered through celite to remove the catalyst and the resulting clear solution was concentrated under reduced pressure to yield a light pink solid. This material, obtained in near quantitative yield, was taken on to the next step without further purification.

2,5-Bis[(5-formyl-3-(3-hydroxypropyl)-4-methylpyrrol-2-yl) methyl]-3,4-diethylpyrrole 7$_F$, FIG. 7. 2,5-Bis[(3-(3 -(hydroxypropyl)-5-carboxyl-4-methylpyrrol-2-yl)methyl]-3,4-diethylpyrrole 7$_E$ (10 g, 0.02 mol) was placed in a 250 mL round bottom flask and dried in vacuo for ca. 1 h. At room temperature under nitrogen, trifluoroacetic acid (31 mL, 0.40 mol) was added dropwise via syringe. The tripyrrane dissolved with visible evolution of CO$_2$ to form a homogeneous yellow solution. The reaction was stirred at room temperature for ca. 15 min, then cooled to −20° C. using a dry ice/CCl$_4$ bath. Freshly distilled triethylorthoformate (31 mL, 0.20 mol, dried over CaH$_2$) was added via a syringe to produce a dark orange/yellow solution. This mixture was stirred an additional 10 min at −20° C., then the cold bath was removed and 100 mL of distilled water was added dropwise to the solution. The resulting brown suspension was stirred at room temperature for 15 min. The product was collected by filtration, washed several times with water and re-suspended into a 50 mL/100 mL/50 mL (H$_2$O:EtOH:NH$_4$OH, v/v) mixture. The yellow/brown suspension was stirred for 1 h, filtered, washed several times with water, and then rinsed with a small amount of cold 95% ethanol. At this point, TLC analysis shows a mixture of tripyrranes. Therefore, the crude dialdehyde tripyrrane and LiOH.H$_2$O (2.10 g, 0.05 mol) were added to 400 mL of degassed 95% MeOH and the suspension heated to reflux under a N$_2$ atmosphere. The reaction became homogeneous when heated and after ca. 1 h, it was slowly cooled to room temperature. The reaction mixture was concentrated under reduced pressure to 75 mL and the resulting slurry placed in the freezer for several hours. The product was filtered and then purified by forming a slurry with 400 mL of methanol and 50 mL of water and heating close to boiling. The suspension was slowly cooled to room temperature, reduced to 150 mL under reduced pressure, and placed in the freezer for several hours. The purified dialdehyde tripyrrane was filtered, rinsed with water and dried in vacuo for 24 h to yield 7.65 g (80%) of a light tan powder. For $7_F$: mp 164°–166° C.; $^1$H NMR (CD$_3$OD): δ0.96 (t, 6H, CH$_2$CH$_3$), 1.49 (p, 4H, CH$_2$CH$_2$CH$_2$OH), 2.25 (s, 6H, pyrr-CH$_3$), 2.32–2.43 (m, 8H, CH$_2$CH$_3$ and CH$_2$CH$_2$CH$_2$OH), 3.46 (t, 4H, CH$_2$CH$_2$CH$_2$OH), 3.85 (s, 4H, (pyrr)2-CH$_2$), 9.34 (s, 2H, CHO); CI MS, M$^+$: m/e 480; HR MS, M$^+$: m/e 481.2942 (calcd. for C$_{28}$H$_{39}$N$_4$, 481.2941).

4,5-Diethyl-10,23-dimethyl-9,24-bis(3-hydroxypropyl)-16,17-bis(3-hydroxypropyloxy)-13,20,25,26,27-pentaazapentacyclo [20.2.1.1$^{3,6}$.1$^{8,11}$.0$^{14,19}$]heptacosa-3,5,8,10,12,14,16,18,20,22,24-undecaene ($7_E$, FIG. 7). 2,5-Bis [(5-formyl-3-(3-hydroxypropyl)-4-methylpyrrol-2-yl) methyl]-3,4-diethylpyrrole $7_F$ (1.00 g, 0.002 mol) and 1,2-diamino-4,5-bis (3-hydroxy-propyloxy) benzene $7_G$ (0.52 g, 0.002 mol) were placed in a 2 L round bottom flask with 1000 mL of toluene and 200 mL of methanol. The solvents were purged with nitrogen prior to use. Concentrated HCl (0.5 mL) was added and the reaction heated to reflux under nitrogen. The reaction went from a clear suspension of starting materials to a dark red homogeneous solution as the reaction proceeded. After 5 h the reaction was cooled to room temperature and the solvents removed under reduced pressure until the product precipitated out of solution. The remainder of the solvent was decanted off and the macrocycle dried in vacuo. The dark red product was recrystallized from methanol/diethylether and yielded 1.4–1.5g (90–100%). For $7_{H: mp}$ 190° C. dec; $^1$H NMR (CD$_3$OD): δ1.11 (t, 6H, CH$_2$CH$_3$), 1.76 (p, 4H, pyrr-CH$_2$CH$_2$CH$_2$OH), 2.03 (p, 4H, OCH$_2$CH$_2$CH$_2$OH), 2.36 (s, 6H, pyrr-CH$_3$), 2.46 (q, 4H, CH$_3$CH$_3$), 2.64 (t, 4H, pyrr-CH$_{CH2}$CH$_2$CH$_2$OH), 3.61 (t, 4H, pyrr-CH$_2$CH$_2$CH$_2$OH), 3.77 (t, 4H, OCH$_2$CH$_2$CH$_2$OH), 4.10 (s, 4H, (pyrr) 2-CH$_2$), 4.22 (t, 4H, OCH$_2$CH$_2$CH$_2$OH), 7.41 (s, 2H, PhH), 8.30 (s, 2H, HC=N); $^{13}$C NMR (CD$_3$OD): δ10.0, 17.2, 18.6, 20.9, 24.5, 33.2, 33.5, 59.6, 61.9, 67.8, 107.1, 120.7 123.8, 125.0, 125.8, 128.7, 144.8, 145.0, 150.7, 154.6; UV/vis (CH$_3$OH) [$\lambda_{max}$, nm]365; FAB MS, (M+H)$^+$: m/e 703; HRMS, M$^+$: m/e 701.4120 (calcd. for C$_{40}$H$_{55}$N$_5$O$_6$:701.4152). Anal. calcd. [C$_{40}$H$_{55}$N$_5$O$_6$](HCl) (CH$_3$OH): C, 63.92; H, 7.85; N, 9.09; Cl, 4.60. Found: C, 64.17; H, 7.68; N, 9.39; Cl, 4.70.

General procedure for the synthesis of water soluble lanthanide (III) 4,5-diethyl-10,23-dimethyl-9,24-bis (3-hydroxypropyl)-16,17-(3-hydroxypropyloxy)-13,20,25,26,27-pentaazapentacyclo[20.2.1.1$^{3,6}$.1$^{8,11}$.0$^{14,19}$]heptacosa-1,3,5,7,9,11(27),12,14,16,18,20,22(25),23-tridecaene ($7_I$, FIG. 7). One equivalent of the hydrochloride salt of the macrocycle, 4,5-diethyl-10,23-dimethyl-9,24-bis(3-hydroxypropyl)-16,17-bis(3-hydroxypropyloxy) -13,20,25,26,27-pentaazapentacyclo[20.2.1.1$^{3,6}$. 1$^{8,11}$.0$^{14,19}$]heptacosa-3,5,8,10,12,14,16,18,20,22,24-undecaene $7_H$, 1.5 equivalents of the Ln(NO$_3$)$_3$.XH$_2$O metal salt, 2–3 equivalents of tetrabutylammonium nitrate (TBANO$_3$) and triethylamine (ca. 1 mL) were mixed together in methanol and heated to reflux under air. After completion of the reaction (as judged by the UV/vis spectrum of the reaction mixture), the deep green solution was cooled to room temperature, the solvent removed under reduced pressure and the crude complex dried in vacuo for several hours. A solution of dichloromethane/methanol (99:1 v/v) was added to the crude complex and the suspension was sonicated a few min. The green suspension was filtered in order to remove red/brown colored impurities in the filtrate (incomplete oxidation products and excess triethylamine). The resulting deep green solid was first dissolved in methanol and then chloroform was added to reduce the polarity of the mixture (1:2 v/v). This solution was filtered through celite and loaded on a (pre-treated/pre-washed 1M NaNO$_3$) neutral alumina column (10 cm). The column was first eluted with a 1:10 (v/v) methanol/chloroform solution by gravity to remove a reddish brown impurity. The metal complex was then obtained by eluting the column with chloroform containing increasing amounts of methanol (20–50%). The purified lanthanide(III) texaphyrin complex was recrystallized by dissolving the complex in methanol/chloroform and carefully layering the dark green solution with a small amount of methanol, then with diethylether. The layered solution was kept at room temperature in the dark for a few days. Some of the lanthanide(III) texaphyrin complexes formed single crystals by this method. Other complexes were recrystallized twice for analytically pure measurements and characterizations.

Lanthanum(III) complex, $7_J$. The hydrochloride salt of macrocycle $7_H$ (300 mg, 0.407 mmol), La (NO$_3$)$_3$.6H$_2$O (350 mg, 0.814 mmol), TBANO$_3$ (305 mg, 1.0 mmol) and triethylamine (ca. 0.5 mL) in 350 mL methanol were heated to reflux under air for 10 h. After workup using the general procedure outlined above, 132 mg of the complex was obtained (34%). For $7_{J[<r]eset:}$ $^1$H NMR (CD$_3$OD): a 1.68 (t, 6H, CH$_2$CH$_3$), 2.22–2.30 (m, 4H, pyrr-CH$_2$CH$_2$CH$_2$OH and 4H, OCH$_2$CH$_2$CH$_2$OH), 3.20 (s, 6H, pyrr-CH$_3$), 3.72–3.78 (m, 4H, CH$_2$CH$_3$ and 4H, pyrr-CH$_2$CH$_2$CH$_2$OH and 4H, pyrr-CH$_2$CH$_2$CH$_2$OH), 3.94 (t, 4H, OCH$_2$CH$_2$CH$_2$OH), 4.78 (m, 4H, OCH=CH$_2$.CH$_2$OH), 9.37 (s, 2H, ArH), 9.87 (s, 2H, (pyrr)$_2$C=CH), 11.71 (s, 2H, HC=N); $^{13}$C NMR (CD$_3$OD): δ11.0, 18.9, 20.3, 23.0, 33.3, 36.3, 59.7, 62.2, 68.1, 101.5, 118.5, 137.1, 140.3, 144.6, 147.5, 148.2, 152.9, 154.9, 159.4; UV/vis: [(MeOH) $\lambda_{max}$, nm (log ε)]: 355 (4.34), 417 (4.73), 476 (5.06), 685.5 (4.08), 746 (4.59); FAB MS, M$^+$: m/e 835; HRMS, (M+H)+: m/e 836.2919 (calcd. for C$_{40}$H$_{51}$N$_5$O$_6$$^{140}$Ce, 836.2903). Anal. calcd. for [C$_{40}$H$_5$N$_5$O$_6$Ce](NO$_3$)$_2$(H$_2$O): C, 48.23; H, 5.47; N, 9.85. Found: C, 47.93; H, 5.41; N, 9.77.

Cerium(III) complex $7_L$. The hydrochloride salt of macrocycle $7_H$ (300 mg, 0.407 mmol), Ce (NO$_3$)$_3$.6H$_2$O (265 mg, 0.611 mmol), TBANO$_3$ (305 mg, 1.0 mmol) and triethylamine (ca. 0.5 mL) in 350 mL methanol were heated to reflux under air for 7 h. It is important to note that initially the reaction mixture formed a suspension, however, as the product formed the solution became homogeneous. After workup using the general procedure outlined above, 143 mg of dark green crystals were obtained (37%). This material was suitable for X-ray diffraction analysis. For 7x: UV/vis: [(MeOH) $\lambda_{max}$, nm (log ε)]: 349.5 (4.34), 416.5 (4.70) 476.5 (5.05), 684 (4.07), 741 (4.56); FAB MS, M$^+$: m/e 836; HRMS, (M+H)$^+$: m/e 836.2807 (calcd. for C$_{40}$H$_{51}$N$_5$O$_6$$^{140}$Ce, 836.2816). Anal. calcd. for [C$_{40}$H$_{50}$N$_5$O$_6$Ce](NO$_3$)$_2$ (H$_2$O)$_3$: C, 47.32; H, 5.56; N, 9.66. Found: C, 46.98; H, 5.22; N, 9.63.

Praseodymium(III) complex $7_L$. The hydrochloride salt of macrocycle $7_H$ (300 mg, 0.407 mmol), Pr (NO$_3$)$_3$. 5H$_2$O (255 mg, 0. 611 mmol), TBANO$_3$ (305 mg, 1.0 mmol) and triethylamine (ca. 0.5 mL) in 350 mL methanol were heated to reflux under air for 10 h. After workup using the general procedure outlined above, 200 mg of the complex was obtained (51%). For $7_L$: UV/vis: [(MeOH) $\lambda_{max}$, nm (log $\epsilon$)]: 352 (4.32), 416.5 (4.69), 476.5 (5.04), 689 (4.07), 744.5 (4.57); FAB MS, M$^+$: m/e 838; HRMS, M+: m/e 837.2823 (calcd. for C$_{40}$H$_{50}$N$_5$O$_6$$^{141}$Pr, 837.2838). Anal. calcd. for [C$_{40}$H$_{50}$N$_5$O$_6$Pr](NO$_3$)$_2$(CH$_3$OH) (H$_2$O): C, 48.65; H, 5.58; N, 9.69. Found: C, 48.75; H, 5.52; N, 9.71.

Neodymium(III) complex $7_M$. The hydrochloride salt of macrocycle $7_K$ (300 mg, 0.407 mmol), Nd(NO$_3$)$_3$.6H$_2$O(267 mg, 0.611 mmol), TBANO$_3$ (305 mg, 1.0 mmol) and triethylamine (ca. 0.5 mL) in 350 mL methanol were heated to reflux under air for 12 h. After workup using the general procedure outlined above, 125 mg of the complex was obtained (32%). For $7_M$: UV/vis: [(MeOH) $\lambda_{max}$, nm (log $\epsilon$)]:353.5 (4.32), 416 (4.68), 476 (5.05), 688 (4.06), 742.5 (4.56); FAB MS, M$^+$: m/e 839; HRMS, M+: m/e 838.2828 (calcd. for C$_{40}$H$_{50}$N$_5$O$_6$$^{142}$Nd, 838.2838). Anal. calcd. for [C$_{40}$H$_{50}$N$_{5](NO3)}$)$_2$(CH$_3$OH): C, 49.48; H, 5.47; N, 9.86. Found: C, 49.23; H, 5.49; N, 9.83.

Samarium(III) complex $7_N$. The hydrochloride salt of macrocycle 7K (300 mg, 0.407 mmol), Sm(NO$_3$)$_3$.5H$_2$O (270 mg, 0.611 mmol), TBANO$_3$ (305 mg, 1.0 mmol) and triethylamine (ca. 0.5 mL) in 350 mL methanol were heated to reflux under air for 7 h. After workup using the general procedure outlined above, 183 mg of a dark green crystalline solid was obtained (46%). This material has the potential for X-ray diffraction. For $7_N$: UV/vis: [(MeOH) $\lambda_{max}$, nm (log $\epsilon$)]: 354.5 (4.36), 415.5 (4.71), 475.5 (5.09), 682 (4.09), 741 (4.61); FAB MS, M$^+$: m/e 849; HRMS, M$^+$: m/e 848. 2957 (calcd. for C$_{40}$H5N$_5$O$_6$$^{152}$Sm, 848. 2959). Anal. calcd. for [C$_{40}$H$_{50}$N$_5$O$_6$Sm](NO$_3$)2(CH$_2$OH): C, 48.99; H, 5.42; N, 9.76. Found: C, 48.79; H, 5.64; N, 9.43.

Europium(III) complex $7_O$. The hydrochloride salt of macrocycle $7_H$ (400 mg, 0.543 mmol), Eu(NO$_3$)$_3$. 5H$_2$O (290 mg, 0.65 mmol), TBANO$_3$ (500 mg, 1.64 mmol) and triethylamine (ca 1 mL) in 350 mL methanol were heated to reflux under air for 16 h. After workup using the general procedure outlined above, 255 mg of a dark green crystalline solid was obtained (48%). This material was suitable for X-ray diffraction analysis. For 70: UV/vis: [(MeOH) $\lambda_{max}$, nm (log $\epsilon$)]: 414 (4.72), 475.5 (5.10), 678 (4.08), 739.5 (4.63); FAB MS, (M+H)$^+$: m/e 850; HRMS, M+: m/e 849.2961 (calcd. for C$_{40}$H$_{50}$N$_5$O$_6$Eu, 849.2974). Anal. calcd. for [C$_{40}$H$_{50}$N$_5$O$_6$](NO$_3$)$_2$(H$_2$O): C, 47.56; H, 5.39; N, 9.71. Found: C, 47.47; H, 5.45; N, 9.64.

Gadolinium (III) complex $7_P$. The hydrochloride salt of macrocycle $7_H$ (750 mg, 1 mmol), Gd(NO$_3$)$_3$.5H$_2$O(660 mg, 1.5 mmol), TBANO$_3$ (930 mg 3.0 mmol) and triethylamine (ca. 1 mL) in 600 mL methanol were heated to reflux under air for 12 h. After workup using the procedure outlined above, the dark green complex was recrystallized from chloroform/methanol/diethylether to yield 700 mg (72%) of a deep green crystalline solid. X-ray quality single crystals were obtained by dissolving the complex in methanol/chloroform and carefully layering the dark green solution with a small amount of methanol, then with diethylether. The layered solution was kept at room temperature in the dark for a few days. For $7_P$: UV/vis: [(MeOH) $\lambda_{max}$, nm (log $\epsilon$)]: 358 (4.33), 416 (4.72), 478 (5.12), 678 (4.03), 737.5 (4.64); [(H$_2$O) $\lambda_{max}$,nm (log $\epsilon$)]: 347 (4.43), 419 (4.75), 469 (5.08), 740 (4.60). IR (KBr, cm$^{-1}$, major peaks): v3299 (OH), 1647 (C=N), 1601 (C=N), 1507, 1456, 1437, 1385 (NO$_3$-), 1290, 1221, 1098, 1082. FAB MS, M+: m/e 854; HRMS, M$^+$: m/e 854.2989 (calcd. for C$_{40}$H$_{50}$N$_5$O$_6$$^{158}$Gd, 854.300. Anal. calcd. for [C$_{40}$H$_{50}$N$_5$O$_6$Gd](NO$_3$)$_2$(CH$_3$OH)(H$_2$O): C, 47.85; H, 5.49; N, 9.53. Found: C, 47.62; H, 5.37; N, 9.54. NOTE: If the alumina is not pre-treated with a NaNO$_3$ wash, the Gd(III) will not have two nitrate counter anions, instead it will have one nitrate and one chloride counter anion: Anal. calcd. for [C$_{40}$H$_{50}$N$_5$O$_6$Gd](NO$_3$)Cl(H$_2$O)$_2$: C, 48.65; H, 5.51; N, 8.51; Cl, 3.59. Found: C, 48.21; H, 5.58; N, 8.34; Cl, 3.62.

Terbium(III) complex $7_Q$. The hydrochloride salt of macrocycle $7_H$ (300 mg, 0.407 mmol), Tb(NO$_3$)$_3$.6H$_2$O (276 mg, 0.611 mmol), TBANO$_3$ (305 mg, 1.64 mmol) and triethylamine (ca. 0.5 mL) in 350 mL methanol were heated to reflux under air for 12 h. After workup using the general procedure outlined above, 152 mg of the complex was obtained (38%). For 7Q: UV/vis: [(MeOH) $\lambda_{max}$, nm (log $\epsilon$)]: 353 (4.35), 414 (4.71), 474.5 (5.09), 680 (4.08), 737 (4.62); FAB MS, M$^+$: m/e 856; HRMS, M$^+$: m/e 855.3017 (calcd. for C40H50N$_5$O$_6$$^{159}$Tb, 855.3015). Anal. calcd. for [C40H$_{50}$N$_5$O$_6$Tb](NO$_3$)$_2$(CH$_3$OH) (H$_2$O): C, 47.80; H, 5.48; N, 9.52. Found: C, 48.11; H, 5.28; N, 9.75.

Dysprosium(III) complex $7_R$. The hydrochloride salt of macrocycle $7_H$ (300 mg, 0.407 mmol), Dy(NO$_3$)$_3$.5H$_2$O (266 mg, 0.611 mmol), TBANO$_3$ (305 mg, 1.64 mmol) and triethylamine (ca. 0.5 mL) in 350 mL methanol were heated to reflux under air for 5 h. After workup using the general procedure outlined above, 250 mg of the complex was obtained (62%). For $7_R$: UV/vis: [(MeOH) nm (log $\epsilon$)]: 354 (4.32), 414 (4.68), 475 (5.07), 677.5 (4.03), 735.5 (4.60); FAB MS, (M+H)$^+$: m/e 861; HRMS, M$^+$: m/e 860.3048 (calcd. for C40H$_{50}$N$_5$O$_6$$^{164}$Dy, 860.3053). Anal. calcd. for [C$_{40}$H$_{50}$N$_8$O$_6$Dy](NO$_3$)$_2$(H$_2$O): C, 47.89; H, 5.23; N, 9.78. Found: C, 47.97; H, 5.22; N, 9.72.

Holmium(III) complex $7_S$. The hydrochloride salt of macrocycle $7_H$ (300 mg, 0.407 mmol), Ho(NO$_3$)$_3$.5H$_2$O (269 mg, 0.611 mmol), TBANO$_3$ (305 mg, 1.64 mmol) and triethylamine (ca. 0.5 mL) in 350 mL methanol were heated to reflux under air for 12 h. After workup using the general procedure outlined above, 220 mg of the complex was obtained (55%). For $7_S$: UV/vis: [(MeOH) $\lambda_{max}$, nm (log $\epsilon$)]: 354 (4.35), 414 (4.72), 475.5 (5.12), 677 (4.08), 734 (4.65); FAB MS, M$^+$: m/e 862; HRMS, M$^+$: m/e 861.3044 (calcd. for C$_{40}$H$_{50}$N$_5$O$_6$$^{165}$Ho, 861.3064). Anal. calcd. for [C$_{40}$H$_{50}$N$_8$O$_6$Ho](NO$_3$)$_2$(CH$_3$OH)(H$_2$O): C, 47.52; H, 5.45; N. 9.47. Found: C, 47.55; H, 5.26; N, 9.30.

Erbium(III) complex $7_T$. The hydrochloride salt of macrocycle $7_H$ (300 mg, 0.407 mmol), Er(NO$_3$)$_3$.5H$_2$O (270 mg, 0.611 mmol), TBANO$_3$ (305 mg, 1.64 mmol) and triethylamine (ca. 0.5 mL) in 350 mL methanol were heated to reflux under air for 12 h. After workup using the general procedure outlined above, 143 mg of the complex was obtained (36%). For 7T: UV/vis: [(MeOH) $\lambda_{max}$, nm (log $\epsilon$)]: 355.5 (4.36), 414.5 (4.72), 477 (5.13), 672 (4.08), 732 (4.66); FAB MS, M$^+$: m/e 863; HRMS, M$^+$: m/e 865.3110 (calcd. for C$_{40}$H$_{50}$N$_5$O$_6$$^{166}$Er, 862.3064). Anal. calcd. for [C$_{40}$H$_{50}$N$_5$O$_6$Er](NO$_3$)$_2$(CH$_3$OH): C, 48.32; H, 5.34; N, 9.63. Found: C, 48.14; H, 5.14; N, 9.55.

Thulium(III) complex $7_U$. The hydrochloride salt of macrocycle $7_H$ (300 mg, 0.407 mmol), Tm(NO$_3$)$_3$.5H$_2$O (274 mg, 0.611 mmol), TBANO$_3$ (305 mg, 1.64 mmol) and triethylamine (ca. 0.5 mL) in 350 mL methanol were heated to reflux under air for 22 h. After workup using the general procedure outlined above, 150 mg of the complex was obtained (37%). This complex is more difficult to purify due to its lower solubility in methanol/chloroform solutions, which leads to its lower yield. For $7_U$: UV/vis: [(MeOH)

$\lambda_{max}$, nm (log ε)]: 355.5 (4.36), 414.5 (4.72), 477 (5.13), 672 (4.08), 732 (4.66); FAB MS, M$^+$: m/e 866; HRMS, M$^+$: m/e 865.3110 (calcd. for $C_{40}H_{50}N_5O_{16}{}^{169}Tm$, 865.3103). Anal. calcd. for $[C_{40}H_{50}N_5O_6Tm](NO_3)_2(H_2O)_2$: C, 46.82; H, 5.31; N, 9.56. Found: C, 46.85; H, 5.23; N, 9.38.

Ytterbium(III) complex $7_V$. The hydrochloride salt of macrocycle 7H (300 mg, 0.407 mmol), Yb(NO$_3$)$_3$.5H$_2$O (274 mg, 0.611 mmol), TBANO$_3$ (305 mg, 1.64 mmol) and triethylamine (ca. 0.5 mL) in 350 mL methanol were heated to reflux under air for 24 h. After workup using the general procedure outlined above, 220 mg of the complex was obtained (54%). For 7v: FAB MS, M$^+$: m/e 870; HRMS, M$^+$: m/e 870.3132 (calcd. for $C_{40}H_{50}N_5O_6{}^{174}Yb$, 870.3149).

Lutetium(III) complex $7_W$. The hydrochloride salt of macrocycle $7_H$ (300 mg, 0.407 mmol), Lu (NO$_3$)$_3$.H$_2$O (220 mg, 0.611 mmol), TBANO$_3$ (305 mg, 1.64 mmol) and triethylamine (ca. 0.5 mL) in 350 mL methanol were heated to reflux under air for 24 h. After workup using the general procedure outlined above, 150 mg of the complex was obtained (37%). This complex has very low solubility in methanol/chloroform solution. Almost half of the product remained on the column during purification. For $7_W$: FAB MS, M$^+$: m/e 872; HRMS, M$^+$: m/e 871.3154 (calcd. for $C40H_{50}N_5O6{}^{175}Lu$, 871.3169).

Acid-catalyzed Schiff-base condensation between $7_G$ and $7_F$ produced the so-called "sp$^3$" nonaromatic macrocycle $7_H$ in quantitative yield. Macrocycle $7_H$ is quite stable, decomposing only slightly over a period of months when stored in freezer. Oxidation and metallation of $7_H$ in the presence of 1.5 equivalents of lanthanide(III) metal salt, triethylamine, and air in boiling methanol produces a deep green metal complex within 3–24 hours (as judged by UV-Vis) of reaction time. All the lanthanide(III) [La—Lu, except Pm] texaphyrin complexes $7_I$–$7_W$ were isolated with unoptimized yields ranging from 34%–75%. Satisfactory spectroscopic and mass spectrometric data were obtained for all new compounds. Single crystals suitable for X-ray diffraction analysis of the Eu(III) and Gd(III) complexes $7_O$ and $7_P$, (see-FIG. 2), respectively, were obtained by dissolving each complex in MeOH/CHCl$_3$ and layering with diethyl ether.

EXAMPLE 5

Synthesis of B4T2 TXP:

1,2-Dihydroxy-4,5-dinitrobenzene. $8_B$, FIG. 8. In a dry 500 mL round bottom flask, 1,2-dimethoxy-4,5-dinitrobenzene (3.2 g, 0.12 mmol) $8_A$ was stirred vigorously in 40 mL of glacial acetic acid at 30° C. Once a homogeneous solution 200 mL of 48% HBr was added to the flask and the reaction was slowly heated to reflux. The reaction was complete as indicated by TLC after 4 hours. The work up involved pouring the cooled solution into 800 mL of ice water and then extracting the aqueous phase with CHCl$_3$ (3×150 mL) in order to remove any organic impurities. The dinitro catechol was extracted out of the aqueous layer with ethyl acetate (3×150 mL). The combined ethyl acetate extracts were washed with water and brine (3×100 mL), then dried over MgSO$_4$ and concentrated to an orange residue. Approximately 100 mL of dichloromethane was added to the residue and then placed in the freezer for several hours. The light yellow needles that formed were filtered and washed with dichloromethane to yield 2.37 g of product (84%). $^1$H NMR (d$_6$-acetone): δ3.45 (OH), 7.42 (Ar—H); $^{13}$C NMR (d6-acetone): δ112.44, 137.00, 149.97, EI MS M$^+$200.

1,2-Bis(2,3-dihydroxypropyloxy)-4,5-dinitrobenzene. $8_C$, FIG. 8. 1,2-Dihydroxy-4,5-dinitrobenzene $8_B$ (5.0 g, 22 mmol) and 1-chloro-2,3-dihydroxypropane (12.1 g, 110 mmol) were refluxed for 48 hours in a solution of potassium hydroxide (4.4 g) in 1-butanol (100 mL) under a nitrogen atmosphere. The resulting mixture was concentrated under reduced pressure, and the dark residue was partitioned between 100 mL of THF and 100 mL of brine/50 mL water solution in a 500 mL separatory funnel. The mixture was allowed to separate and the aqueous phase was extracted with THF (2×100 mL). The combined THF extracts were washed with brine (2×50 mL), dried over MgSO$_4$ and concentrated to an oily residue. Here, CH$_2$Cl$_2$ was added very carefully to insure precipitation of the crude product. After stirring for 15 minutes, the suspension was filtered with a medium glass fitted funnel and air dried for several minutes. The orange solid was taken up in 120 mL of CHCl$_3$ and 80 mL of diethyl ether at reflux and hot filtered to remove some impurities. The crude product was dissolved in a mixture of acetone and methanol (sonication may be required), then 6 grams of deactivated silica gel was added to the orange solution. The slurry was concentrated to dryness and the orange solid was dried in vacuo for one hour. The orange solid was loaded on a packed deactivated silica gel column. The column was eluted starting with neat CHCl$_3$ followed by CHCl$_3$ with increasing concentration of methanol (0–10%). After a bright yellow impurity (monoalkylated product) was removed a colorless product began to elute (using 8–10% methanol in CHCl$_3$ eluents). Conversely, on TLC the product will elute faster than the bright yellow monoalkylated product. The purified dialkylated tetrahydroxy product can be recrystallized from acetone/diethyl ether to yield 2.60 grams (30%) of a light yellow fluffy solid. $^1$H NMR (d6-acetone): δ2.95 (bs, 4H, OH), 3.69 (d, 4H, OCH$_2$CH(OH)CH$_2$OH), 4.06 (p, 2H, OCH$_2$CH(OH)CH$_2$OH), 4.24–4.35 (m, 4H, OCH$_2$CH(OH) CH$_2$OH), 7.72 (s, 2H, Ar-H); $^{13}$C NMR (d$_6$-acetone): δ63.55, 70.89, 72.53, 109.99, 137.22, 152.77. CI MS 349.

1,2-Diamino-4,5-bis ((2,3-dihydroxypropyl)oxy)benzene. $8_D$, FIG. 8. The diamine was obtained by reduction of the corresponding 1,2-bis ((2,3-dihydroxypropyl)oxy) -4,5-dinitrobenzene (0.30 g, 0.86 mmol) with hydrazine hydrate (1 mL) and 10% palladium on carbon (50 mg) in 40 mL refluxing absolute ethanol. The resulting brown suspension bubbled for approximately 15–20 minutes and then turned colorless after 1 hour. At this point the reduction was deemed complete as judged by TLC (R$_f$=0.63, 100% methanol). The reaction solution was hot filtered through celite into a dry flask, covered with aluminum foil, and then concentrated to a light yellowish oil. The diamine was taken to the next step without further purification. For B4 diamine: $^1$H NMR (CD$_3$OD): δ3.54–3.58 (m, 4H, OCH$_2$CH(OH)CH$_2$OH), 3.80–3.85 (m, 6H, OCH$_2$CH(OH)CH$_2$OH), 6.39 (s, 2H, Ar—H); $^{13}$C NMR (CD$_3$OD): δ64.27, 71.88, 73.22, 107.61, 130.31, 143.74.

Figure 8:
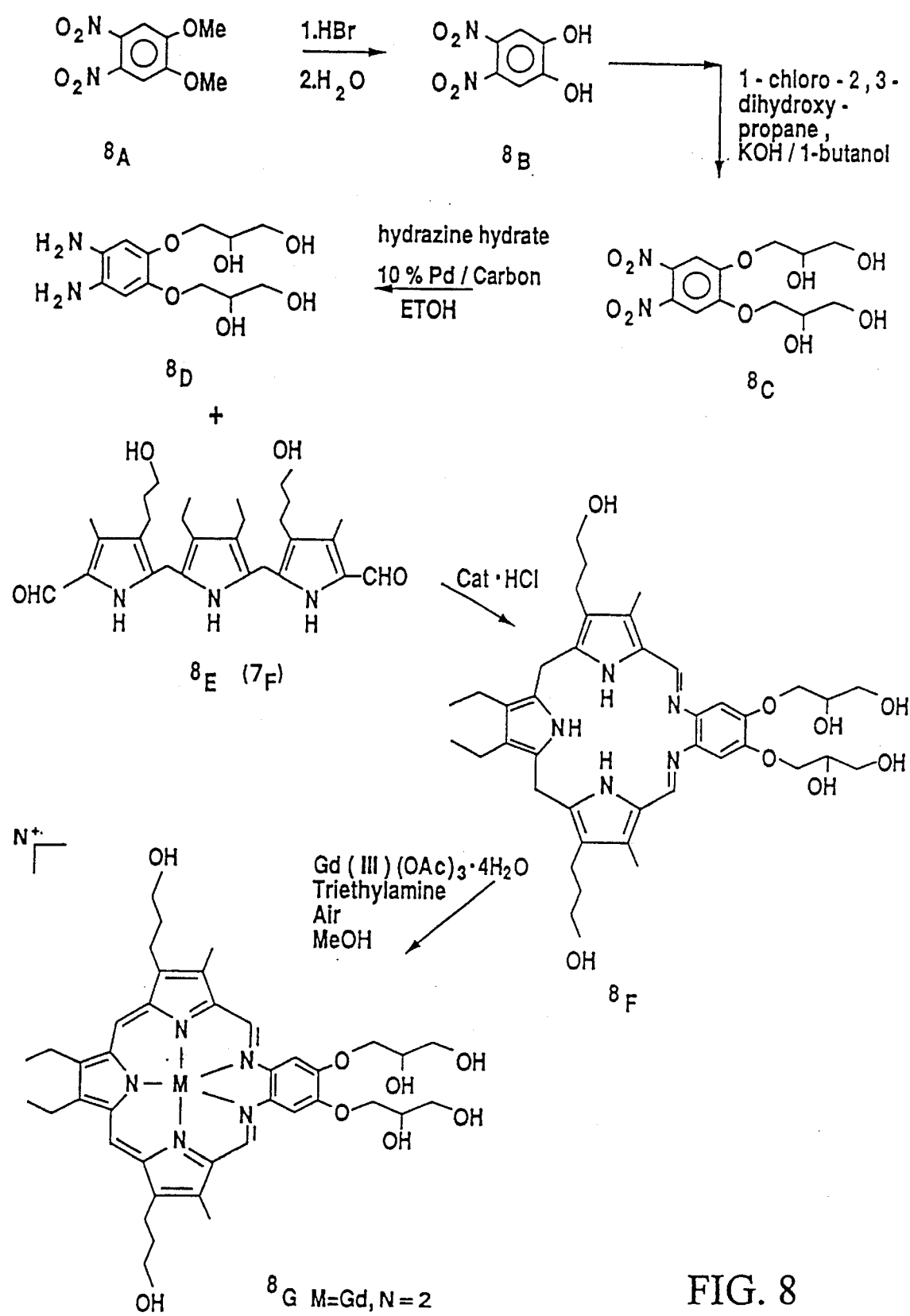
FIG. 8 schematically summarizes the synthesis of B4T2TXP($8_F$) and [Gd B4T2 TXP]$^{2+}$($8_G$).

4,5-Diethyl-9,24-bis(3-hydroxypropyl)-16,17-bis ((2,3-dihydroxypropyl)oxy)- 10,23-dimethyl-13,20,25,26,27-pentaazapentacyclo[20.2.1.1$^{3,6}$.1$^{8,11}$.0$^{14,19}$]heptacosa-3,5,8,10, 12, 14(19),15,17,20,22,24-undecaene. [sp$^3$ B4T2 TXP] $8_F$, FIG. 8. 2,5-Bis[(5-formyl-3-hydroxypropyl-4-methylpyrrol -2-yl)methyl]-3,4-diethylpyrrole (336 mg, 0.70 mmol) and 1,2-diamino-4,5-bis((2,3-dihydroxypropyl)oxy)benzene (ca 223 mg, 0.77 mmol) were placed in a 1 L round bottom flask with 600 mL of toluene and 175 mL of methanol. The solvents were purged with nitrogen prior to use. Concentrated HCl (ca 3 drops) was added and the reaction heated to reflux under nitrogen. After one hour the reaction was cooled to room temperature and the solvent removed under reduced pressure until the dark brown product precipitated. The remainder of the solvent was decanted off and the product dried in vacuo. The product was used in the next step without further purification.

Gadolinium (III) complex of 4,5-Diethyl-9,24-bis (3-hydroxypropyl) -16,17-bis ((2,3-dihydroxypropyl) oxy)-10, 23-dimethyl-13,20,25,26,27-pentaazapentacyclo [20.2.1.1$^{3,}$ $^{6}$.1$^{8,11}$.0$^{14,19}$]heptacosa-1,3,5,7,9,11(27),12,14(19),15,17, 20,22(25),23-tridecaene [GdB4T2Txp]. $8_G$, FIG. 8. Two identical reactions containing a mixture of reduced B4T2 texaphyrin ligand, 4,5-Diethyl-9,24-bis(3-hydroxypropyl)-16,17-bis(( 2,3-dihydroxypropyl)oxy)-10,23-dimethyl-13, 20,25, 26,27-pentaazapentacyclo[20.2.1. 1$^{3,6}$.1$^{8,11}$.0$^{14,19}$] heptacosa -3,5,8,10,12,14(19),15,17,20,22,24-undecaene, (0.75 g, 0.001 mol), gadolinium (III) acetate tetrahydrate (1.19 g, 0.003 mol), and triethylamine (ca 1 mL) were heated at reflux under air in 750 mL of absolute methanol. After heating for 17 hours the reactions were cooled slightly and air bubbled through the reaction mixture for several minutes. The reactions were then heated to reflux again. After heating for a total of 21 hours the reactions were cooled to room temperature, the solvent removed on a rotary evaporator, and the dark green products combined and dried in vacuo for several hours. The metal complex was dissolved into 100 mL of methanol and 6–8 grams of deactivated silica gel was added. (The silica gel was deactivated by adding a mixture of 6 mL water in 20 mL of methanol to 100 g of silica gel. After thorough mixing, the silica gel was allowed to air dry for 12 hours before bottling). The solvent was carefully removed on a rotary evaporator and the silica/complex mixture dried in vacuo for one hour. The complex was loaded onto a prepacked column of deactivated silica gel (5 cm length×3.5 cm diameter) and eluted with chloroform containing increasing amounts of methanol (0–80%). Fractions containing the complex were collected and concentrated to dryness. The green complex was further purified by recrystallization from methanol/anhydrous ethyl ether. 480 mg of product was obtained from the two combined reactions (25%). For the complex: UV/vis, $\lambda_{max}$, nm (CH$_3$OH) 415, 474, 740; FAB MS (M+H)$^+$887; HR MS (M+H)$^+$ 887.2977 (calc for C$_{40}$H$_{50}$N$_5$O$_6$$^{158}$Gd, 887.2981).

EXAMPLE 6

Further derivatives of Texaphyrin.

Intermediates hydroxylated in various positions can be combined to effect the synthesis of a number of compounds. For example, the B4 TXP derivative is synthesized by reacting the intermediate compound $6_E$ from FIG. 6 with compound $8_D$ of FIG. 8. This constructs a molecule without hydroxyl groups on the tripyrrole moiety but with 4 hydroxyl groups on the benzene ring moiety.

The molecule T2 TXP is synthesized by reacting intermediate $7_H$ in FIG. 7 with 4,5-dimethyl-1, 2-phenylenediamine to yield a texaphyrin derivative with two hydroxyls on the tripyrrole portion of the molecule and no hydroxyl substituents on the benzene ring.

A heptahydroxylated target B4T3 TXP is obtained by using the appropriate derivative 3-hydroxypropyl-4-methylpyrrole of the pyrrole (structure $7_E$ of FIG. 7) to make the trihydroxylated tripyrrole precursor which is then reacted with compound $8_D$ of FIG. 8.

Figure 12:
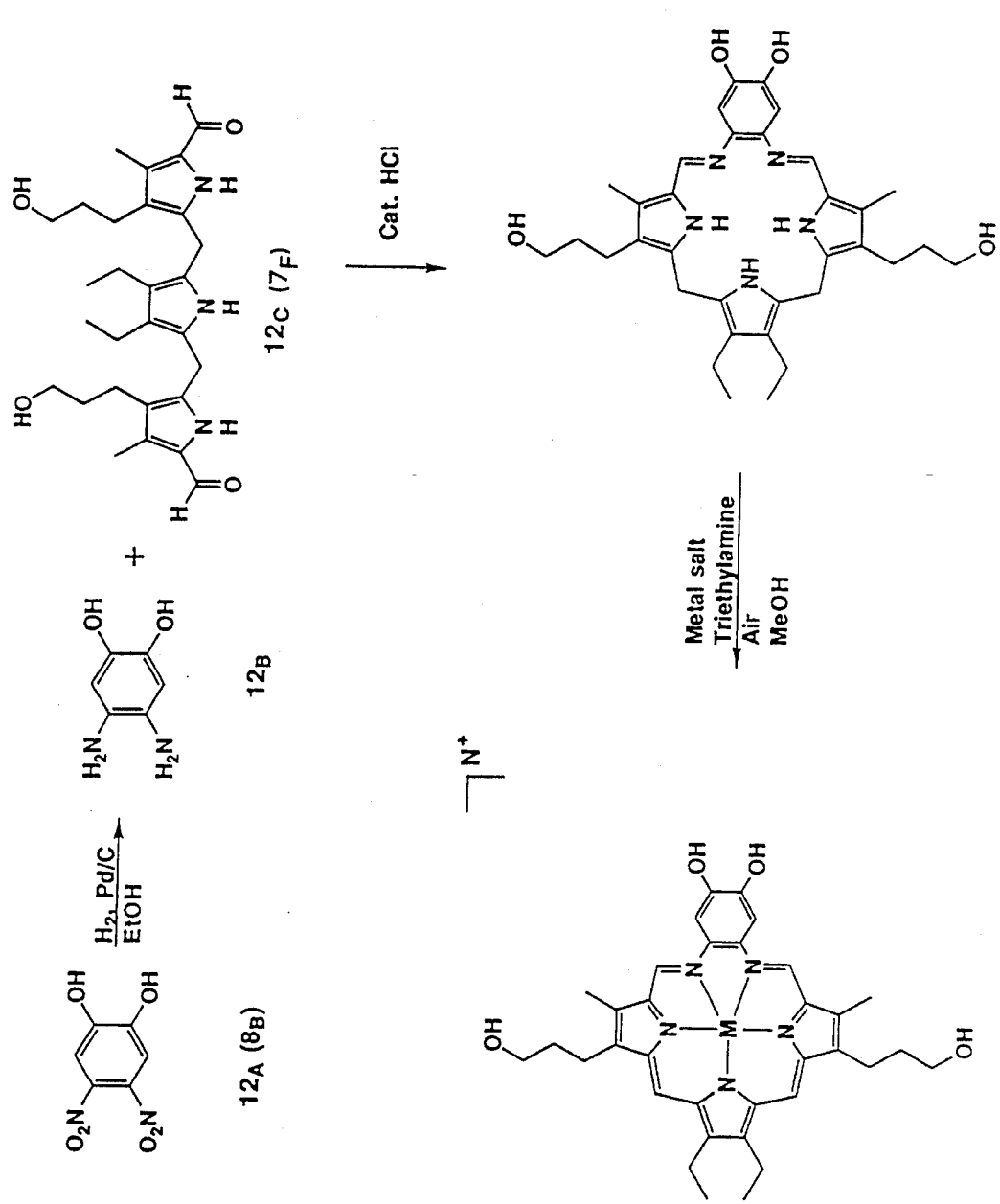
FIG. 12 summarizes the synthesis of catechol (i.e. benzene diol) texaphyrin derivatives bearing further hydroxyalkyl substituents off the tripyrrane-derived portion of the macrocycle.
Figure 13:
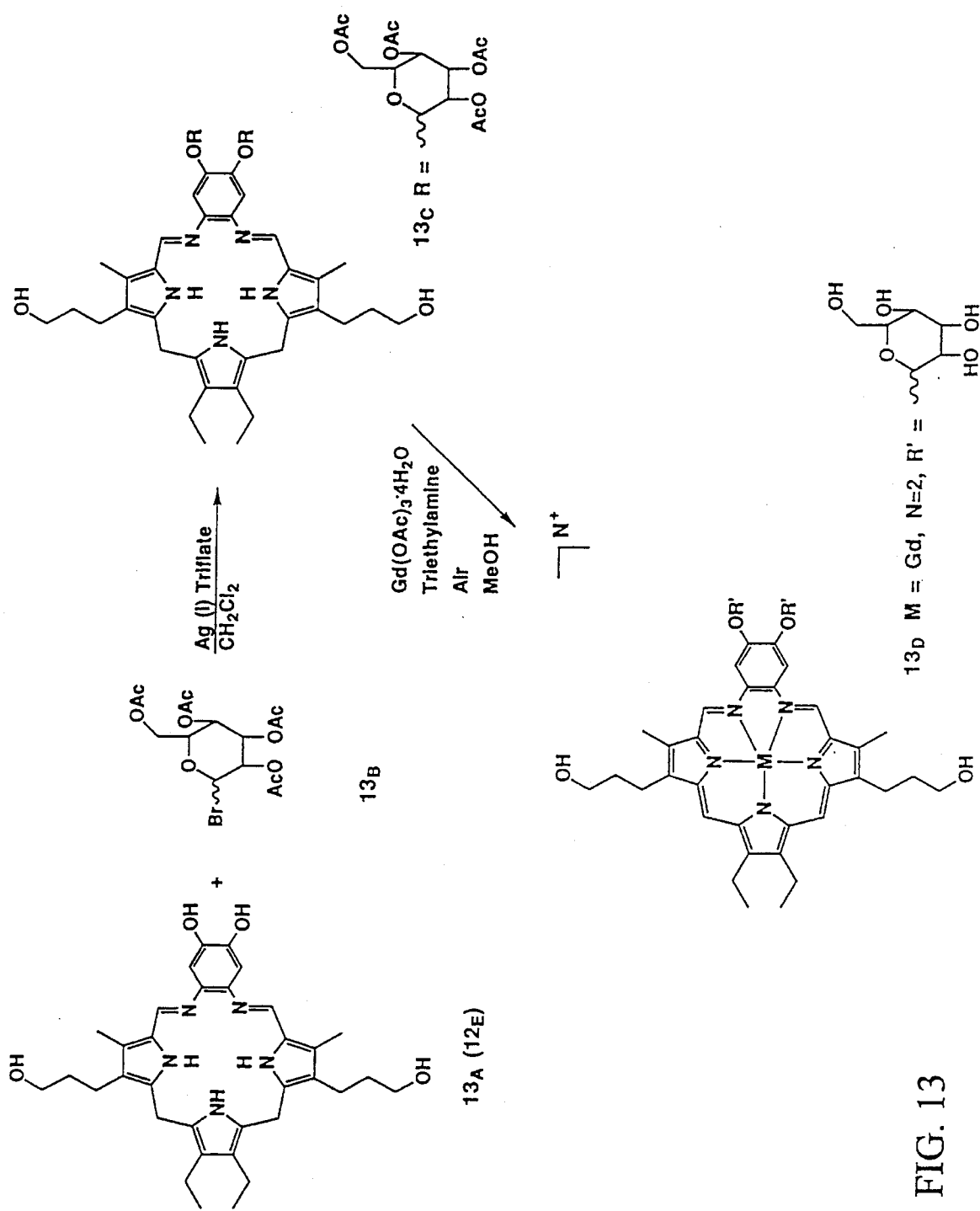
FIG. 13 provides an example of a saccharide substituted texaphyrin in which the saccharide is appended via an acetal-like glycosidic linkage. Triflate is trifluoromethanesulfonate.
Figure 14:
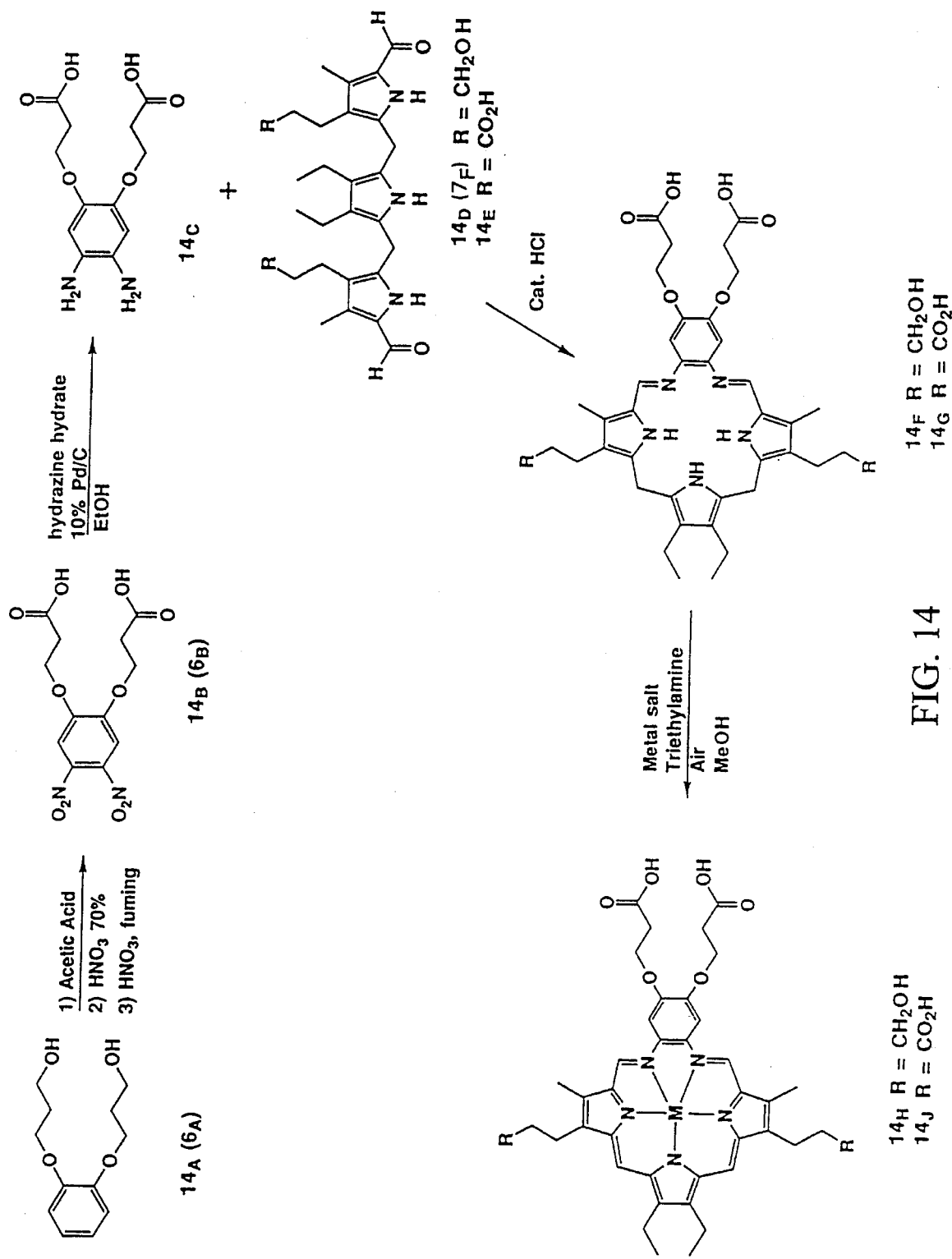
FIG. 14 summarizes the synthesis of a doubly carboxylated texaphyrin system in which the carboxyl groups are linked to the texaphyrin core via aryl ethers or functionalized alkyl substituents. The products of this scheme, compounds $14_H$ and $14_J$ could be converted on to various esterified products wherein the ester linkages serve to append further hydroxyl-containing substituents FIG. 15 summarizes the synthesis of polyhydroxylated texaphyrin derivatives via the use of secondary amide linkages. DCC is dicyclohexylcarbodiimide, DMF is dimethylformamide, and DME is dimethoxyethane.
Figure 15A:
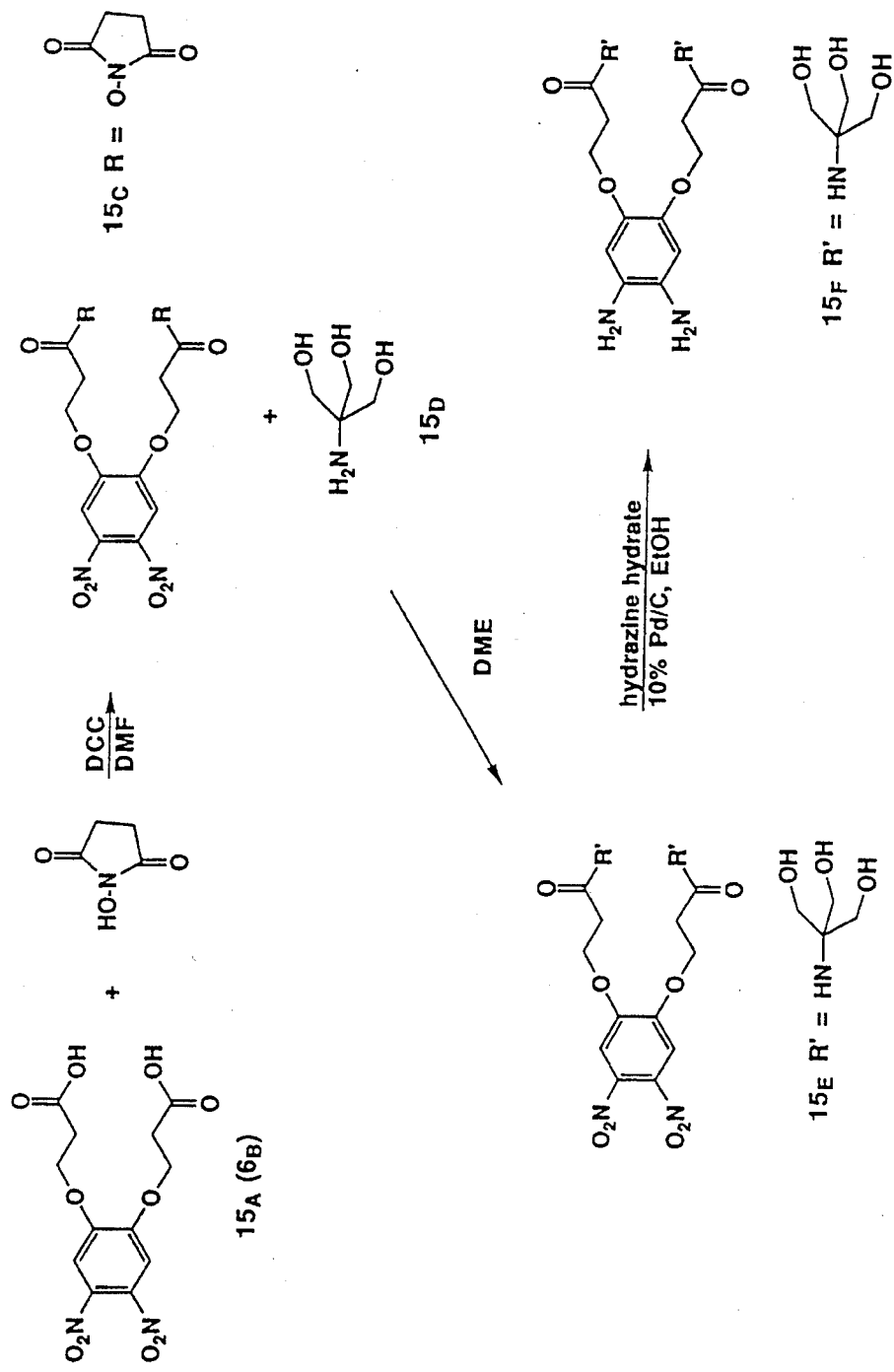
Figure 15B:
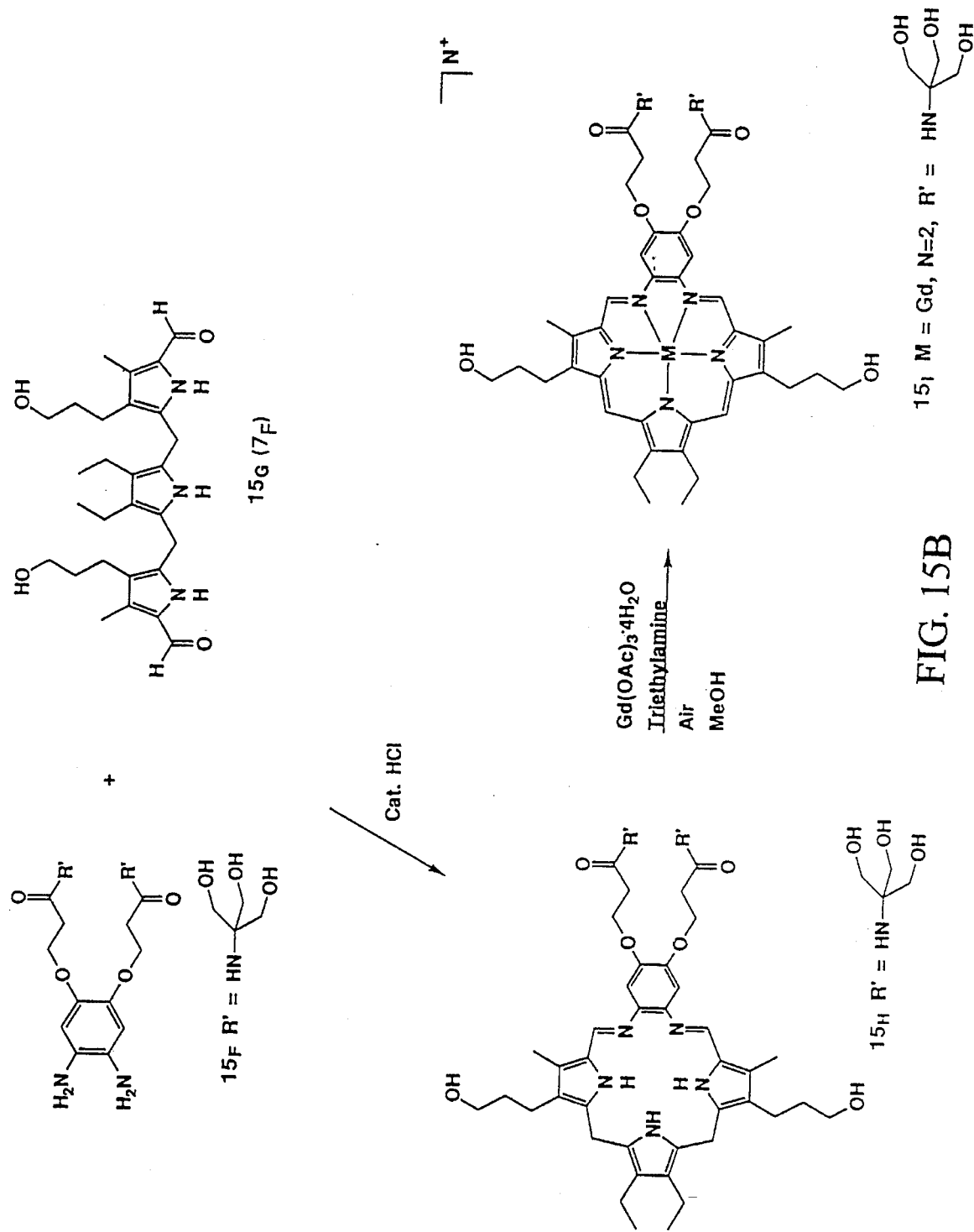
Figure 16A:
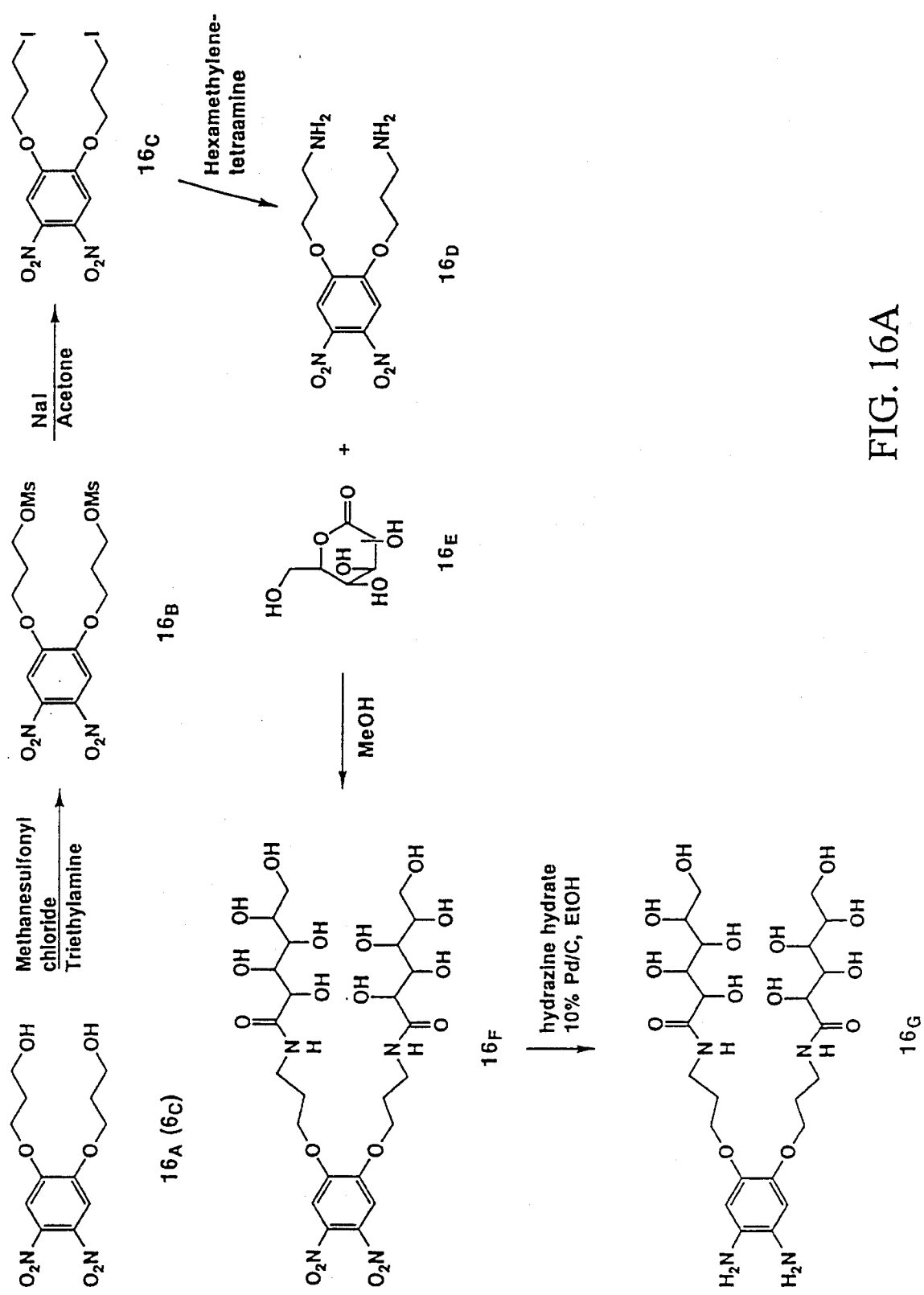
FIG. 16 summarizes the synthesis of another set of polyhydroxyl substituted texaphyrin derivatives using similar amide bonds as in FIG. 15.
Figure 16B:
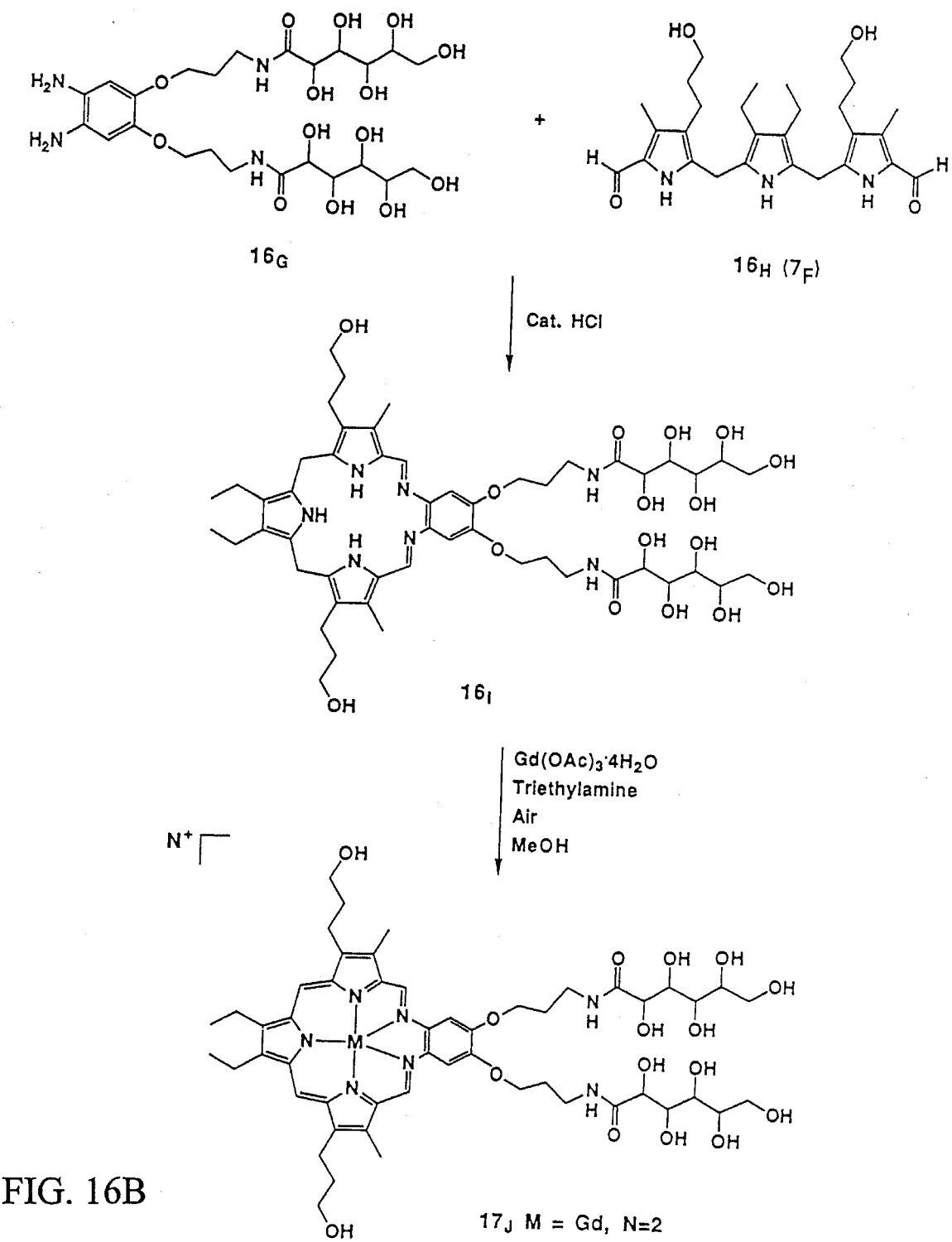
Figure 17A:
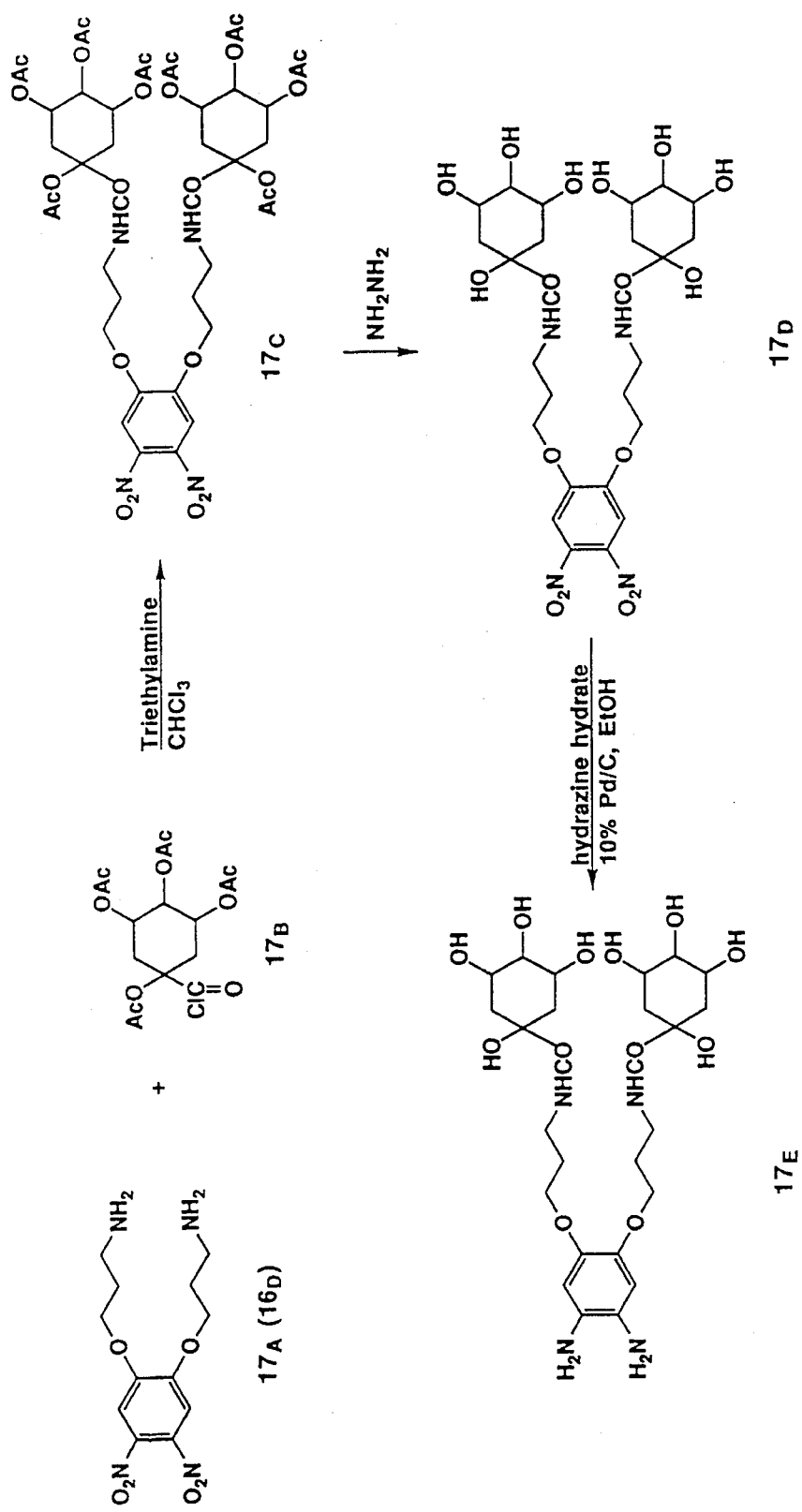
FIG. 17 summarizes the synthesis of saccharide substituted texaphyrins, wherein the saccharide moieties are appended via amide bonds.
Figure 17B:
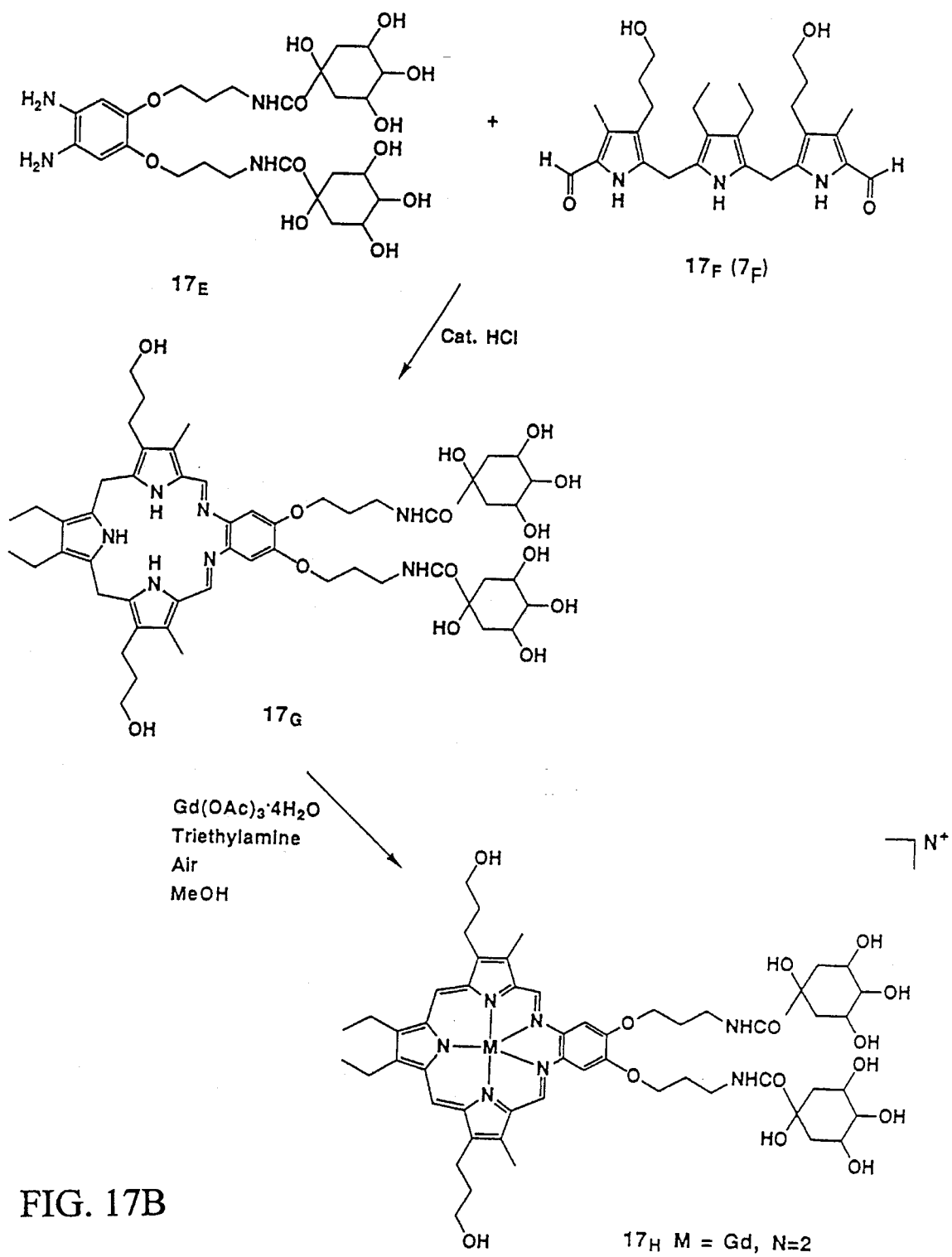
Figure 18:
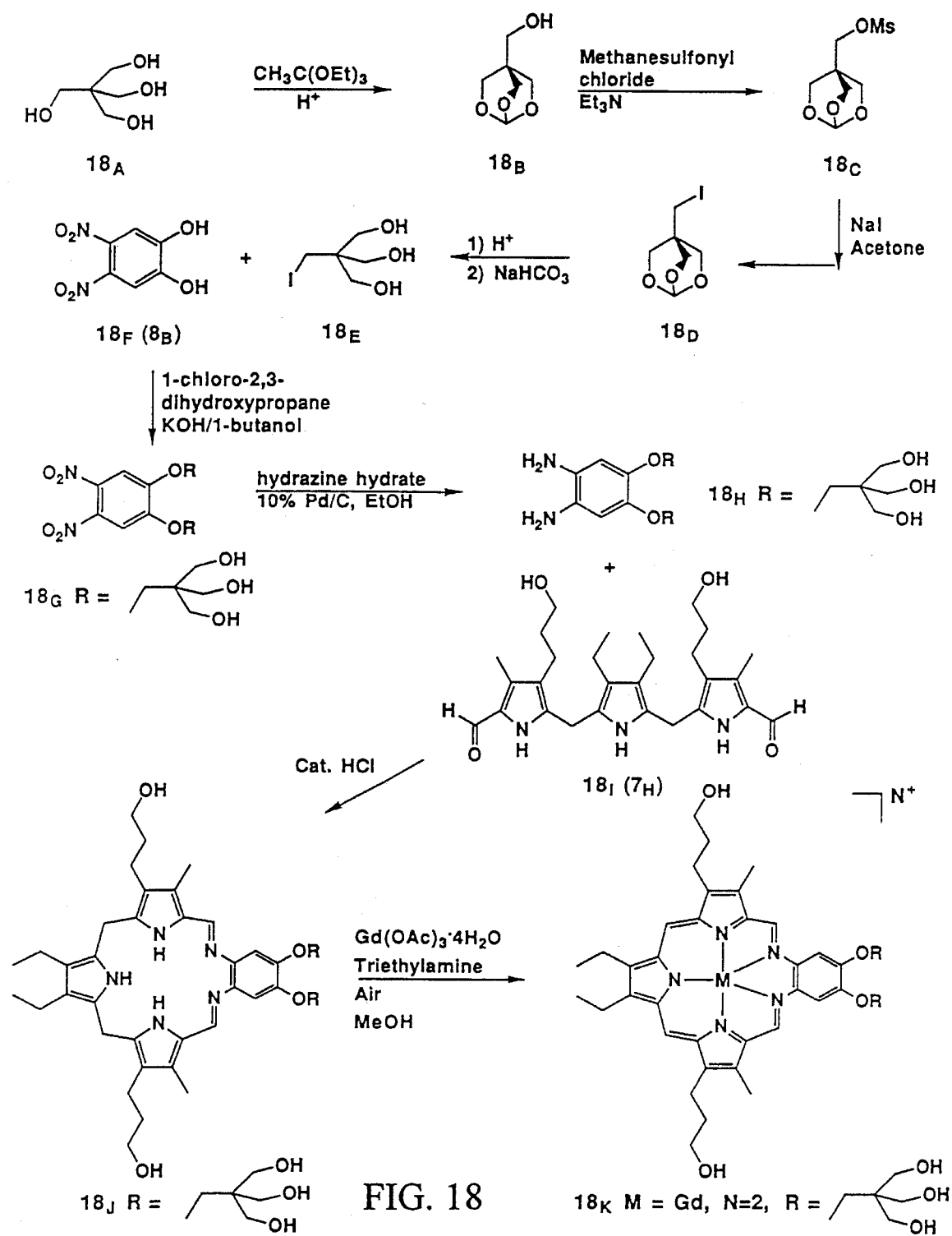
FIG. 18 summarizes the synthesis of polyhydroxylated texaphyrin derivatives containing branched polyhydroxyl (polyol) subunits appended to the texaphyrin core via aryl ethers.
Figure 19A:
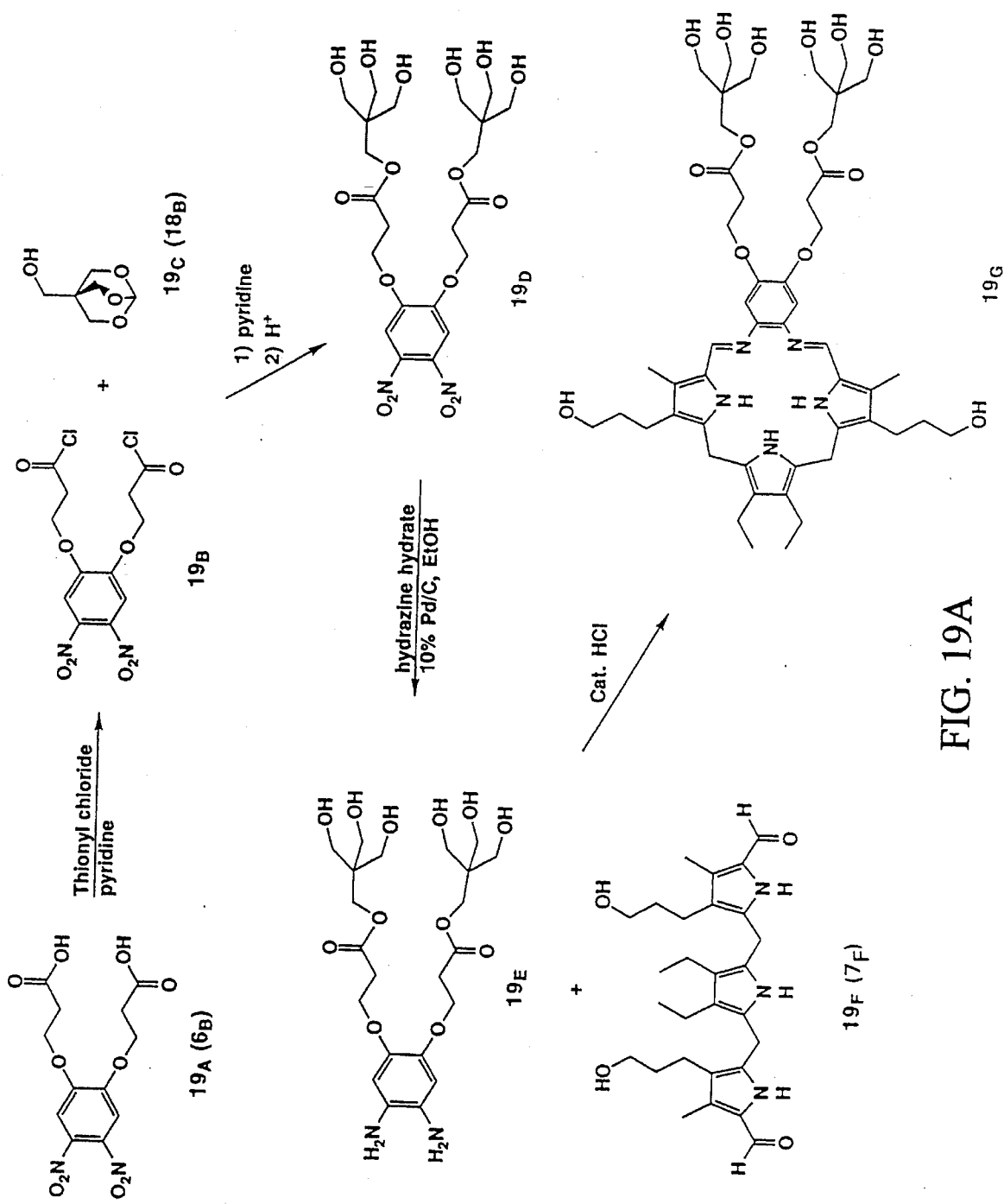
FIG. 19 summarizes how similar polyol subunits may be appended via ester linkages.
Figure 19B:
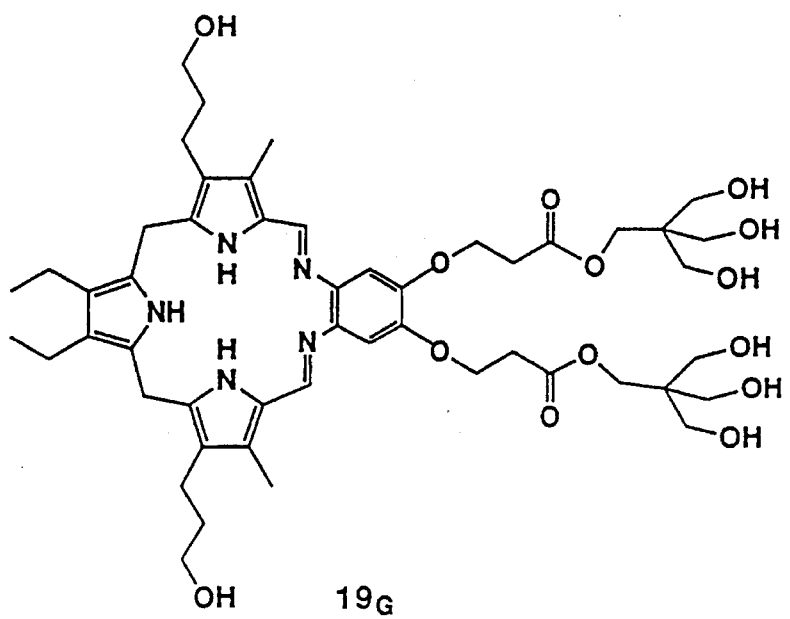
Figure 19B:
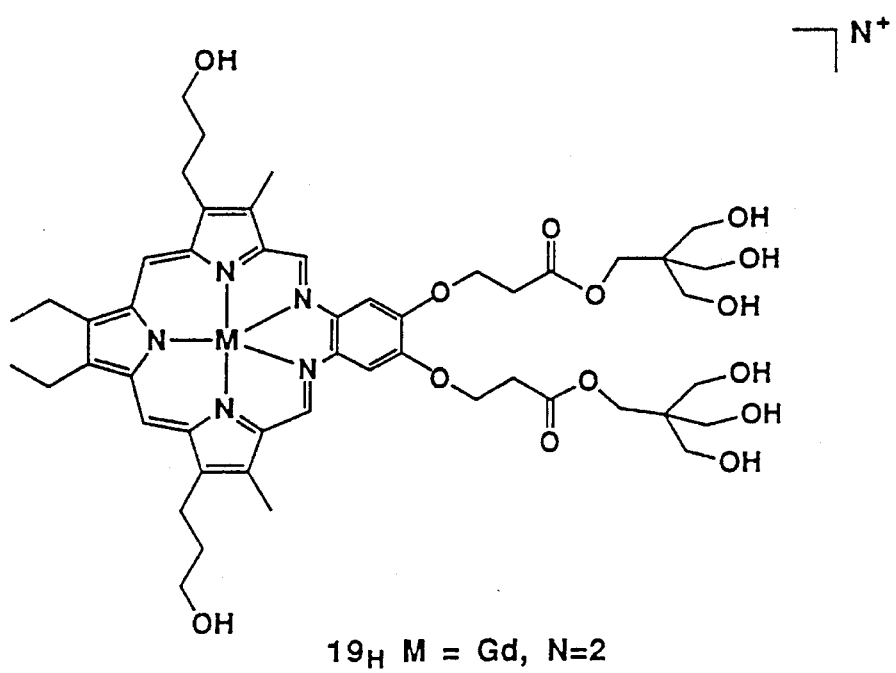

FIGS. 11–19 provide specific examples of how one skilled in the art could extend and refine the basic synthetic chemistry outlined in this application so as to produce other hydroxylated texaphyrins equivalent in basic utility to those specifically detailed in the examples. FIG. 11 summarizes the synthesis of polyether-linked polyhydroxylated texaphyrins. FIG. 12 summarizes the synthesis of catechol (i.e. benzene diol) texaphyrin derivatives bearing further hydroxyalkyl substituents off the tripyrrane-derived portion of the macrocycle. FIG. 13 provides an example of a saccharide substituted texaphyrin in which the saccharide is appended via an acetal-like glycosidic linkage. An oligosaccharide or a polysaccharide may be similarly linked to a texaphyrin. FIG. 14 summarizes the synthesis of a doubly carboxylated texaphyrin system in which the carboxyl groups are linked to the texaphyrin core via aryl ethers or functionalized alkyl substituents. The products of this scheme, compounds 14 H and 14 J could be converted to various esterified products wherein the ester linkages serve to append further hydroxyl-containing substituents. FIG. 15 summarizes the synthesis of polyhydroxylated texaphyrin derivatives via the use of secondary amide linkages. FIG. 16 summarizes the synthesis of another set of polyhydroxyl substituted texaphyrin derivatives using similar amide bonds as in FIG. 15. FIG. 17 summarizes the synthesis of saccharide substituted texaphyrins, wherein the saccharide moieties are appended via amide bonds. FIG. 18 summarizes the synthesis of polyhydroxylated texaphyrin derivatives containing branched polyhydroxyl (polyol) subunits appended to the texaphyrin core via aryl ethers. FIG. 19 summarizes how similar polyol subunits may be appended via ester linkages.

EXAMPLE 7

Derivatives of Texaphyrin having Different R Groups on the B Portion of the Molecule.

Figure 9:
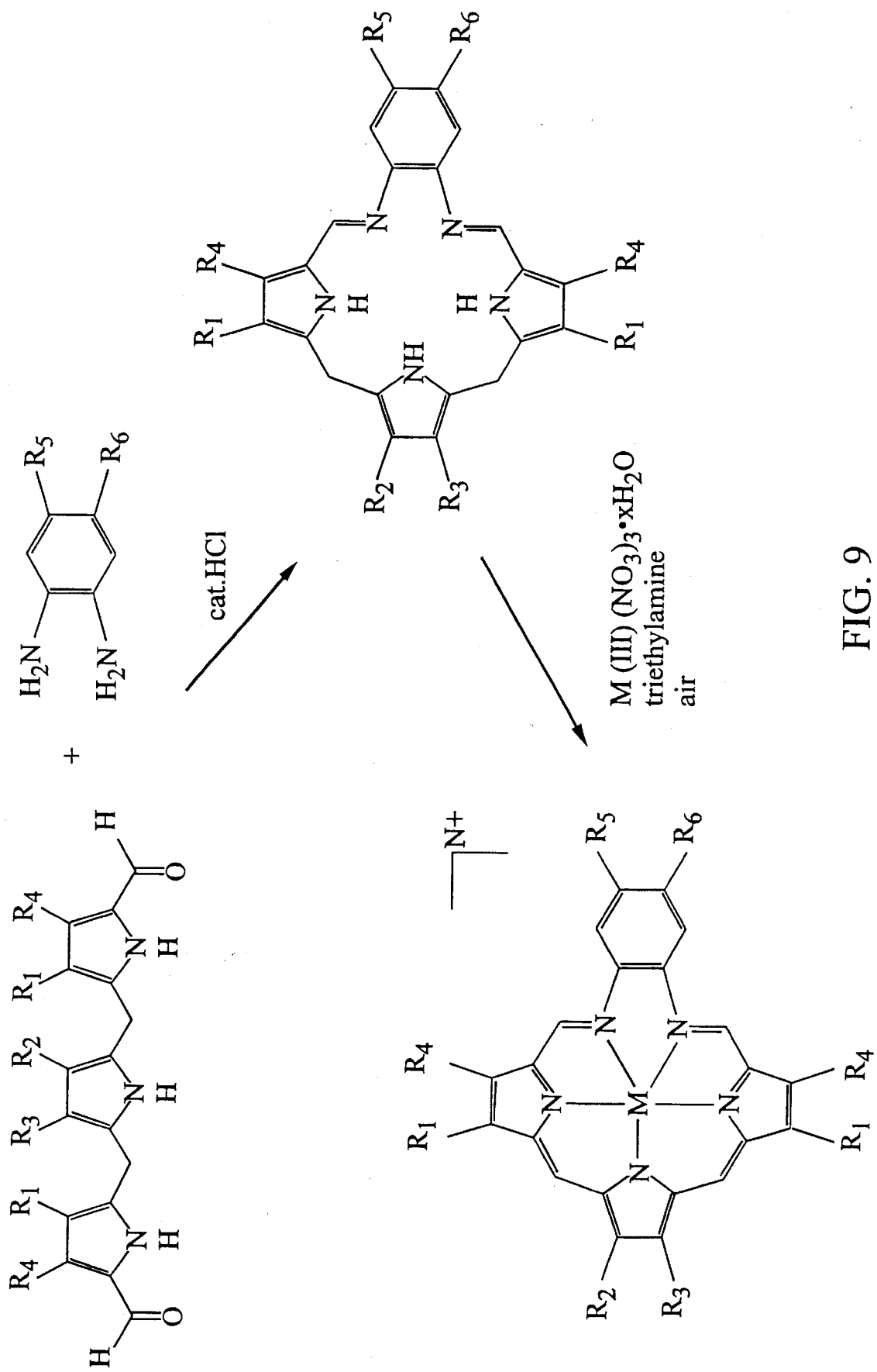
FIG. 9 shows the synthesis of texaphyrin metal complexes with different R groups on the B portion of the molecule.
Figure 10A:
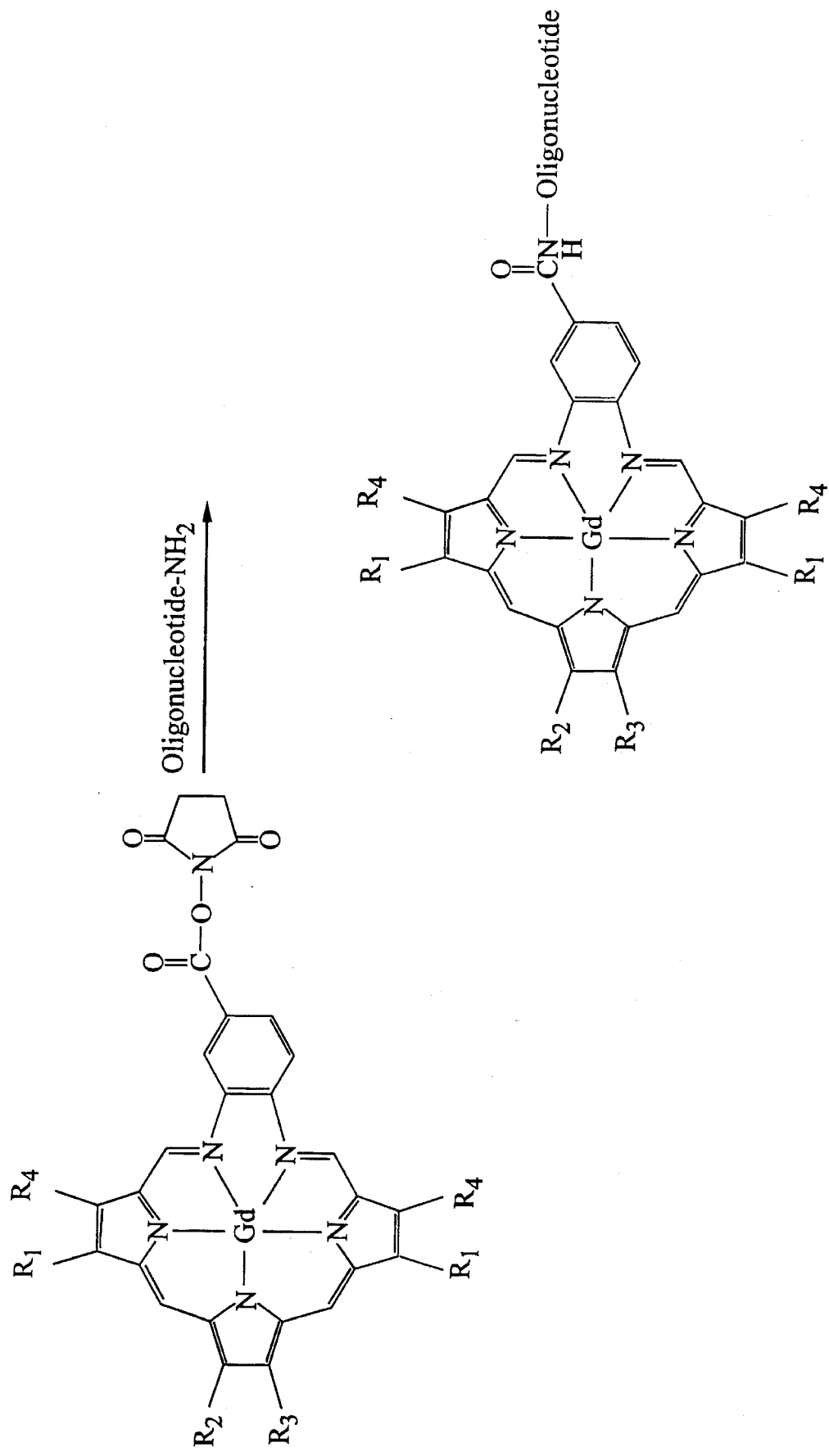
FIGS. 10A, 10B and 10C show covalent coupling of texaphyrin metal complexes with amine-, thiol- or hydroxy-linked oligonucleotides (10A), the synthesis of aminosaccharidetexaphyrin conjugates by ester-to-amide exchange (10B), and the synthesis of aminosaccharide-texaphyrin and oligopeptide texaphyrin conjugates by carbodiimide mediated reaction with carboxy-substituted. texaphyrins (10C).
Figure 10B:
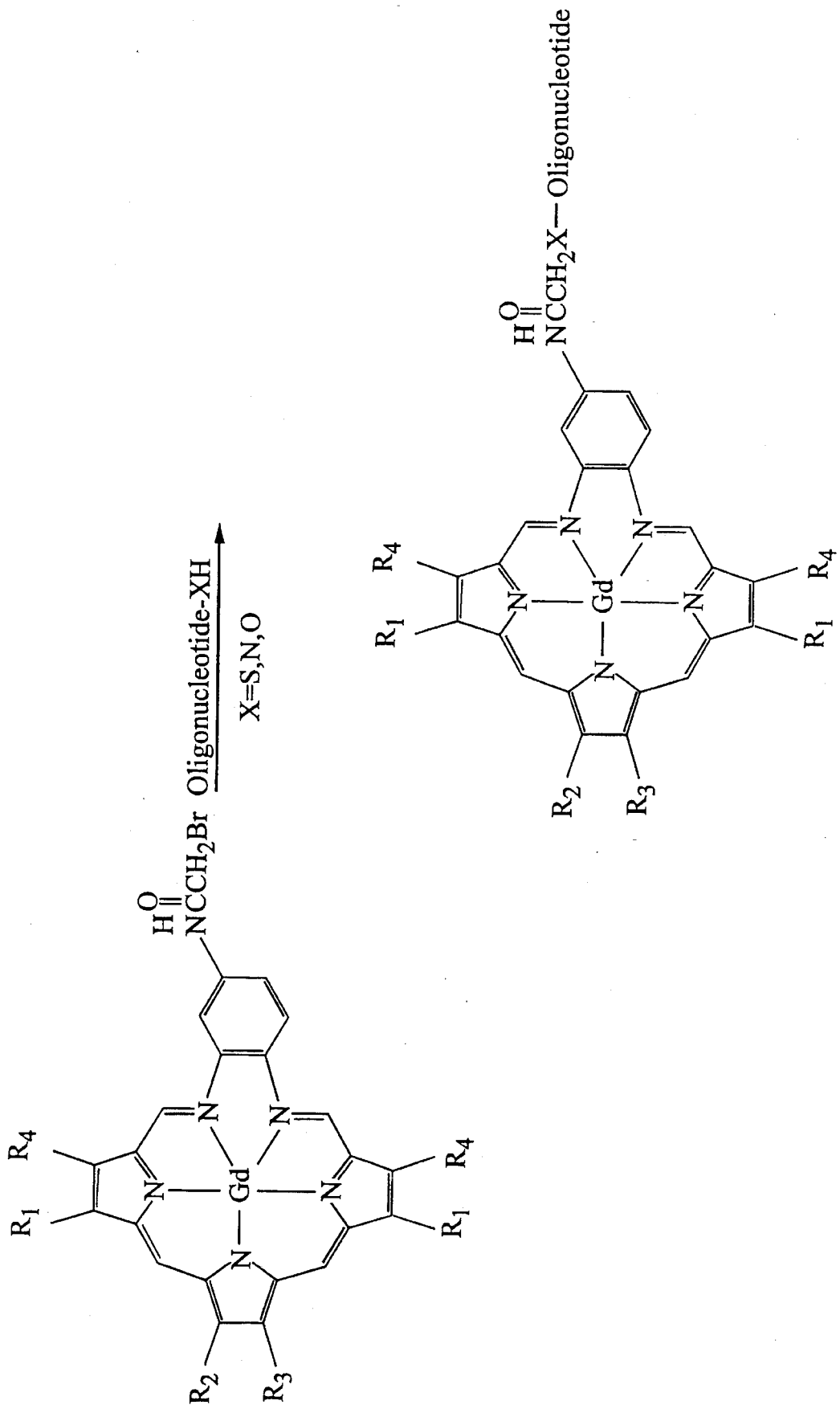
Figure 10C:
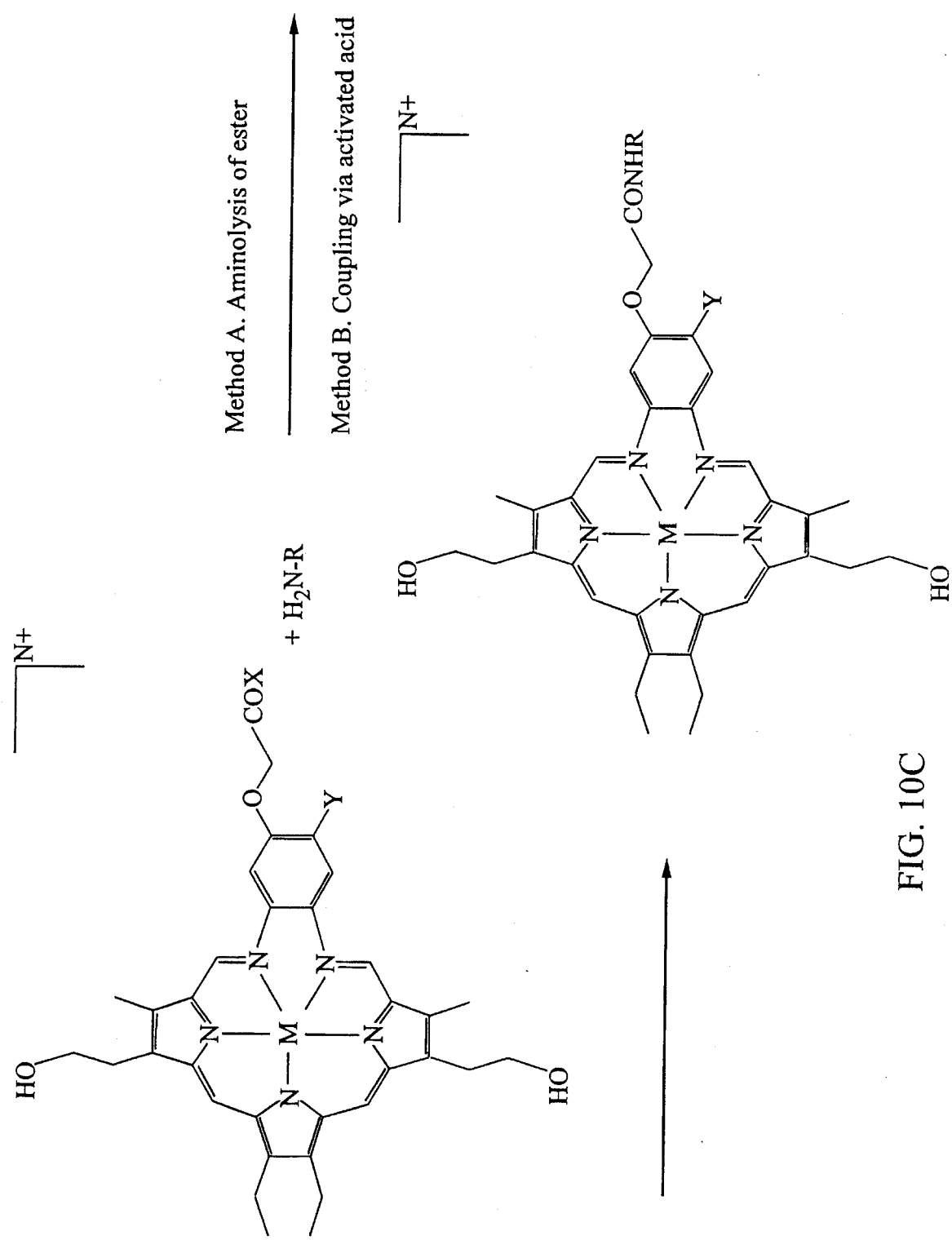
Figure 10D:
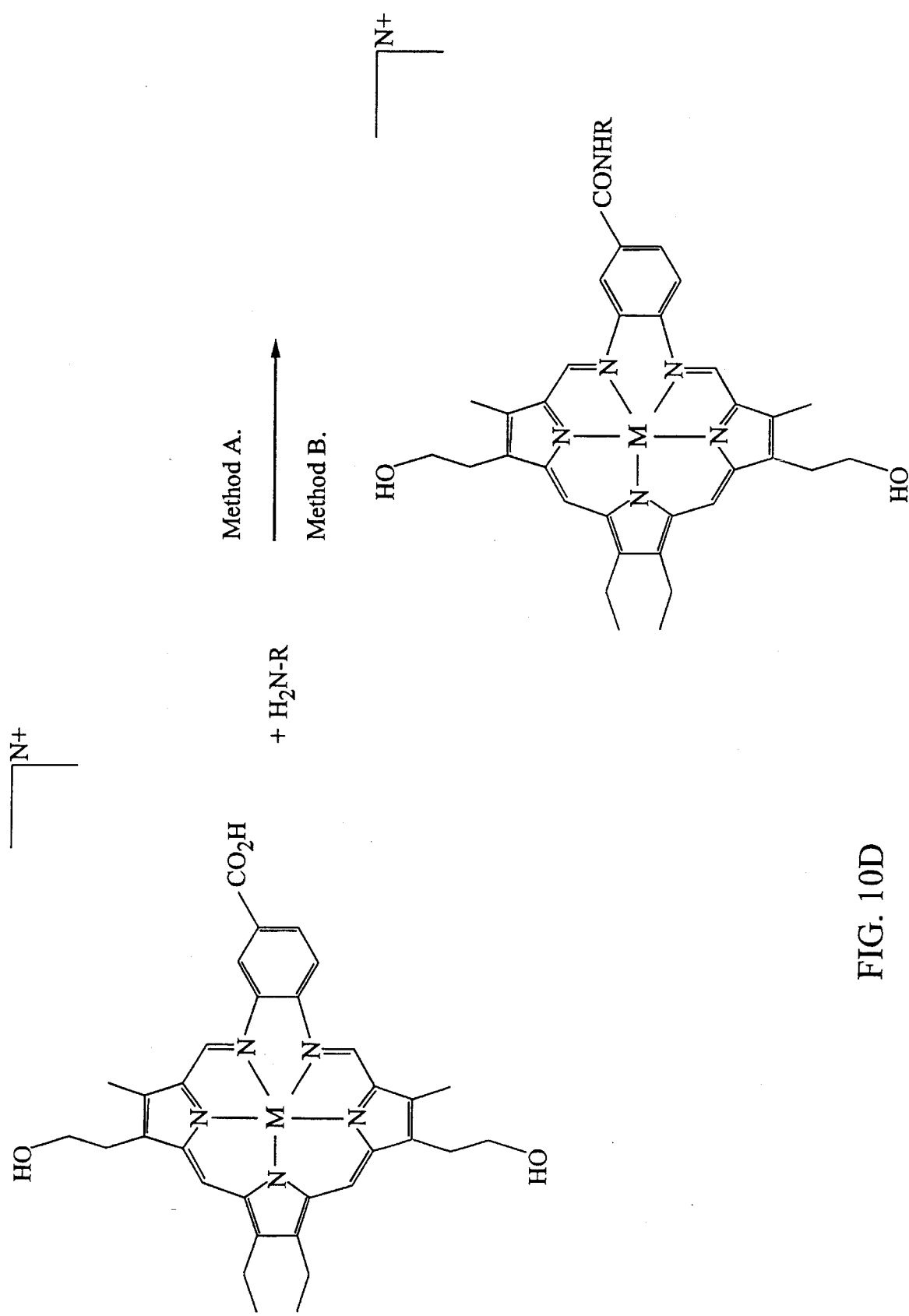
Figure 11A:
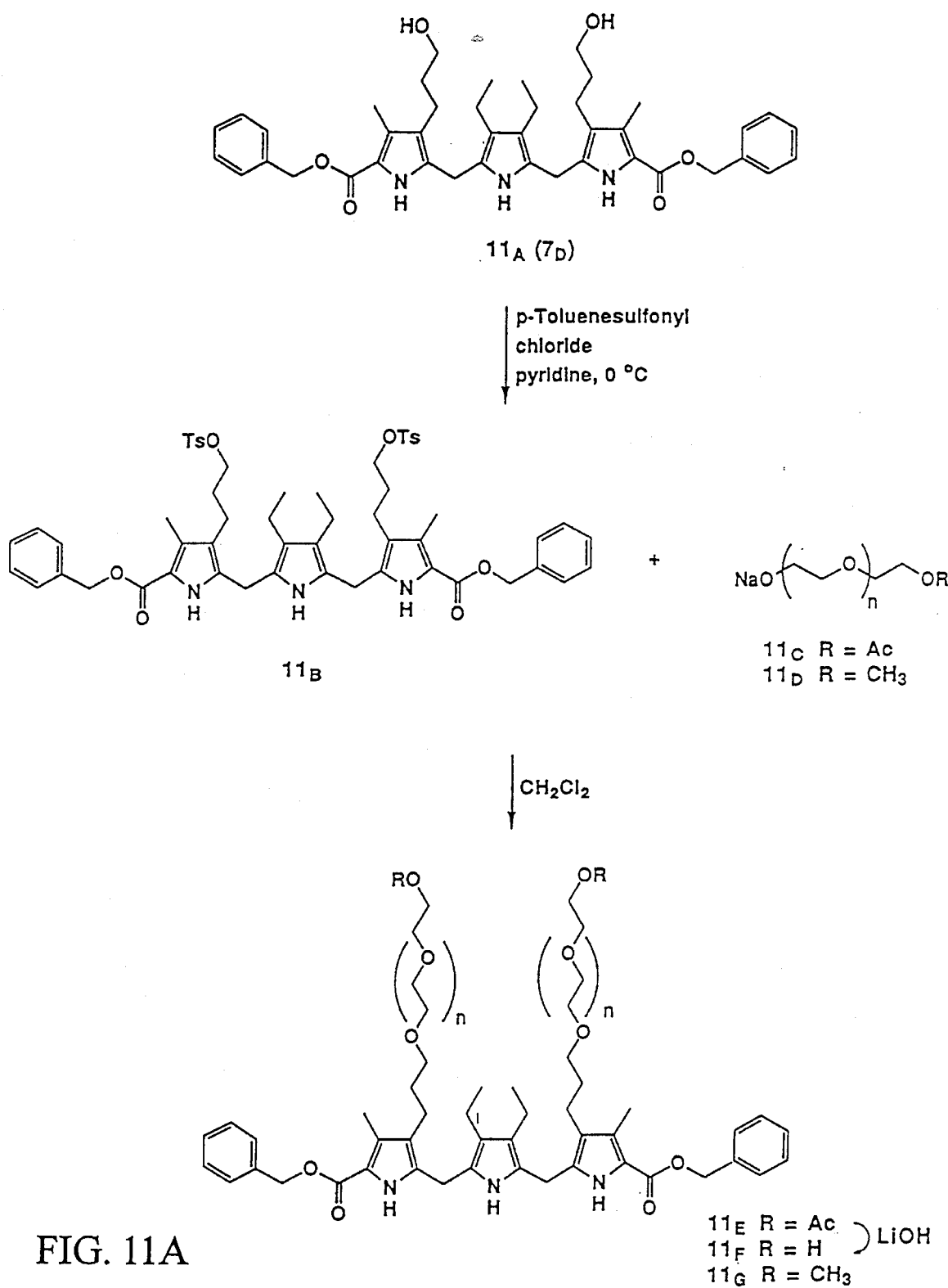
FIG. 11 summarizes the synthesis of polyether-linked polyhydroxylated teXaphyrins. Ts is a tosyl group.
Figure 11B:
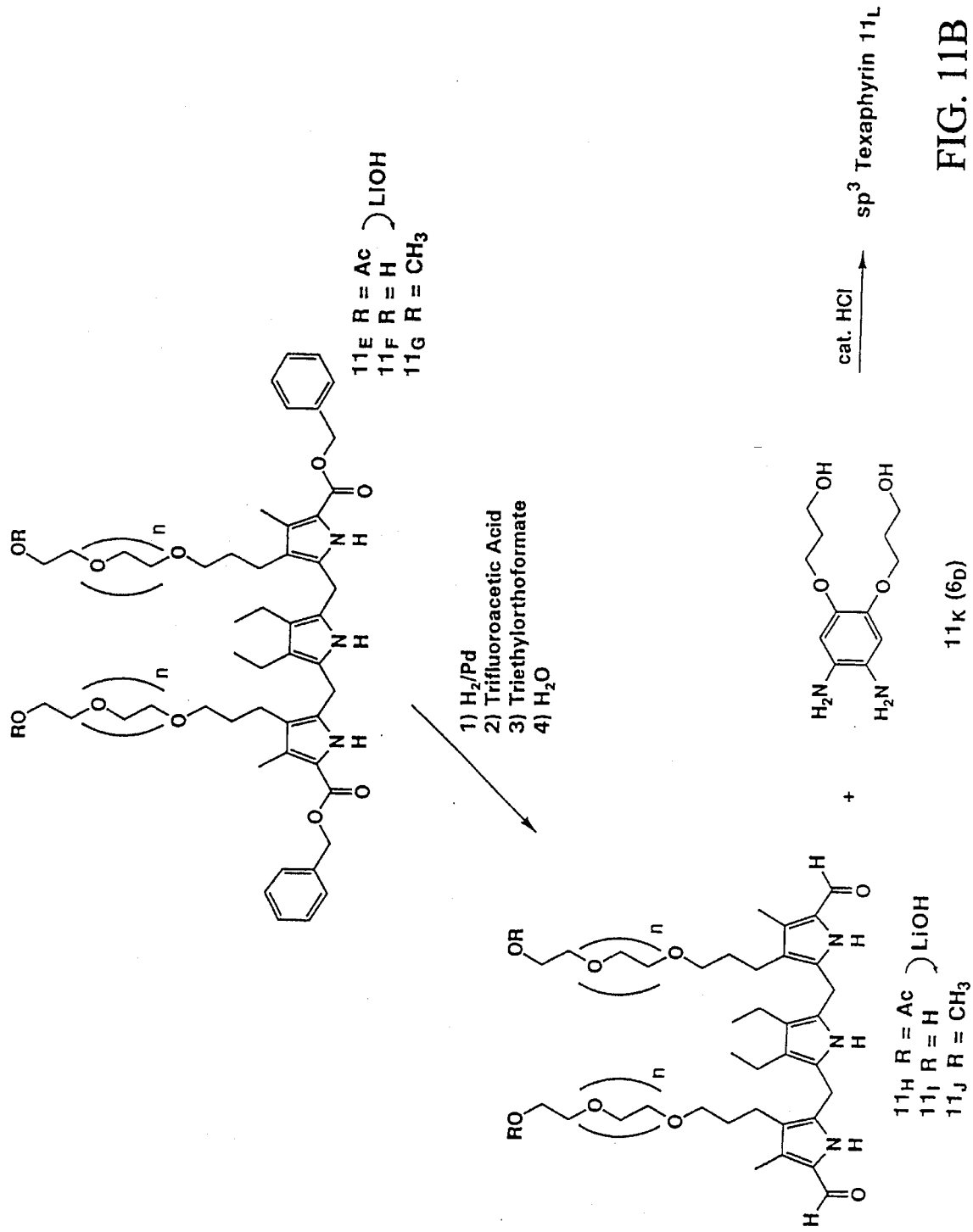
Figure 11C:
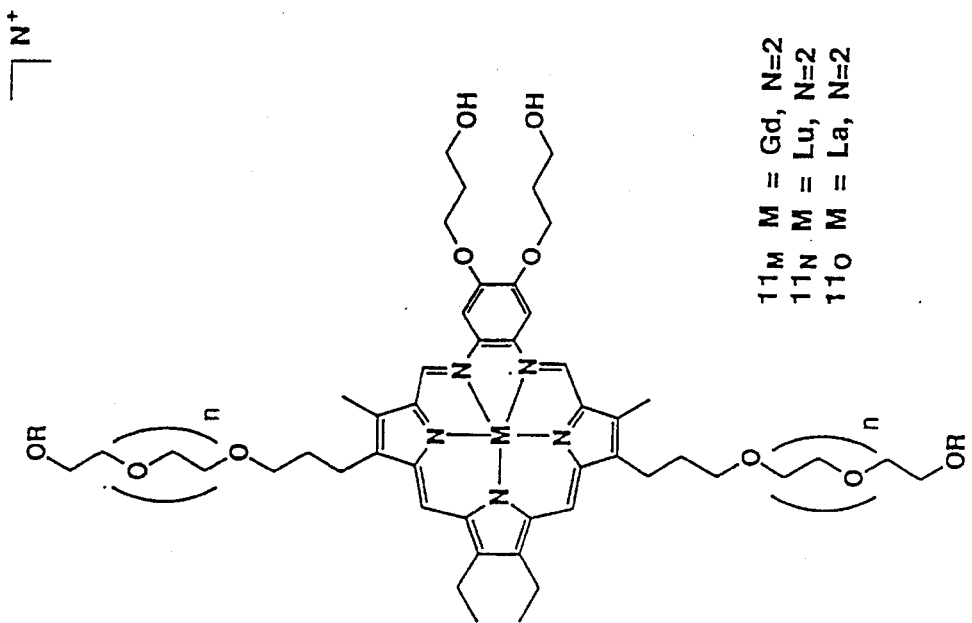
Figure 11C:
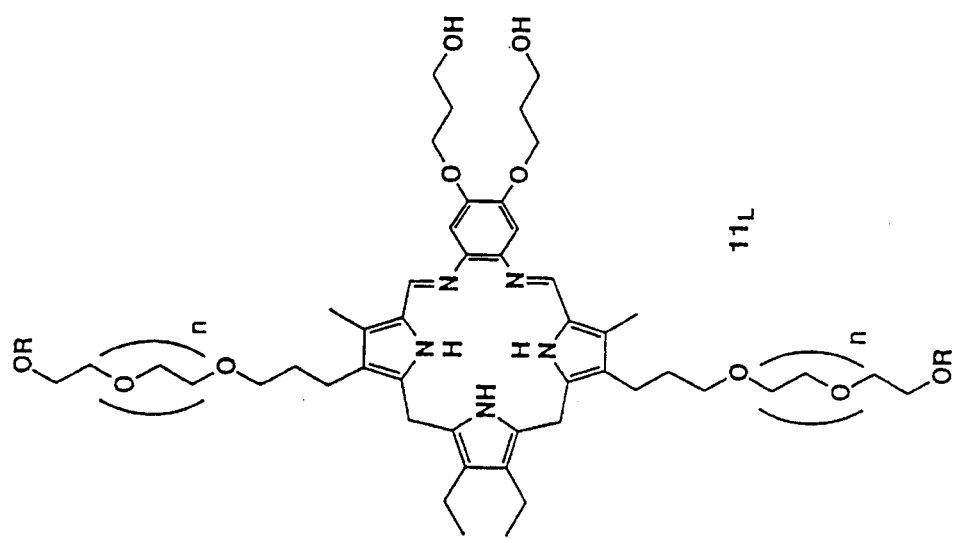

Texaphyrin macrocycles having a free carboxyl or a free amino group for further derivatization on the benzene ring portion of the molecule may be synthesized by replacing orthophenylenediamine with 3,4 diaminobenzoic acid or 3,4 diaminoaniline (FIG. 9). One skilled in the art of organic synthesis would realize that other substituted 1,2-o-phenylenediamines may be used as a precursor, e.g., a 1-2-o-phenylenediamine that is differentially substituted in the 4 and 5 positions. This substitution may be the result of different functionalities being present or specific protection and standard organic and/or biochemical transformations having been carried out. Such macrocycles can be further functionalized to the derivatives shown in FIG. 10.

The Synthesis of Aminosugar-Texaphyrin Conjugates by Ester-to-Amide Exchange. The synthetic strategy used to prepare aminosugar-texaphyrin conjugates is based on an ester-to-amide conversion of an appropriate starting texaphyrin methyl ester derivative shown as "Method A" in FIG. 10B. In a preferred embodiment, the texaphyrin methyl ester derivative contains this functionality on the benzene, or so-called "B", portion of the macrocycle and is linked to it by a spacer such as —OCH$_2$—. The amine used in the aminolysis is 1,2,3,4,6-tetra-O-acetyl-2-amino-2-deoxy-a-D-glucopyranose hydrobromide. With such preferred starting materials, one can achieve the desired ester to amide conversion by heating at reflux in an organic solvent such as methanol. Either during the course of this key synthesis step or as a separate transformation, the protecting groups on the sugar derivative are removed to yield the desired aminosugar-texaphyrin conjugate.

One of the advantages of this procedure is that the reaction is catalyzed by HBr normally complexed as its hydrobromide salt with the aminosugar component. Other advantages of this procedure are the solubility of both reaction components in methanol (or other organic solvents such as acetonitrile, DMF, DMSO, which one skilled in the art would appreciate can be used in place of methanol) and the high yield obtained in the coupling step. Finally, and perhaps most importantly, the resulting products are not only quite stable, they are also highly soluble in aqueous solution. The same procedure is applicable for other aminosugars, such as galactosamine, mannosamine, and aminooligosugar derivatives, as described in the following example.

The preparation of GdT2B (OCH$_2$CONHR) where R is glucosamine: A Texaphyrin-glucosamine Conjugate. The dihydroxyl, methyl ester substituted texaphyrin referred to as GdT2B(OCH$_2$CO$_2$CH$_2$) and shown as the starting material in FIG. 10B (91.2 mg. 0.1 mmol) was dissolved in absolute methanol under nitrogen. Tetra-O-acetylglucosamine hydrobromide (50 mg. 0.12 mmol) was added. The reaction mixture was subsequently heated at reflux under nitrogen for 6 hours before being allowed to cool to room temperature. After reaching room temperature (RT), the methanol was evaporated off under vacuum, the residue was resuspended in 50 ml of dichloromethane and stirred for 2 hours using a magnetic stirrer at RT. Any remaining free Gd(III) salts were removed using a zeolite with an appropriately sized set of cavities as the trapping agent. This was done by dissolving the crude product in methanol containing 10% water by volume, shaking for 10 hours with 5 g of the selected zeolite, filtering off the zeolite (now containing any free Gd(III) ions), and redrying under vacuum. The resulting product was then recrystallized from methanoldichloromethane (1:3 by volume). The yield of product so obtained is 99 mg, giving an overall yield of 85% for the combined, coupling, deprotection and purification steps. Characterization data: MS: FAB: 946 [MH$_3$]$^+$. HR MS: For C$_{40}$H$_{56}$N$_6$O$_9$Gd calcd. 946. 33524. Found 946. 33486. UV-Vis $\lambda_{max}$ (H$_2$O): 450,762.

Preparation of Oligopeptide-Texaphyrin Conjugates by Ester Saponification Followed by Carbodiimide Coupling. Starting from the same preferred texaphyrin methyl ester considered in the previous example, oligopeptide-texaphyrin conjugates may also be prepared. Here, as shown as Method B in FIG. 10B, the preferred embodiment entails an ester saponification step to liberate the free acid, followed by carbodiimide mediated condensation with the free amine group of an appropriate oligopeptide. In the preferred embodiment, the amine-containing oligopeptide is polylysine. Preferred coupling reagents are carbonyldiimidazole, mixed anhydrides, activated esters such a p-nitrophenyl, or NHS (N-hydroxysuccinimide) and the preferred reaction conditions are at neutral or near-neutral buffered aqueous solutions. The same procedure may be used to conjugate other oligopeptides such as (LysAla)n, (LysLeuAla)n, polyglutamic acid, polyornithine, oligosaccharides or polysaccharides such as heparin and the like to texaphyrins, as one skilled in the art can appreciate from the specific teachings contained in the example given below.

This procedure yields a texaphyrin derivative with desirable, high water solubility properties and allows for the possibility of specific targeting to different cells as a result of inherent protein-oligosaccharide immunological interactions. Since cancer cells display significant differences in the composition of their cell surface oligosaccharides as compared to normal cell membranes, these cancer cell surface oligosaccharides are expected to interact with peptides in a different way as compared to normal ones. The presently described approach may allow for the design of texaphyrin-oligopeptide (or texaphyrin-protein) conjugates that are selective for cancer cells as a result of these differential oligosaccharide-oligopeptide interactions.

Synthesis of Texaphyrin-poly-L-Lysine. The dihydroxyl, methyl ester substituted texaphyrin referred to as GdT2B(OCH$_2$CO$_2$CH$_2$) and shown specifically as the starting material in FIG. 10B (91.2 mg. 0.1 mmol) was dissolved/suspended in 3 ml of a 1M aqueous solution of a triethylammonim hydrogen carbonate buffer, pH 8.5, and stirred at RT for 2 days. (At this point, the hydrolysis/saponification of the ester was complete, as judged by MS and HPLC analysis). The solution was then cooled to 0° C. and the carbodiimide known as EDC (25 mg, 0.13 mmol) was added with stirring and the solution stirred at 0° C. for an additional 45 minutes. At this time, a solution (2 ml) of poly-L-lysine in water was added. The resulting mixture was then stirred for an additional 1 hour at 0° C. followed by an additional 1 day at RT. Following this, an additional equivalent of EDC (19.1 mg, 0.01 mmol) was added and again the mixture was allowed to stir at room temperature, this time for 2 days. Following this, the water was removed by evaporation under vacuum followed by trituration with and subsequent in vacuo removal of toluene (3× 20 ml). The resulting material was then washed with dichloromethane (30 ml) and dried under vacuum overnight. The product obtained in this way (93% yield) displays the characteristic UV-Vis spectrum of a metallated texaphyrin ($\lambda_{max}$:452,762 rim).

The Synthesis of Aminosugar-Texaphyrin and Oligopeptide Texaphyrin Conjugates by Carbodiimide Mediated Reaction with Carboxy-Substituted Texaphyrins. Both aminosugar-texaphyrin and oligopeptide-texaphyrin conjugates may be readily prepared using a carbodiimide mediated condensation of an aminosugar or an amine-containing oligopeptide, as appropriate, with a carboxy-substituted texaphyrin. In a preferred embodiment, the carboxy-substituted texaphyrin would contain this functionality on the benzene or so-called "B" portion of the macrocycle. Preferred coupling reagents would be carbonyldiimidazole, mixed anhydrides, activated esters such as p-nitrophenyl, or NHS (N-hydroxysuccinimide) and the preferred reaction conditions would be neutral or near-neutral buffered water solutions, DMF, or water-DMF mixtures.

This procedure may be used to conjugate oligopeptides such as (LysAla)$_n$, (LysLeuAla)$_n$, polyglutamic acid, polyornithine and the like to texaphyrins as well as other aminosugars, such as galactosamine, mannosamine, and amino-oligosugar derivatives. This procedure may generalized to prepare desired conjugates or congeners thereof using carboxy-substituted texaphyrins where the substituent is found elsewhere in the molecule. The following procedures, "Method A" and "Method B" refer to synthesis schemes in FIG. 10C.

Method A. In this method, 1,1'-carbonyldiimidazole is used as a coupling reagent: 1 mol. eq. of the carboxy-substituted texaphyrin shown in FIG. 10C (TX-CO2H) was dissolved in dry DMF. 1.1 mol. eq. of 1,1'-carbonyldiimidazole was added and the resulting mixture stirred under argon for 4 hours. The amino-component (1 mol. eq.) was dissolved in water-pyridine mixture (10:1), or in buffer (pH 8.5 or higher for optimum yields in the coupling) and slowly added to the solution of the now-activated carboxy-substituted texaphyrin component. The resulting reaction mixture was stirred at RT for 1–5 days (the reaction could be followed by HPLC analysis) or at 37° C. for 24 hours followed by evaporation at high vacuum, chromatographic purification, and/or recrystallization.

Method B. This method uses the carbodiimide known as EDC as the coupling reagent. The texaphyrin acid, TX-CO2H, (1 mol. eq.) was dissolved in dry DMF. The resulting solution was then cooled to 0° C. At this point the EDC carbodiimide (1.5 mol. eq.) and 3 mg of 1-hydroxybenzotriazole were added. The resulting mixture was then stirred at this temperature for 40 min. To the resulting solution, the amine containing component (1 mol. eq.) was added in aqueous buffer (pH 8.5). The resulting solution was kept at 0° C. for 1 hour and then stirred at RT for 2–5 days, with the course of the reaction being followed by HPLC, or reverse TLC. Following removal of solvent, the product was isolated by preparative HPLC.

EXAMPLE 8

A Derivative of Texaphyrin having an R Group on a Ring Nitrogen.

Figure 20:
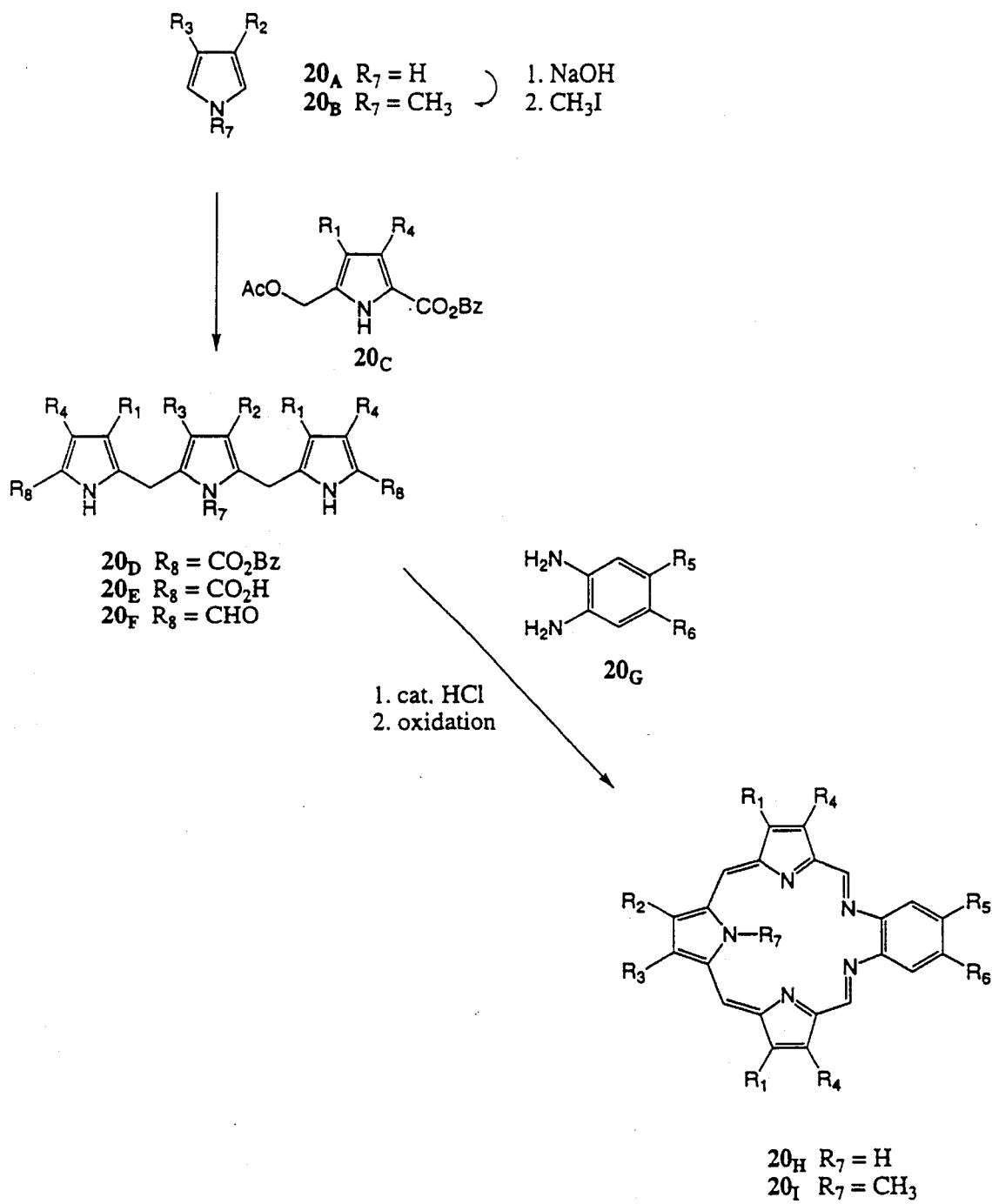
FIG. 20 shows the synthesis of a derivative of texaphyrin having an R group on a ring nitrogen $20_I$.

A further texaphyrin macrocycle is one in which a ring nitrogen is derivatized. FIG. 20 shows such an N-substituted texaphyrin where an $R_7$ group is attached to the central nitrogen of the precursor tripyrrole. $R_7$ may be a lower alkyl group, preferably a methyl group. The free base macrocycle would be particularly useful when fluorescence detection is used as the localization means for radiosensitization. Optical characteristics of various texaphyrin complexes are described in Sessler et al. (1991), incorporated by reference herein.

EXAMPLE 9

Derivatives of Texaphyrin having Four or more Hydroxyl Groups on the Tripyrrole Portion of the Molecule.

Figure 21:
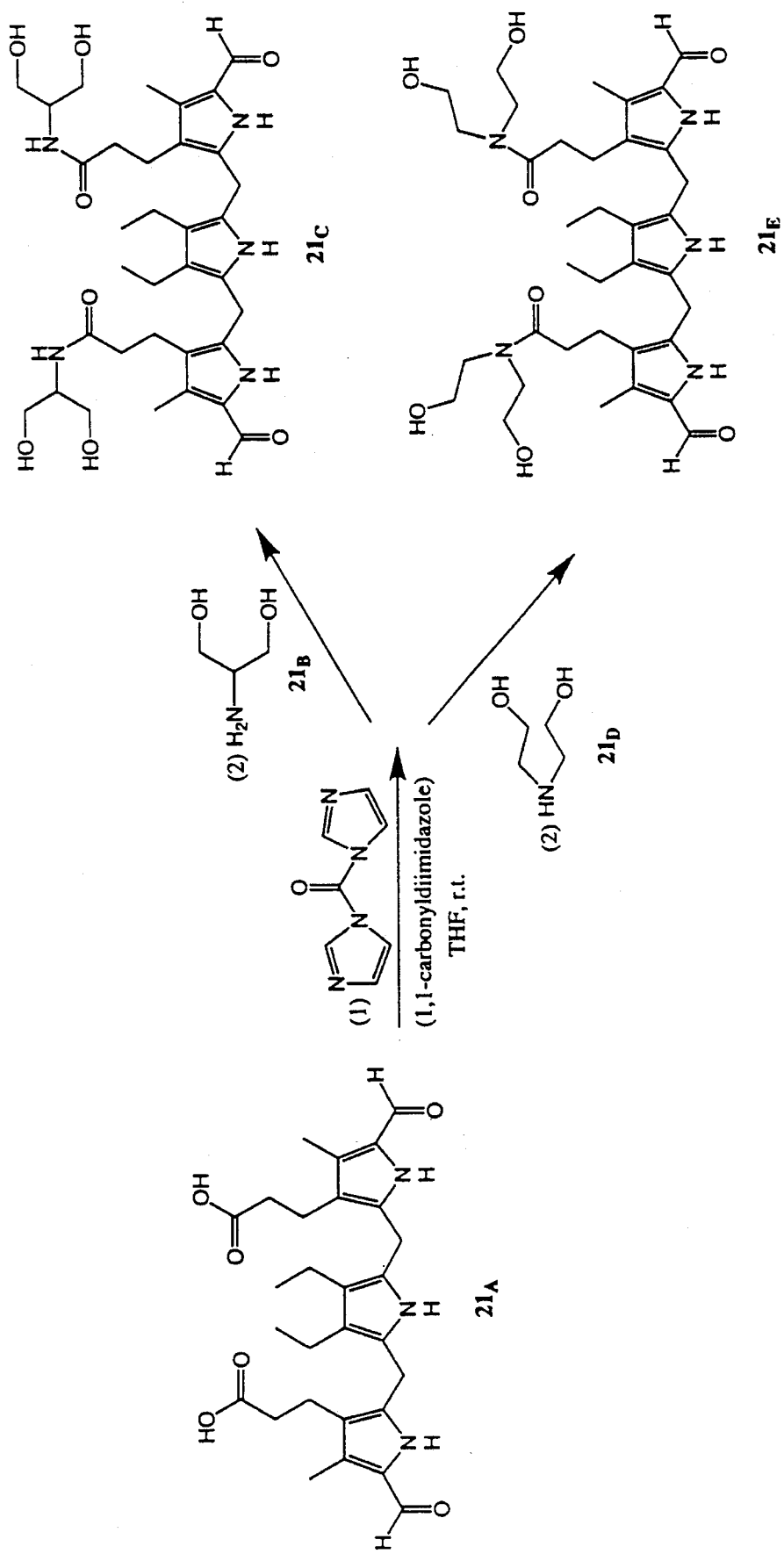
FIG. 21 summarizes the synthesis of a T4 tripyrrane dialdehyde using two different methods. Precursor $21_A$ is derivatized with serinol in the presence of 1,1'-carbonyldiimidazole to form $21_C$; Precursor $21_A$ is derivatized with diethanolamine to form $21_E$.

Preparation of T4 tripyrrane dialdehyde, serinol derived, FIG. 21A. A tripyrrane dialdehyde $21_C$ having four hydroxyls on the periphery may be synthesized as indicated in FIG. 21A using the dicarboxylic acid derived tripyrrane dialdehyde $21_A$ and serinol $21_B$ upon initial in situ activation with 1,1-carbonyldiimidazole.

Preparation of T4 tripyrrane dialdehyde, diethanolamine derived FIG. 21B. A tripyrrane dialdehyde $21_E$ having four hydroxyls on the periphery may be synthesized as indicated in FIG. 21B using the dicarboxylic acid derived tripyrrane dialdehyde $21_A$ and diethanolamine $21_D$ upon initial in situ activation with 1,1-carbonyldiimidazole.

Figure 22:
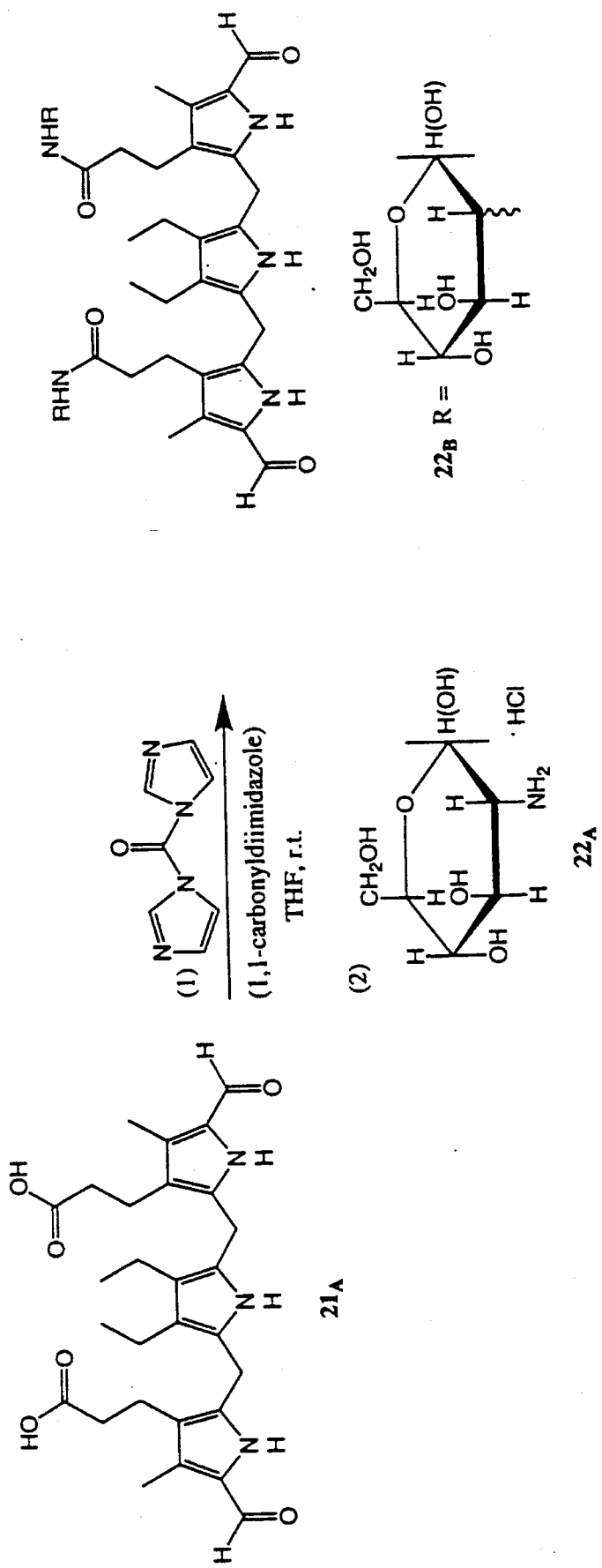
FIG. 22 summarizes the synthesis of a T8 tripyrrane dialdehyde. Precursor $21_A$ is derivatized with D-glucosamine.HCl in the presence of 1,1'-carbonyldiimidazole to form $22_E$.
Figure 23:
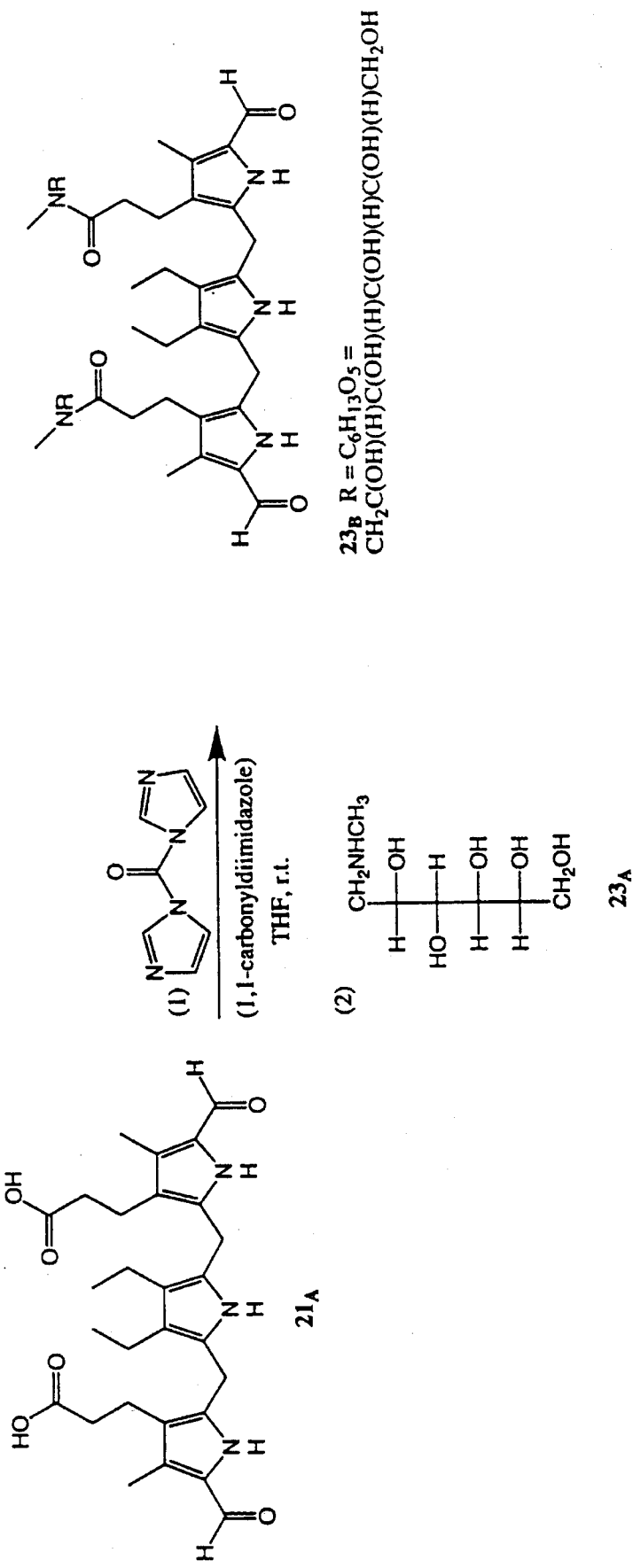
FIG. 23 summarizes the synthesis of a T10 tripyrrane dialdehyde. Precursor $21_A$ is derivatized with N-methylglucamine in the presence of 1,1'-carbonyldiimidazole to form $23_B$.

Preparation of T8-T10 tripyrrane dialdehyde, FIGS. 22 and 23, glucosamine derived. A tripyrrane dialdehyde $22_B$ having eight hydroxyls on the periphery may be synthesized as indicated in FIG. 22 using the dicarboxylic acid derived tripyrrane dialdehyde $21_A$ and D-glucosamine hydrochloride $22_A$ upon initial in situ activation with 1,1-carbonyldiimidazole.

Preparation of T8-T10 tripyrrane dialdehyde, N-methylglucamine derived. A tripyrrane dialdehyde $23_B$ having ten hydroxyls on the periphery may be synthesized as indicated in Figure23 using the dicarboxylic acid derived tripyrrane dialdehyde $21_A$ and N-methyl-D-glucamine $23_A$ upon initial in situ activation with 1,1-carbonyldiimidazole.

Figure 24:
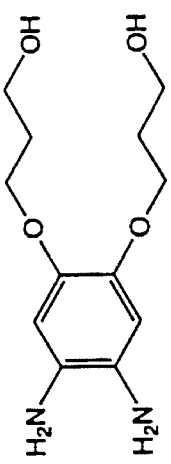
FIG. 24 shows diamines for reacting with tripyrrane dialdehydes to form sp³ macrocycles.
Figure 24:
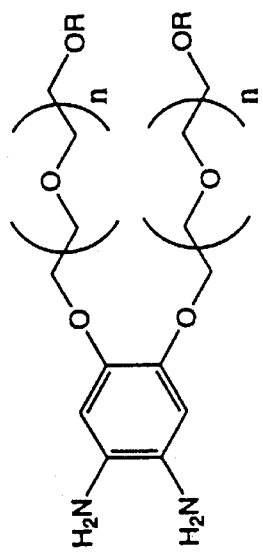
Figure 24:
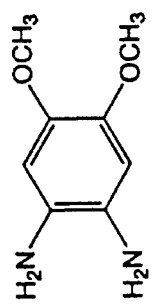
Figure 24:
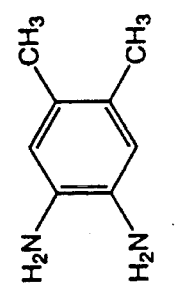
Figure 24:
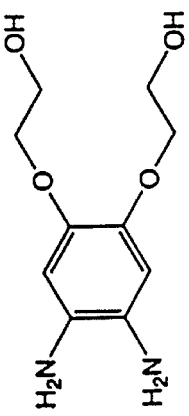

One skilled in the art would understand that depending on the nature of the linking group, the saccharide moiety may be in equilibrium between the straight chain form and the pyranose form of the molecule, therefore between 8–10 free hydroxyls may be present on the molecule at equilibrium. Representative diamines for reacting with dialdehydes to synthesize texaphyrin macrocycles are shown in FIG. 24.

Preparation of a T4 macrocycle. A texaphyrin macrocycle having four hydroxyls on the tripyrrane portion of the molecule may be synthesized as indicated in FIG. 9 using the tripyrrane dialdehyde $21_C$ and the diamine $24_A$ to form $25_A$ (FIG. 25A); $21_C$ may be combined with $24_B$ to form $25_B$; $21_E$ may be combined with $24_A$ or $24_B$ to form $25_C$ or $25_D$, T4 macrocycles.

Preparation of a T6 macrocycle. The tripyrrane dialdehyde $21_C$ may be combined with diamine $24_C$ to form $26_A$ (FIG. 26A), a texaphyrin with 4 hydroxyls on the T portion and 2 on the B portion of the molecule. Similarly, reaction with diamine $24_D$ would yield a B2T4 macrocycle one carbon chain longer at positions $R_5$ and $R_6$ (FIG. 9, FIG. 26A).

Tripyrrane dialdehyde $21_C$ may be reacted with diamine $24_E$ to form $26_C$ or diamine $24_F$ to form $26_D$, a T4 or a T4B2 macrocycle, respectively. In structure $24_E$ or $24_F$, n is a whole number between 0 and 100. Tripyrrane dialdehyde $21_E$ may be combined with $24_C$ or $24_D$ to form $26_E$ or $26_F$, T4B2 macrocycles (FIG. 26A).

Tripyrrane dialdehyde $21_E$ may be combined with $24_E$ or $24_F$ to form $26_G$ or $26_H$, a T4 or a T4B2 macrocycle, respectively (FIG. 26A).

Preparation of T8-T12 macrocycles. Tripyrrane dialdehyde $22_B$ may be reacted with $24_A$ or $24_B$ to form $27_A$ or $27_B$ (FIG. 27A). Tripyrrane dialdehyde $22_B$ may be reacted with $24_E$ or $24_F$ to form $28_C$ or $28_D$ (FIG. 28A). Tripyrrane dialdehyde $22_B$ may be reacted with $24_C$ or $24_D$ to form $28_A$ or $28_B$ (FIG. 28A). Tripyrrane dialdehyde $23_B$ may be reacted with $24_A$ or $24_B$ to form $29_A$ or $29_B$ (FIG. 29A). Tripyrrane dialdehyde $23_B$ may be reacted with $24_E$ or $24_F$ to form $30_C$ or 3% (FIG. 30A). Tripyrrane dialdehyde $23_B$ may be reacted with $24_C$ or $24_D$ to form $30_A$ or $30_B$ (FIG. 30A).

EXAMPLE 10

Texaphyrin Conjugates to Site-Directed Molecules for Radiosensitization and Texaphyrins as an Internal Radioactive Source The use of texaphyrins as radiosensitizers in vivo as part of a treatment procedure relies on the effective localization of the complex to the treatment site. This localization may occur by conjugating the texaphyrin metal complex to a site-directed molecule such as an antibody, a peptide having affinity for a biological receptor, to a dye or other compound having binding specificity for a target, to a sequence-specific oligonucleotide, or localization may rely on the intrinsic biolocalization properties of the texaphyrins as discussed in Example 11.

Texaphyrins are especially suited for acting as bifunctional chelating agents in antibody conjugate-based treatment since they have functional groups suitable for conjugation to the antibody. They form covalent linkages that are stable in vivo which do not destroy the immunological competence of the antibody, they are relatively nontoxic, they bind metals and retain the metal of interest under physiological conditions, and they are readily soluble in a physiological environment. A further advantage of these texaphyrins is that many would be suitable for further functionalization. Treatment of carboxylated texaphyrins with thionyl chloride or p-nitrophenol acetate would generate activated acyl species suitable for attachment to monoclonal antibodies or other biomolecules of interest. Standard in situ coupling methods (e.g. 1,1'-carbonyldiimidazole (CDI) could be used to effect the conjugation.

The selectivity of the texaphyrins may be enhanced by covalently linking oligonucleotides onto the periphery of the macrocycle. Amides, ethers and thioethers are representative of linkages which may be used for this purpose (see FIG. 10). Oligonucleotides functionalized with amines at the 5'-end, the 3'-end, or internally at sugar or base residues may be modified post-synthetically with an activated carboxylic ester derivative of the texaphyrin complex. Alternatively, oligonucleotide analogs containing one or more thiophosphate or thiol groups may be selectively alkylated at the sulfur atom(s) with an alkyl halide derivative of the texaphyrin complex. The resultant oligodeoxynucleotide-complex conjugates may be designed so as to provide optimal catalytic interaction between a target nucleic acid and the bound texaphyrin. The oligonucleotide may be large enough to bind probably at least 15 nucleotides of complementary nucleic acid.

A general method for preparing oligonucleotides of various lengths and sequences is described by Caracciolo et al. (1989) Science, 245:1107.

In general, there are two commonly used solid phase-based approaches to the synthesis of oligonucleotides containing conventional 5'-3' linkages, one involving intermediate phosphoramidites and the other involving intermediate phosphonate linkages. In the phosphoramidite synthesis a suitably protected nucleotide having a cyanoethylphosphoramidate at the position to coupled is reacted with the free hydroxyl of a growing mucleotide chain derivatized to a solid support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate diester linkage, which is stable to acid Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less sufficient for oligonucleotides of any substantial length.

Preferred oligonucleotides resistant to in vivo hydrolysis may contain a phosphorothioate substitution at each base (*J. Org. Chem.*, 55:4693–4699, (1990) and Agrawal, (1990). Oligodeoxynucleotides or their phosphorothioate analogues may be synthesized using an Applied Biosystem 380B DNA synthesizer (Applied Biosystems, Inc., Foster City, Calif.).

Another means of gaining selectivity may be to covalently link the texaphyrin complex to a sapphyrin (sap) molecule, (Sessler et al., 1992; Furuta et al., 1991; Sessler et al., 1991; U.S. Pat. Nos. 5,159,065; 5,120,411; 5,041,078). Since sapphyrins bind DNA, $K\sim10^6M^{-1}$, (U.S. Ser. No. 07/964, 607, incorporated by reference herein) the linked texaphyrin-sapphyrin complex (txph-sap) could effectively increase the texaphyrin concentration at locations adjacent to the sapphyrin binding sites. Sapphyrins have a higher fluorescent quantum yield than texaphyrins, allowing greater fluorescence detection. A laser system may be employed where the molecules are optimized to the laser wavelength; an excited sapphyrin may transfer its energy to the conjugated texaphyrin for detection. The texaphyrin molecule may further be designed to pass through cell membranes for selective radiosensitization.

Radioisotopes play a central role in the detection and treatment of neoplastic disorders. Improving their efficacy in medical applications involves attaching radioisotopes to tumor-directed molecules. For example, radiolabeled antibodies could serve as "magic bullets" and allow the direct transport of radioisotopes to neoplastic sites thus minimizing whole body exposure to radiation. The use of bifunctional metal chelating agents in radioimmunodiagnostics (RID), radiosensitization and therapy (RIT) is most closely related to the present invention. In these procedures, the radiometal of interest must be bound and retained under physiological conditions. The potential damage arising from "free" radioisotopes, released from the complex, can be very serious. The advantage of a chelate, such as a texaphyrin metal complex, that does not allow for metal release is clear.

For the purposes of imaging, an ideal isotope should be readily detectable by available monitoring techniques and induce a minimal radiation-based toxic response. In practice these and other necessary requirements implicate the use of a γ-ray emitter in the 100 to 250 KeV range, which possesses a short effective half-life (biological and/or nuclear), decays to stable products, and, of course, is readily available under clinical conditions. To date, therefore, most attention has focused on $^{131}I$ ($t_{1/2}$=193h), $^{123}I$ ($t_{1/2}$=13h), $^{99m}Tc$($t_{1/2}$=6.0 h), $^{67}Ga$($t_{1/2}$=78h), and $^{111}In$($t_{1/2}$=67.4h) which come closest to meeting these criteria. Each of these enjoys advantages and disadvantages with respect to antibody labeling for RID. $^{131}I$ and $^{123}I$, for instance, are easily conjugated to antibodies via electrophilic aromatic substitution of tyrosine residues. The metabolism of $^{131}I$ or $^{123}I$ labeled proteins, however, produces free radioactive iodide anion and as a result can lead to a fair concentration of radioactivity at sites other than those targeted by the antibody-derived "magic bullet". The half-lives of both $^{131}I$ and $^{123}I$ are relatively inconvenient for optimal use, being too long and too short, respectively, and the fact that $^{131}I$ is also a β emitter. $^{99m}Tc$, $^{67}Ga$, and $^{111}In$ all suffer from the disadvantage that they cannot be bound directly to the antibody in a satisfactory fashion and require the use of a bifunctional conjugate. The chemistry of such systems is furthest advanced in the case of $^{99m}Tc$, and a number of effective ligands, are now available for the purpose of $^{99m}Tc$ administration. This radioisotope has a very short half-life which makes it technically very difficult to work with. Both $^{67}Ga$ and $^{111}In$ have longer half-lives and possess desirable emission energies. Both are "hard" cations with high charge density in their most common trivalent forms. No suitable ligands exist for either $^{111}In^{3+}$ or $^{67}Ga^{3+}$ which form stable nonlabile complexes and which might be suitable for radioimmunological applications. As described elsewhere herein texaphyrin forms a kinetically and hydrolytically stable complex with $In^{3+}$. Such a ligand system may be elaborated and serve as the critical core of a bifunctional conjugate for use in $^{111}In$-based RID.

Many of the same considerations hold true for radioisotope-based therapy as do for radioisotope-based diagnostics: An ideal isotope must also be readily available under clinical conditions (i.e. from a simple decay-based generator), possess a reasonable half-life (i.e. on the order of 6 hours to 4 weeks), and decay to stable products. In addition, the radioisotope must provide good ionizing radiation (i.e. in the 300 KeV to 3 MeV range). A number of β emitters, including $^{131}I$, are currently receiving attention as possible candidates for RIT. Among the more promising, are $^{186}Re$ ($t_{1/2}$=90 h, $^{67}Cu$ ($t_{1/2}$=58.5 h), and $^{90}Y$ ($t_{1/2}$=65 h). Of these, $^{90}Y$ is currently considered the best, with an emission energy of 2.28 MeV, it is calculated to deliver roughly 3 to 4 times more energy (dose) to the tumor per nanomole than either $^{186}Re$ or $^{67}Cu$. Good immuno-compatible chelands exist for only $^{186}Re$ and $^{67}Cu$, the former may be attached using the same ligands as were developed for $^{99m}Tc$, and the latter via the rationally-designed activated porphyrins developed by Prof. Lavallee of Hunter College and the Los Alamos INC-11 team. Further benefits should be derived from a bifunctional conjugate which is capable of forming stable, nonlabile complexes with $^{90}Y^{3+}$ (which cannot be done with porphyrins). The texaphyrin ligand of the present invention not only forms stable complexes with $In^{3+}$ but also binds $Y^{3+}$ effectively. A texaphyrin-type bifunctional conjugate may be prepared for use in $^{111}In$-based RID and in $^{90}Y$-based RIT. Both $^{90}Y$ and $^{111}In$ could conceivably be attached to an antibody of choice using a functionalized texaphyrin. The $Y^{3+}$ and $In^{3+}$ complexes of texaphyrin are formed rapidly (insertion and oxidation times are less than 3 hours) from the methylene-linked reduced precursor, and are hydrolytically stable in 1:1 methanol-water mixtures (the half-lives for decomplexation and/or ligand decomposition exceed 3 weeks in both cases. $^{153}Gd$ is primarily a gamma emitter and is a preferred paramagnetic metal for magnetic resonance imaging. $^{153}GdB2T2$ localizes to the liver and would be a preferred metal complex for use as a tracer for pharmacokinetic studies.

The hydroxy-substituted texaphyrin molecules of the present invention are suited for delivering radioactivity to a tumor on their own since they chelate radioisotopes and have intrinsic biolocalization selectivity. This intrinsic biolocalization is described in Example 11. A texaphyrin complexed to $^{90}Y$ may be administered in combination with another texaphyrin complexed to a diamagnetic metal for photodynamic tumor therapy, for example, to achieve a synergistic killing of malignant cells.

EXAMPLE 11

Hydroxy-Substituted Texaphyrins for Imaging.

In many respects the key to cancer control lies in early detection and diagnosis as it does in subsequent therapeutic management. New techniques which allow neoplastic tissue to be observed and recognized at an early stage of development thus have a critical role to play in the battle against these disorders. One such promising technique is magnetic resonance imaging (MRI). Although quite new, this noninvasive, apparently innocuous method, is now firmly entrenched as a diagnostic tool of prime importance, complementing or, in some cases, supplanting computer assisted X-ray tomography as the method of choice for solid tumor detection.

The physical basis of current MRI methods has its origin in the fact that in a strong magnetic field the nuclear spins of water protons in different tissues relax back to equilibrium at different rates. When these local, tissue-dependent relaxation differences are large, tissue differentiation can be effected. Paramagnetic compounds, containing one or more unpaired spins, enhance the relaxation rates for the water protons in which they are dissolved. The extent of this enhancement is termed relaxivity. At present, only one paramagnetic MRI contrast agent is in clinical use, the bis(N-methyl-glucamine) salt of Gd(III) diethylenetriaminepentaacetate, $(MEG)_2[Gd(DTPA)(H_2O)]$ marketed by Berlex Laboratories. This dianionic complex localizes selectively in extracellular regions, and is being used primarily in the visualization of the capillary lesions associated with cerebral tumors.

Considerable effort has been devoted to the development of new potential MRI contrast agents. Most of this work has centered around preparing new complexes of Gd(III). The emphasis on Gd(III) salts stems from the fact that this cation, with 7 unpaired f-electrons, has a higher magnetic moment than other paramagnetic cations such as Fe(III) and Mn(II). Thus, complexes of Gd(III) would be expected to be superior relaxation agents than those derived from Mn(II) or Fe(III). In addition, both iron and, to a lesser extent, manganese are sequestered and stored very efficiently in humans (and many other organisms) by a variety of specialized metal-binding systems. Moreover both iron and manganese are capable of existing in a range of oxidation states and are known to catalyze a variety of deleterious Fenton-type free-radical reactions. Gadolinium(III), which suffers from neither of these deficiencies, thus appears to offer many advantages. As is true for Fe(III) and Mn(II), the aqueous solution of Gd(III) is too toxic to be used directly for MRI imaging at the 0.01 to 1 mM concentrations required for effective enhancement. Hence the emphasis is on developing new agents which, as is true for DTPA, form hydrolytically stable complexes in vivo with Gd(III) and/or other paramagnetic cations. A number of such ligands, including the very promising DOTA and EHPG systems, are now known. In almost all cases, however, reliance is made on the same basic philosophical approach. Specifically, for Gd(III) binding, carboxylates, phenolates, and/or other anionic chelating groups are being used to generate intrinsically labile complexes of high thermodynamic stability in the hope that such high thermodynamic stability will translate into a kinetic stability that is sufficient for in vivo applications. Little effort is currently being devoted to the preparation of nonlabile Gd(III) complexes that would in and of themselves enjoy a high kinetic stability. The problem seems to be quite simply that such systems are hard to make. For instance, unlike the transition metal cations which are bound well to porphyrins (a synthetically versatile ligand which is readily subject to modification and which, at least for [Mn(III)TPPS], and other water soluble analogues, shows good relaxivity and good tumor localizing properties), Gd(III) forms only weak and/or hydrolytically unstable complexes with porphyrins, although other simple macrocyclic amine- and imine-derived ligands will support stable complexes with certain members of the lanthanide series and do show some promise, as yet unrealized, of acting as supporting chelands for Gd(III)-based MRI applications.

According to the present invention nonlabile Gd(III) complexes of hydroxy-substituted texaphyrins prove to be useful contrast agents for MRI applications. Hydroxy-substituted texaphyrins are capable of stabilizing complexes with a variety of di- and trivalent cations, including $Cd^{2+}$, $Hg^{2+}$, $Lu^{+3}$, $Gd^{+3}$, and $La^{+3}$. Such complexes are particularly soluble in physiological environments.

Magnetic Resonance Imaging with B2T2 in vivo

The T2B2 gadolinium complex showed low toxicity and good tissue selectivity in magnetic resonance imaging enhancement.

Imaging: Scanning was performed using a circumferential transmit/receive coil (Medical Advances, Milwaukee, Wisc.) in the bore of a 1.5 Tesla Signa scanner (GE Medical Systems, Milwaukee, Wisc.). Normal male Sprague-Dawley rats (n=5) weighing from 280–320 grams and rats bearing subcutaneously implanted methylcholanthrene-induced fibrosarcomas in their left flanks (n=4) were studied. Tumor size at the time of the study ranged from 2.5 to 3.5 cm in widest diameter. The rats were anesthetized with 90 mg/kg of ketamine (Vetalar, Aveco Corporation, Fort Dodge, Iowa) and 10 mg/kg of xylazine (Rompun, Mobay Corporation, Shawnee, Kans.) intraperitoneally. Following the insertion of an intravenous catheter in the tail vein, each animal was placed in supine (normal rats) or prone (tumor-bearing rats) position in the center of the coil. Coronal and axial T1 weighted images were obtained of each animal using a spin echo pulse sequence with the following parameters: TR 300 msec, TE 15 msec, slice thickness 5 mm, matrix 128×256, field of view 10 cm, 4 excitations and no phase wrap. Next, 17 umol/kg of the Gd(III)texaphyrin complex dissolved in normal saline was infused at a rate of 0.25 ml/min intravenously and repeat images were obtained at 10–15 minutes post contrast. One tumor-bearing rat was studied at 6 and 28 hours post-contrast. All tuning parameters and the rats' positions were kept identical in the pre and post contrast scans.

Image Analysis: Operator defined regions of interest (ROI) measurements were made on axial slices of all pre and 10–15 minutes post contrast studies. Regions in which measurements were made included the right lobes of the livers and the whole kidneys in the normal rats and the whole tumor in tumor-bearing rats. In addition, large ROI's of background air were measured for standardization purposes. Standardized signal intensities (SSI) were calculated as follows: signal intensity (SI) of organ/SI air. An unpaired Student's t test was used to compare pre contrast and post contrast SSIs.

Toxicity: At 24 hours, there were no deaths in the mice injected i.p. although those receiving the highest dose (312.5 umol/kg) appeared lethargic. Autopsies of two mice from each dosage group revealed some edema and pallor of the liver and kidneys in the two groups receiving the highest doses (312.5 and 156.3 umol/kg). Autopsies from the remaining groups were normal. At 48 hours, the remaining mice (n=3 in each dosage group) in the two highest dosage groups died. The animals in the three lower dosage groups demonstrated no morbidity. There was no mortality or evidence of morbidity in the rats during the month of observation after scanning.

Enhancement: Liver SSI increased by 81.7% ($p<0.001$), kidney by 114.9% ($p < 0.001$) and tumor by 49.7% ($p<0.02$) from pre to 10–15 minutes post contrast. There was no significant difference in enhancement between the right and left lobe of the liver and between the two kidneys. Pre contrast, tumor parenchyma appeared homogeneous and of an intensity similar to adjacent muscle. Post contrast, tumor tissue demonstrated a mottled pattern of enhancement and was easily distinguished from adjacent tissues. The MRI appearance reflected the heterogeneous appearance of the tumor grossly which consists of necrotic tissue surrounded by viable stroma. In addition, in the one animal studied at 6 and 28 hours post contrast, there was visible tumor enhancement throughout the study period. The pattern of enhancement, however, changed over time, with enhancement starting at the edges of the tumor initially and including the center by 28 hours.

These results show that the T2B2 gadolinium complex is an hepatic, renal and tumor-specific contrast agent. The agent was found to have relatively low toxicity in rodents. Intravenous administration resulted in statistically significant hepatic, renal and tumor enhancement in rats within 10–15 minutes with persistence of tumor enhancement for up to 28 hours. The early enhancement of tumor edges may represent contrast localization in areas of viable tumor. The later appearance of the tumor probably was caused by passive diffusion of some of the agent into central necrotic areas. It is unclear whether a selective transport or passive diffusion mechanism is responsible for initial tumor enhancement with GD(III)texaphyrin and whether intracellular binding to peripheral-type benzodiazepene receptors occurs. The tumor could be differentiated from adjacent tissues for up to 28 hours.

The chemical properties of this texaphyrin class of macrocyclic ligands can be varied by peripheral substitution, which would allow biological properties to be optimized in terms of biodistribution, pharmacokinetics and toxicity.

Magnetic Resonance Imaging of Atheroma.

The gadolinium complex of B2T2 [4,5-diethyl-10,23-dimethyl-9,24-bis(3-hydroxypropyl)-16,17-(3-hydroxypropyloxy)-13,20,25,26,27-pentaazapentacyclo[20.2.1.1$^{3,6}$.1$^{8,11}$.0$^{14,19}$]heptacosa-1,3,5,7,9,11(27),12,14(19),15,17,20,22(25),23-tridecaene] shows accumulation in human cadaveric aorta. Two aortas obtained from autopsies were examined using magnetic resonance imaging before and after incubation in vitro for 15 minutes with the gadolinium complex of B2T2. Selective labeling of the endothelial cell surface and atheromas plaque relative to surrounding tissue was observed. These data indicate that the Gd(III)B2T2 complex has utility in the non-invasive imaging of atheroma.

Magnetic Resonance Imaging of the Upper GI Tract. The gadolinium complex of B2T2 [4,5-diethyl-10,23-dimethyl-9,24bis-(3-hydroxypropyl)-16,17-(3-hydroxypropyloxy)-13,20,25,26,27-pentaazapentacyclo[20.2.1.1$^{3,6}$.1$^{8,11}$.0$^{14,19}$] heptacosa-1,3,5,7,9,11 (27),12,14(19),15,17,20,22(25),23-tridecaene] shows accumulation in the upper GI tract, especially the stomach, as determined by magnetic resonance imaging.

Magnetic Resonance Imaging of a Carcinoma Implanted in Rabbit Thigh Muscle. A rabbit bearing a transplanted V2 carcinoma in thigh muscle was administered 5 μmol Gd(III)B2T2 (acetate)$_2$ per kg body weight. Axial MRI scans were made before (37A) 30 minutes (37B) and 3 hours (37C) after administration. The pulsing sequences used were conventional spin echo sequences TR/TE=300/15, 16 KHz., 3 mm slice thickness and 256×192 matrix, 2 NEX, saturation inferiorly and superiorly with no phase rap.

Image enhancement of the implanted V2 carcinoma was achieved at doses as low as 5 μmol/kg (FIGS. 37A, 37B and 37C) and viable liver image augmentation was obtained when using doses as low as 2 μmol/kg. It is clear that Gd(III)B2T2 is able to localize in hypoxic areas of tumors as seen in the photographs of FIGS. 37A, 37B and 37C. No signs of acute toxicity were observed in any of these studies and no serious toxicity has been observed in healthy rats given daily 40 μmol/kg doses of GdB2T2(acetate)$_2$. Thus, the quantities needed for tumor and target organ enhancement appear to be safe.

Fluorescence imaging. A metal-free texaphyrin such as the ring-N derivative of texaphyrin shown in FIG. 20 is preferred for fluorescence imaging since the presence of a metal decreases the fluorescence of texaphyrins (Sessler et al., 1991). The fluorescence emission occurs 20 nm farther to the red wavelengths in relation to the absorbing wavelengths. Fluorescence may be useful in the imaging of skin tumors or in localization using fiber optics.

Gamma irradiation for localization. Standard radiowave protons are used for magnetic resonance imaging, however, photons in several regions of the electromagnetic spectrum are suitable for medical imaging. Gamma-ray photons are used for position emission tomography (PET) and single-photon emission computed tomography (SPECT); x-ray photons are used for conventional radiography, computed tomography, digital subtraction angiography (DSA) and iodine K-edge dichromography (ID). The use of internal x-ray emitting isotopes is discussed in Example 10.

EXAMPLE 12

Radiation Sensitization of Tumor Cells Using Gadolinium Texaphyrin

This example describes the use of GdT2B2 as a radiosensitizer to enhance the radiolysis of a mouse L1210 leukemia cell line. Where GdTX is referred to in the drawings, the texaphyrin metal complex GdT2B2 was used. The presence of the metal is not important for the radiosensitization properties of texaphyrins, however, the metal contributes stability to the texaphyrin complex.

Oxygen is the ultimate electron acceptor in physiological systems. However, the texaphyrins of the present invention have a redox potential below that of oxygen. All reductants will reduce texaphyrin, even superoxide.

$e_q^- = -2.80$ V.

Porphyrin = $-0.6$ to $-1.8$ V.

Quinone = $-0.2$ to $-1.0$ V.

$O_2^- = -0.18$ V.

$GdTXP^{108} = +0.08$ V.

Therefore, gadolinium texaphyrin "soaks up" electrons readily, and prevents them from neutralizing hydroxyl radicals. This advantageous low redox potential of gadolinium texaphyrin confers a degree of specificity to radiation damage using texaphyrin; in the absence of texaphyrin, hydroxyl radicals and solvated electrons recombine and little radiation damage occurs, in the presence of texaphyrin, hydroxyl radicals are free to do their damage. Furthermore, the trapping of electrons by texaphyrin prevents the solvated electrons from interacting with the hydroxyl radical-induced damage site to repair the damage.

A second mechanism by which texaphyrin exerts radiation damage is demonstrated by experiments carried out in isopropanol. When an aqueous solution of isopropanol is irradiated, a proton is lost from the center carbon atom generating an isopropanol radical. The proton combines with a hydroxyl radical formed from water and neutralizes it. Therefore, all radiation products in an isopropanol solution are reducing radicals and isopropanol provides an appropriate environment for pulse radiolysis experiments.

Experimental Conditions. Pulse radiolysis studies were made with the CFKR 4 MeV Van der Graaff electron beam accelerator. For reduction studies, GdT2B2 was dissolved in purified water containing phosphate buffer (2 mM, pH 7) and propan-2-ol (2M) so as to give a 100 µM solution. The solution was purged thoroughly with $N_2$ before exposure to the ionizing pulse. The course of reaction was followed by optical spectroscopy. In separate studies, the solution was purged with pre-analyzed mixtures of $N_2$ and $O_2$. The radiation dose was measured by the thiocyanate dosimeter.

The successive reduction of GdT2B2 was achieved by exposure of a solution to a series of bursts of ionizing radiation. Each burst consisted of 20 individual pulses from the accelerator and the course of reaction was followed by optical absorption spectroscopy. Composition of the solution was as above.

For cytotoxicity studies, the radiation source was a Phillips 50 KVP constant potential X-ray generator, model 120.102.1 equipped with a Machlett OEG60 X-ray tube. Dosimetry was made with the Friecke dosimeter. This system delivers 110 Gy per minute into a target area of about 2 cm diameter. Samples were contained in petri dishes mounted into a 12 well tray. Three unirradiated dishes and 3 dishes containing cells without GdT2B2 served as control experiments. Six dishes containing cells and GdT2B2 were exposed to radiation for a predetermined period. A mechanical arm moved the tray after each exposure. After radiolysis, cells were incubated for 24 hours and cell viability was established by both methyl red concentration and trypan blue exclusion methods using conventional cell counting techniques. All experiments were conducted with log phase cells ($5 \times 10^5$ cells per mL). Mouse leukemia L1210 cells were maintained in RPMI 1640 cell culture medium.

A stock solution of GdT2B2 (1 mM) was prepared in purified water and small aliquots were added to cell suspensions ($5 \times 10$ cell per mL). The mixture was incubated for 1 hour at 37° C. before being isolated, washed, and resuspended in nutrient solution. In most cases, the concentration of GdT2B2 was 80 µM as measured by absorption spectroscopy.

Radiation-induced cleavage of intracellular DNA (or RNA) was measured by alkaline elution chromatography. Polyvinylchloride filters (pore size 2 µm) were used. Samples were exposed to a total of 20 Gy radiation.

Results. Pulse radiolysis experiments carried out with GdTXP in aqueous isopropanol are demonstrated in FIGS. 31, 32A and 32B. FIG. 31 demonstrates GdTXP⁻ anion formation. FIG. 32A demonstrates the anion decay in an oxygen free solution and in 32B, decay in the presence of $O_2$. The data indicate the remarkable stability of the GdTXP anion and demonstrate that GdTXP⁻ does not pass its electrons to oxygen, nor is it affected by the presence of oxygen. The data suggest the following intermediate radiolysis products for GdTXP:

TABLE 1

Pulse Radiolysis in Aqueous Isopropanol

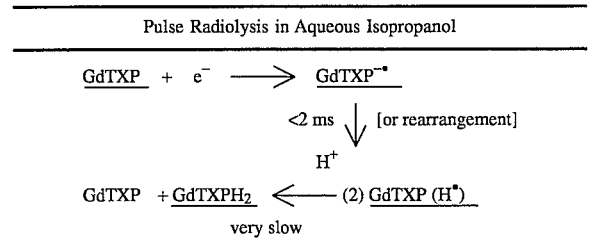

The GdTXP⁻ anion has a half life of less than 2 milliseconds, it picks up a proton or rearranges to the texaphyrin radical, GdTXP(H·), which has significant stability and a relatively long half life, greater than 100 milliseconds and possibly as long as 2 seconds.

A G value is defined as a radiation chemical yield. The radiation chemical yield of each of the radiolysis products of water is: HO·, 2.8; H·, 0.4; and $e_q^-$, 2.8. Therefore, the radiation chemical yield for water is 6, i.e., the G value is 6. A gamma radiolysis experiment in aqueous isopropanol for GdTXP demonstrated a G value of 2.8. One-half of the radiation equivalents are lost, probably because two GdTXP(H·) radicals are reacting together to form GdTXP and GdTXPH₂. These data indicate that the GdTXP(H·) radical is reactive, which is desirable for a radiosensitizer since a completely stable radical is not useful. The radical reacts with itself when it is the only species present (as in these experiments in isopropanol) but will react with neighboring molecules in a physiological system as presented in FIG. 33.

Data in FIG. 33 present the rate constant for the reaction of the GdTXP(H·) radical with cytosine, one of the four nucleotide bases of DNA and RNA. It appears that GdTXP(H·) is forming a covalent bond with cytosine, this reaction would probably inactivate the nucleic acid to which it bound.

Gadolinium texaphyrin, therefore, has three advantageous properties for use as a radiosensitizer:

i) the low redox potential of GdTXP causes solvated electrons to flow to GdTXP, allowing OH· to do its damage, ii) the GdTXP(H·) radical is relatively stable, yet reacts readily to covalently modify neighboring molecules, and iii) the GdTXP may be particularly effective for treating the hypoxic areas of solid tumors because of intrinsic biolocalization and its indifference to the presence of $O_2$.

FIG. 34 presents data from an experiment in which mouse L1210 cells were exposed to 20 μM GdTXP and radiation. The control curve represents cell kill in the absence of GdTXP, the curve labeled GdTXP represents cell kill in the presence of GdTXP. A sensitizer enhancement ratio (SER) is the ratio of the dose needed to kill 95% of the cells without GdTXP divided by the dose needed to kill 95% of the cells with GdTXP. If the sensitizer had no effect, the ratio would be 1.0; a very effective sensitizer would have a ratio of 3.0. The data of FIG. 34 indicate that at 20 μM, GdTXP has an SER of 1.62. (An SER above 1.5 is clinically significant.)

The SER increases with increasing concentrations of GdTXP as indicated in FIG. 35. For example, at 80 μM, the SER is greater than 2.2, indicating that the highest physiological tolerable level of GdTXP is desirable for radiosensitization purposes.

Total nucleic acid samples obtained from L1210 cells exposed to a total of 20 Gy radiation and varying levels of GdTXP were passed through a size selection filter. The data of FIG. 36 indicate that no nucleic acid passed through the filter in the absence of GdTXP and that in the presence of GdTXP, nucleic acid was cleaved into fragments that passed through the filter. A larger amount of fragments was produced with higher levels of GdTXP exposure. Clearly, nucleic acid strand scission occurs as a result of radiation in the presence of GdTXP. It is probable that the hydroxyl radical is responsible for the strand scission.

The radiosensitization properties of the texaphyrins described herein may allow reduced doses of radiation to be effective in treatment of an individual. Therefore, radiation side effects such as nausea and damage to normal cells may be lessened when treatment includes the use of texaphyrins of the present invention. Expected dose levels for an individual may range from 2–8 mg/kg administered for a period of 2 to 24 hours.

EXAMPLE 13

Photodynamic Therapy, In vitro and In vivo Experiments

In vitro data and experiments. The lanthanum complex of B2T2 [4,5-diethyl-10,23-dimethyl-9,24-bis(3-hydroxypropyl)-16,17-(3-hydroxypropyloxy)-13,20,25,26,27-pentaazapentacyclo [20.2.1.1$^{3,6}$.1$^{8,11}$.0$^{14,19}$]heptacosa-1,3,5,7,9,11(27),12,14(19),15,17, 20,22(25),23-tridecaene] (LaB2T2) was used at concentrations of 5.0, 1.0 or 0.1 micromolar in tissue culture medium. The murine mammary carcinoma cell line designated EMT-6 was cultured in medium containing LaB2T2 for 1 hour or 3 hours in the dark. Experimental cultures were irradiated with 10 Joules/cm$^2$ using an arc lamp with a 750 nanometer band pass filter. Cell survival was measured using a cell cloning assay. There was no dark toxicity indicating that LaB2T2 had no direct toxicity to the cells. Cultures which were irradiated with the visible red light showed viabilities of 3%, 50% and 100% for concentrations of LaB2T2 of 5.0, 1.0 and 0.1 micromolar respectively. The results were similar for 1 and 3 hour incubation periods. The results established that LaB2T2 was phototoxic to these tumor cells in vitro.

In vivo experiments. Murine adenocarcinoma cells were inoculated into both flanks of Balb/c mice. Four days later, palpable tumor masses were present on both flanks of the mice. Ten mg/kg of lutetium B2T2 (LuB2T2) in aqueous solution was injected iv. Seven hours later, one tumor mass was irradiated with 500 Joules of Argon laser light at 746 nanometers. The unirradiated tumor served as a control. Animals were monitored daily and tumor measurements were made using calipers. Following a single treatment, 65% cell kill was estimated based on the reduction in size of the treated tumors. No phototoxicity of skin or normal tissues surrounding the tumors was observed indicating relatively selective uptake of the LuB2T2 in the tumors. This experiment established the in vivo photodynamic activity of LuB2T2 in vivo.

The hydroxy-substituted texaphyrins can be conjugated to biological molecules, especially proteins of molecular weight greater than about 20,000 daltons, e.g. albumin and gamma globulin, in order to slow their clearance by the kidneys. A prolonged presence of these complexes in tissue may be desirable for photoirradiation purposes. The conjugation would be accomplished as described in Example 10 for biomolecule conjugates.

EXAMPLE 14

Hydroxy-Substituted Texaphyrins for Radiosensitization and Localization followed by Radiotherapy and/or Photodynamic Tumor Therapy for Tumor Destruction This example describes the use of hydroxy substituted texaphyrins in the localization, radiosensitization and destruction of tumor tissue. A water soluble hydroxy-substituted texaphyrin is administered to a host harboring benign or malignant tumor cells. The texaphyrin exhibits radiosensitization properties and selective biolocalization in benign or malignant tumor cells relative to surrounding tissue. Localization sites in the host are determined by reference to the texaphyrin using, for example, magnetic resonance imaging when a paramagnetic metal complex of texaphyrin is administered, fluorescence when a free-base texaphyrin is administered, or gamma body scanning when a gamma-emitting metal is complexed with the administered texaphyrin. A preferred paramagnetic metal is Gd (III).

The inherent radiosensitization properties of the texaphyrins as described in Example 12 allow electromagnetic radiation to be more effective and selective when administered in the vicinity of the texaphyrin metal complex. Lower doses of radiation may therefore be used. The radiation may be from an external source or may be from an internal source, such as a radiometal bound to a texaphyrin. Examples of a radiometal include $^{153}$Gd, $^{111}$In, or $^{90}$Y. Alternatively, a second texaphyrin metal complex having essentially identical biolocalization property and exhibiting the ability to generate singlet oxygen upon exposure to light is administered. The second texaphyrin metal complex is photoirradiated in proximity to the benign or malignant tumor cells, as in fiber optics, to cause tumor tissue destruction from the singlet oxygen produced. The detectable metal in the second texaphyrin metal complex is a diamagnetic metal, preferably La(III), Lu(III) or In(III).

A further embodiment is the use of a texaphyrin radiosensitizer and a photosensitive texaphyrin for treatment. This molecule may be a single texaphyrin metal diamagnetic complex, since the metal is not important for radiosensitization. A synergistic killing of cells may then be achieved by the use of light for photodynamic therapy in combination with electromagnetic radiation. An alternative embodiment is a synergistic killing due to an intrinsic radiochelated texaphyrin and externally applied radiation. In vitro uses of the method of radiosensitization and radiation therapy include sterilizations, and in the treatment of bone marrow, transfused blood or transplanted organs.

Texaphyrin-metal complexes will be chosen which themselves show a high intrinsic biolocalization selectivity for tumors or neoplastic tissues. For example, the B2T2 Gd(III) complex demonstrates in vivo affinity for tissue high in lipid content, atheroma, the liver, kidneys and tumors.

The hydroxy substituted texaphyrin complexes are good candidates for such biomedical radiosensitizers and photosensitizers. They "soak up" electrons in an irradiated area allowing hydroxyl radicals to cause radiation damage, the texaphyrin radicals react covalently with neighboring molecules causing further radiation damage, they are easily available, have low intrinsic cytotoxicity, long wavelength absorption, generate singlet oxygen, are soluble in physiological environments, have the ability to be conjugated to site specific transport molecules, have quick elimination, are stable and are easily subject to synthetic modification. Significant advantages to using texaphyrins for imaging and destruction of cells are i) one texaphyrin is used for both functions, ii) the inherent selective biolocalization and the potential for derivatization to enhance further localization, iii) due to the radiosensitization properties of texaphyrin, radiation is more effective and lower doses of radiation may be used, therefore, fewer side effects are experienced and iv) a metal complex is not necessary for radiosensitization. The present invention provides a method to "see" and "kill" particular cells with a single agent having biolocalization selectivity and radiation enhancing properties.

The following references are incorporated in pertinent part by reference herein for the reasons Cited below.

REFERENCES

Agrawal, S., and Tang, J. Y., *Tetrahedron Letters,* 31:7541 (1990).
Biaglow, J. E. et al., *Radiat. Res.,* 95:437 (1983).
Brock, W. A. et al. *Can. Bull.,* 39(2):98 (1987).
Cadet, J. et al., *Radiat. Phys. Chem.,* 32 (2):197 (1988).
Caracciolo et al., *Science,* 245: 1107 (1989).
Daoud, S. S., Forde, N. H., *Can. Cheroother. Pharmacol.,* 28:370 (1991).
Furuta et al., *J. Am. Chem. Soc.,* 113:4706–4707 and 6677–6678 (1991)
Grau, C., Overgaard, J., Can. Chemother. Pharmacol., 30:277 (1992).
Grau, C., Overgaard, J., *Radiother. Oncol.,* 13:301 (1988).
Hill, B. T., *Can. Treat. Rev.,* 18:149 (1991).
*J. Org. Chem.,* 55:4693–4699, (1990).
Kale, R. K., Sitasawad, S. L., *Radiat. Phys. Chem.,* 36(3) :361 (1990).
Painter, R. B., *Radiation Biology in Cancer Research* (eds. Meyn, R. E. and Withers, H. R.), pp. 59–68. Raven Press, New York (1980).
Pan, S. S., *Can. Chemother. Pharmacol.,* 27: 187 (1990 ).
Sessler et al., *SPIE Proc. Soc. Opt. Eng.,* 1426:318–329, (1991).
Sessler et al., *J. Am. Chemo Soc.* 114:8704 (1992)
Townsend, A. J., Cowan, K. H., *Can. Bull.,* 41 (1):31 (1989).
Tritton, T. R. et al., *New Experimental Modalities in the Control of Neoplasia.* (ed., Chandra, P.), p. 195. Plenum Press, New York (1985).
U.S. Pat. No. 5,159,065.
U.S. Pat. No. 5,120,411.
U.S. Pat. No. 5,041,078.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A water soluble compound retaining lipophilicity and having the structure:

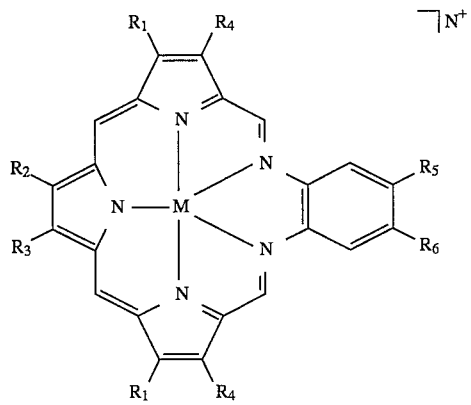

wherein

M is H, a divalent metal cation selected from the group consisting of $Ca^{+2}$, $Mn^{+2}$, $Co^{+2}$, $Ni^{+2}$, $Zn^{+2}$, $Cd^{+2}$, $Hg^{+2}$, $Fe^{+2}$, $Sm^{+2}$ and $UO_2^{+2}$ or a trivalent metal cation selected from the group consisting of $Mn^{+3}$, $Co^{+3}$, $Ni^{+3}$, $Fe^{+3}$, $Ho^{+3}$, $Ce^{+3}$, $Y^{+3}$, $In^{+3}$, $Pr^{+3}$, $Nd^{+3}$, $Sm^{+3}$, $Eu^{+3}$, $Gd^{+3}$, $Tb^{+3}$, $Dy^{+3}$, $Er^{+3}$, $Tm^{+3}$, $Yb^{+3}$, $Lu^{+3}$, $La^{+3}$, and $U^{+3}$;

$R_2$ and $R_3$ are $CH_2CH_3$, $R_4$ is $CH_3$, $R_1$, $R_5$ and $R_6$ are independently hydrogen, hydroxyl, alkyl, hydroxyalkyl, oxyalkyl, oxyhydroxyalkyl, saccharide, carboxyalkyl, carboxyamidealkyl, antibody, a peptide having affinity for a biological receptor, a sapphyrin molecule, or a couple to an antibody, a peptide having affinity for a biological receptor, or a sapphyrin molecule, where at least one of $R_1$, $R_5$, and $R_6$ is oxyhydroxyalkyl, saccharide, oxyalkyl, carboxyalkyl, carboxyamidealkyl, hydroxyalkyl, an antibody, a peptide having affinity for a biological receptor, a sapphyrin molecule, or a couple to an antibody, a peptide having affinity for a biological receptor, or a sapphyrin molecule, having at least one hydroxy substituent; and N is 0, 1 or 2.

2. The water soluble compound of claim 1 where $R_1$ is $CH_2CH_2CONCH(CH_2OH)_2$ and $R_5$ and $R_6$ are $OCH_3$.

3. The water soluble compound of claim 1 where $R_1$ is $CH_2CH_2CONCH(CH_2OH)_2$ and $R_5$ and $R_6$ are $OCH_2CH_2CH_2OH$.

4. The water soluble compound of claim 1 where $R_1$ is $CH_2CH_2CONCH(CH_2OH)_2$ and $R_5$ and $R_6$ are $OCH_2CH_2OH$.

5. The water soluble compound of claim 1 where $R_1$ is $CH_2CH_2CONCH(CH_2OH)_2$ and $R_5$ and $R_6$ are $O(CH_2CH_2O)_nCH_2CH_2OR'$, where n is an integer less than or equal to 10 and R' is H or $CH_3$.

6. The water soluble compound of claim 1 where $R_1$ is $CH_2CH_2CONCH(CH_2OH)_2$ and $R_5$ and $R_6$ are independently H or $CH_3$.

7. The water soluble compound of claim 1 where $R_1$ is $CH_2CH_2CONCH(CH_2OH)_2$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

8. The water soluble compound of claim 1 where $R_1$ is $CH_2CH_2CON(CH_2CH_2OH)_2$ and $R_5$ and $R_6$ are $OCH_3$.

9. The water soluble compound of claim 1 where $R_1$ is $CH_2CH_2CON(CH_2CH_2OH)_2$ and $R_5$ and $R_6$ are $OCH_2CH_2CH_2OH$.

10. The water soluble compound of claim 1 where $R_1$ is $CH_2CH_2CON(CH_2CH_2OH)_2$ and $R_5$ and $R_6$ are $OCH_2CH_2OH$.

11. The water soluble compound of claim 1 where $R_1$ is $CH_2CH_2CON(CH_2CH_2OH)_2$ and $R_5$ and $R_6$ are $O(CH_2CH_2O)_nCH_2CH_2OR'$, where n is an integer less than or equal to 10 and R' is H or $CH_3$.

12. The water soluble compound of claim 1 where $R_1$ is $CH_2CH_2CON(CH_2CH_2OH)_2$ and $R_5$ and $R_6$ are independently H or $CH_3$.

13. The water soluble compound of claim 1 where $R_1$ is $CH_2CH_2CON(CH_2CH_2OH)_2$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

14. The water soluble compound of claim 1 where $R_1$ is $CH_2CH_2CONHCH_2CH(OH)CH(OH)CH(OH)CH(OH)CH_2OH$ and $R_5$ and $R_6$ are $OCH_3$.

15. The water soluble compound of claim 1 where $R_1$ is $CH_2CH_2CONHCH_2CH(OH)CH(OH)CH(OH)CH(OH)CH_2OH$ and $R_5$ and $R_6$ are $OCH_2CH_2CH_2OH$.

16. The water soluble compound of claim 1 where $R_1$ is $CH_2CH_2CONHCH_2CH(OH)CH(OH)CH(OH)CH(OH)CH_2OH$ and $R_5$ and $R_6$ are $OCH_2CH_2OH$.

17. The water soluble compound of claim 1 where $R_1$ is $CH_2CH_2CONHCH_2CH(OH)CH(OH)CH(OH)CH(OH)CH_2OH$ and $R_5$ and $R_6$ are $O(CH_2CH_{20})_nCH_2CH_2OR'$, where n is an integer less than or equal to 10 and R' is H or $CH_3$.

18. The water soluble compound of claim 1 where $R_1$ is $CH_2CH_2CONHCH_2CH(OH)CH(OH)CH(OH)CH(OH)CH_2OH$ and $R_5$ and $R_6$ are independently H or $CH_3$.

19. The water soluble compound of claim 1 where $R_1$ is $CH_2CH_2CONHCH_2CH(OH)CH(OH)CH(OH)CH(OH)CH_2OH$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

20. The water soluble compound of claim 1 where $R_1$ is $CH_2CH_2CH_2OH$ and $R_5$ and $R_6$ are $OCH_3$.

21. The water soluble compound of claim 1 where $R_1$ is $CH_2CH_2CH_2OH$ and $R_5$ and $R_6$ are $OCH_2CH_2CH_2OH$.

22. The water soluble compound of claim 1 where $R_1$ is $CH_2CH_2CH_2OH$ and $R_5$ and $R_6$ are $OCH_2CH_2OH$.

23. The water soluble compound of claim 1 where $R_1$ is $CH_2CH_2CH_2OH$ and $R_5$ and $R_6$ are $O(CH_2CH_{20})_nCH_2CH_2OR'$, where n is an integer less than or equal to 10 and R' is H or CHB.

24. The water soluble compound of claim 1 where $R_1$ is $CH_2CH_2CH_2OH$ and $R_5$ and $R_6$ are independently H or $CH_3$.

25. The water soluble compound of claim 1 where $R_1$ is $CH_2CH_2CH_2OH$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

26. The water soluble compound of claim 1 where $R_1$ is $CH_2CH_2CONHC_6H_{11}O_5$ and $R_5$ and $R_6$ are $OCH_3$.

27. The water soluble compound of claim 1 where $R_1$ is $CH_2CH_2CONHC_6H_{11}O_5$ and $R_5$ and $R_6$ are $OCH_2CH_2CH_2OH$.

28. The water soluble compound of claim 1 where $R_1$ is $CH_2CH_2CONHC_6H_{11}O_5$ and $R_5$ and $R_6$ are $OCH_2CH_2OH$.

29. The water soluble compound of claim 1 where $R_1$ is $CH_2CH_2CONHC_6H_{11}O_5$ and $R_5$ and $R_6$ are $O(CH_2CH_2O)_nCH_2CH_2OR'$, where n is an integer less than or equal to 10 and R' is H or $CH_3$.

30. The water soluble compound of claim 1 where $R_1$ is $CH_2CH_2CONHC_6H_{11}O_5$ and $R_5$ and $R_6$ are independently H or $CH_3$.

31. The water soluble compound of claim 1 where $R_1$ is $CH_2CH_2CONHC_6H_{11}O_5$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

32. The water soluble compound of claim 1 where $R_1$ is $CH_2CH_2COOC_6H_{11}O_5$ and $R_5$ and $R_6$ are $OCH_3$.

33. The water soluble compound of claim 1 where $R_1$ is $CH_2CH_2COOC_6H_{11}O_5$ and $R_5$ and $R_6$ are $OCH_2CH_2CH_2OH$.

34. The water soluble compound of claim 1 where $R_1$ is $CH_2CH_2COOC_6H_{11}O_5$ and $R_5$ and $R_6$ are $OCH_2CH_2OH$.

35. The water soluble compound of claim 1 where $R_1$ is $CH_2CH_2COOC_6H_{11}O_5$ and $R_5$ and $R_6$ are $O(CH_2CH_2O)_nCH_2CH_2OR'$, where n is an integer less than or equal to 10 and R' is H or $CH_3$.

36. The water soluble compound of claim 1 where $R_1$ is $CH_2CH_2COOC_6H_{11}O_5$ and $R_5$ and $R_6$ are independently H or $CH_3$.

37. The water soluble compound of claim 1 where $R_1$ is $CH_2CH_2COOC_6H_{11}O_5$, $R_5$ is $CH_3$, and $R_6$ is H, $CH_3$, $OCH_3$, $OCH_2CH_2OH$, $OCH_2CH_2CH_2OH$, or $O(CH_2CH_2O)_nCH_2CH_2OR'$, where n is an integer less than or equal to 10 and R' is H or $CH_3$.

38. The water-soluble compound of claim 1 wherein the oxyhydroxyalkyl is $C_{(n-x)}H_{((2n+1)-2x)}O_xO_y$ or $OC_{(n-x)}H_{((2n+1)-2x)}O_xO_y$ where n is a positive integer from 1 to 10;

x is zero or a positive integer less than or equal to n; and y is zero or a positive integer less than or equal to $((2n+1)-2x)$.

39. The water soluble compound of claim 1 wherein the oxyhydroxyalkyl or saccharide is $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to $2n+1$, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H alkyl hydroxyalkyl or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

40. The water soluble compound of claim 1 wherein the carboxyamidealkyl is $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

41. The water soluble compound of claim 1 wherein the carboxyalkyl is $C_nH_{((2n+1)-q)}O_yR^c_q$ or $OC_nH_{((2n+1)-q)}O_yR^c_q$ where n is a positive integer from 1 to 10;

y is zero or a positive integer less than $((2n+1)-q)$, q is zero or a positive integer less than or equal to $2n+1$, $R^c$ is $(CH_2)_nCO_2R^d$, $(CH_2)_nCONHR^d$ or $(CH_2)_nCON(R^d)_2$ where n is a positive integer from 1 to 10;

$R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$, where m is a positive integer from 1 to 10, w is zero or a positive integer less than or equal to m, z is zero or a positive integer less than or equal to $((2m+1)-2w)$, R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to $2m+1$, and $R^b$ is independently H, alkyl, hydroxyalkyl, or saccharide.

42. The water soluble compound of claim 1 where $R_1$ is $CH_2CH_2CH_2OH$ and $R_5$ and $R_6$ are $O(CH_2CH_2O)_2CH_2CH_2OR'$, where R' is H or $CH_3$.

43. The water soluble compound of claim 1 where $R_1$ is $CH_2CH_2CH_2OH$ and $R_5$ and $R_6$ are $O(CH_2CH_2O)_2CH_2CH_2OCH_3$.

44. The water soluble compound of claim 23 wherein n is 2 and R' is $CH_3$.

45. The water soluble compound of claim 42, 43 or 44 wherein M is $Gd^{+3}$.

46. The water soluble compound of claim 42, 43 or 44 wherein M is $Lu^{+3}$.

47. The water soluble compound of claim 1 where $R_1$ is $CH_2CH_2CH_2OH$ and $R_5$ and $R_6$ are $OCH_2COOH$ or $OCH_2CH_2COOH$.

48. The water soluble compound of claim 1 where $R_1$ is $CH_2CH_2CH_2OH$ and $R_5$ and $R_6$ are $OCH_2CH_2CONHC(CH_2OH)_3$; $OCH_2CH_2CH_2NHCO[CH(OH)]_4CH_2OH$; $OCH_2CH_2C(CH_2OH)_3$; or $OCH_2CH_2COOCH_2C(CH_2OH)_3$.

49. The water soluble compound of claim 1 wherein $R_1$ is $CH_2CH_2CH_2OH$; $R_5$ is $(O)_m(CH_2)_nCONHR$, where m is zero or 1; n is zero, 1, 2, or 3; and R is an aminosugar, a polysaccharide, an oligosaccharide, or an oligopeptide; and $R_6$ is H, OH, $OCH_3$, $O(CH_2)_2OH$, $O(CH_2)_3OH$, or COOH.

50. The water soluble compound of claim 1 where $R_1$ is $CH_2CH_2CH_2OH$; $R_5$ is $(O)_m(CH_2)_nCONHR$, where m is zero or 1; n is zero, 1, 2, or 3; and R is glucosamine, galactosamine, mannosamine, poly-L-lysine, derivatized poly-L-lysine, $(LysAla)_n$, $(LysLeuAla)_n$, polyglutamic acid, polyornithine, or heparin; and $R_6$ is H, OH, $OCH_3$, $O(CH_2)_2OH$, $O(CH_2)_3OH$, or COOH.

51. The water soluble compound of claim 49 or 50 where $R_6$ is H.

52. The water soluble compound of claim 1 were $R_1$ is $CH_2(CH_2CH_2O)_nCH_2CH_2OR$, where n is an integerless than or equal to 10 and R is H or $CH_3$; and $R_5$ and $R_6$ are $OCH_3$, $OCH_2CH_2OH$; $OCH_2CH_2CH_2OH$; $O(CH_2CH_2O)_nCH_2CH_2OR'$, where n is an integer less than or equal to 10 and R' is H or $CH_3$; or independently H or $CH_3$.

53. The water soluble compound of claim 52 where $R_5$ and $R_6$ are $OCH_2CH_2CH_2OH$.

54. The water soluble compound of claim 1 where $R_1$ is $(CH_2)_nCON(R')R$, where n is 1, 2, or 3, R' is H or $CH_3$, and R is an aminosugar, a polysaccharide, an oligosaccharide, or an oligopeptide; and $R_5$ and $R_6$ are $CH_3$, $OCH_3$, $O(CH_2)_2OH$, or $O(CH_2)_3OH$.

55. The water soluble compound of claim 1 where $R_1$ is $O(CH_2)_nCON(R')R$, where n is 1, 2, or 3, R' is H or $CH_3$, and R is glucosamine, galactosamine, mannosamine, poly-L-lysine, derivatized poly-L-lysine, $(LysAla)_n$, $(LysLeuAla)_n$, polyglutamic acid, polyornithine, or heparin; and $R_5$ and $R_6$ are $CH_3$, $OCH_3$, $O(CH_2)_2OH$, or $O(CH_2)_3OH$.

56. The water soluble compound of claim 1 where $R_5$ and $R_6$ are $OCH_2CH_2OHCH_2OH$.

57. The water soluble compound of claim 23 wherein M is $Mn^{+2}$ or $Mn^{+3}$.

58. The water soluble compound of claim 43 wherein M is $Mn^{+2}$ or $Mn^{+3}$.

59. The water soluble compound of claim 1 where $R_1$ is $CH_2CH_2CH_2OH$, $R_5$ and $R_6$ are $OCH_2CH_2CH_2OH$, and M is $Mn^{+2}$ or $Mn^{+3}$.

* * * * *

UNITED STATES PATENT AND TRADEMARK OFFICE
CERTIFICATE OF CORRECTION

PATENT NO. : 5,457,183

DATED : October 10, 1995

INVENTOR(S) : Jonathan L. Sessler; Tarak D. Mody; Gregory W. Hemmi. Vladimir Kral It is certified that error appears in the above-indentified patent and that said Letters Patent is hereby corrected as shown below:

In claim 39, column 42, line 47, please insert -- , -- between "alkyl" and "hydroxyalkyl".

In claim 52, column 44, line 19, please delete "intergerless" and substitute therefor -- integer less --.

In claim 17, column 41, line 27, please delete "$CH_{20}$" and substitute therefor -- $CH_2O$ --.

In claim 23, column 41, line 46, please delete "$CH_{20}$" and substitute therefor -- $CH_2O$ --.

In claim 23, column 41, line 47, please delete "CHB" and substitute therefor -- $CH_3$ --.

Signed and Sealed this

Fifth Day of March, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO : 5,457,183
DATED : October 10, 1995
INVENTOR(S) : Sessler, et al.

It is certified that error appears in the above-identified patent and that said Letters Patent is hereby corrected as shown below:

On the cover page, item [ * ] Notice: please correct the reference to the Terminal Disclaimer to read as follows:

--The term of this patent shall not extend beyond the expiration date of Patent No. 5,252,720.--

At column 1, please replace the paragraph at lines 3-6 with the following:

--  The government may own certain rights in the present invention pursuant to one or more of the following: National Institutes of Health Grants CA68682, AI28845 and AI33577; and National Science Foundation Grants CHE8552768 and CHE9122161.--

Signed and Sealed this

Sixth Day of June, 2000

Attest:

Q. TODD DICKINSON

Attesting Officer

Director of Patents and Trademarks